(12) United States Patent
Cheung et al.

(10) Patent No.: US 9,624,174 B2
(45) Date of Patent: Apr. 18, 2017

(54) COMPOUNDS AS DIACYLGLYCEROL ACYLTRANSFERASE INHIBITORS

(71) Applicant: GlaxoSmithKline LLC, Wilmington, New Castle, DE (US)

(72) Inventors: Mui Cheung, King of Prussia, PA (US); Raghuram S. Tangirala, Secunderabad (IN)

(73) Assignee: GlaxoSmithKline LLC, Wilmington, New Castle, DE (US)

( * ) Notice: Subject to any disclaimer, the term of this patent is extended or adjusted under 35 U.S.C. 154(b) by 0 days.

(21) Appl. No.: 14/943,091

(22) Filed: Nov. 17, 2015

(65) Prior Publication Data
US 2016/0068487 A1    Mar. 10, 2016

Related U.S. Application Data

(63) Continuation of application No. 14/441,542, filed as application No. PCT/US2013/069024 on Nov. 8, 2013, now Pat. No. 9,221,766.

(30) Foreign Application Priority Data

Nov. 9, 2012 (IN) .......................... 3480/DEL/2012

(51) Int. Cl.

| | | |
|---|---|---|
| *A61K 31/50* | (2006.01) |
| *A61K 31/501* | (2006.01) |
| *A61K 31/4965* | (2006.01) |
| *A01N 43/40* | (2006.01) |
| *A61K 31/44* | (2006.01) |
| *A01N 43/78* | (2006.01) |
| *A61K 31/425* | (2006.01) |
| *C07D 401/00* | (2006.01) |
| *C07D 403/00* | (2006.01) |
| *C07D 405/00* | (2006.01) |
| *C07D 409/00* | (2006.01) |
| *C07D 411/00* | (2006.01) |
| *C07D 413/00* | (2006.01) |
| *C07D 417/00* | (2006.01) |
| *C07D 419/00* | (2006.01) |
| *C07D 213/04* | (2006.01) |
| *C07D 277/00* | (2006.01) |
| *C07D 213/72* | (2006.01) |
| *A61K 31/122* | (2006.01) |
| *C07D 237/20* | (2006.01) |
| *C07D 213/74* | (2006.01) |
| *C07D 277/42* | (2006.01) |
| *C07D 401/12* | (2006.01) |
| *C07D 405/12* | (2006.01) |
| *C07D 417/12* | (2006.01) |

(52) U.S. Cl.
CPC .......... *C07D 213/72* (2013.01); *A61K 31/122* (2013.01); *A61K 31/50* (2013.01); *C07D 213/74* (2013.01); *C07D 237/20* (2013.01); *C07D 277/42* (2013.01); *C07D 401/12* (2013.01); *C07D 405/12* (2013.01); *C07D 417/12* (2013.01)

(58) Field of Classification Search
None
See application file for complete search history.

(56) References Cited

U.S. PATENT DOCUMENTS 9,242,929 B2 *   1/2016   Christensen, IV ... C07D 213/75

FOREIGN PATENT DOCUMENTS

| EP | 0 885 869 A1 | 12/1998 |
| EP | 2 402 317 A1 | 1/2012 |
| WO | WO 2012/16212 | 11/2012 |

* cited by examiner

*Primary Examiner* — Jeffrey H Murray
(74) *Attorney, Agent, or Firm* — Duke M. Fitch; Kathryn A. Lutomski; Edward R. Gimmi

(57) ABSTRACT

Compounds of Formula (I) are inhibitors of acyl coenzyme A: diacylglycerol acyltransferase 1 (DGAT-1), useful in the treatment of obesity, obesity related disorders, genetic (Type 1, Type 5 hyperlipidemia) and acquired forms of hypertriglyceridemia or hyperlipoproteinemia-related disorders, caused by but not limited to lipodystrophy, hypothyroidism, medications (beta blockers, thiazides, estrogen, glucocorticoids, transplant) and other factors (pregnancy, alcohol intake), hyperlipoproteinemia, chylomicronemia, dyslipidemia, non-alcoholic steatohepatitis, diabetes, insulin resistance, metabolic syndrome, cardiovascular outcomes, angina, excess hair growth (including syndromes associated with hirsutism), nephrotic syndrome, fibrosis such as myocardial, renal and liver fibrosis, hepatitis C virus infection and acne or other skin disorders.

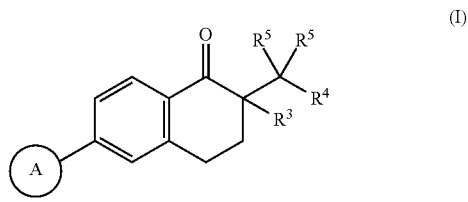

20 Claims, No Drawings

COMPOUNDS AS DIACYLGLYCEROL ACYLTRANSFERASE INHIBITORS

FIELD OF INVENTION

This invention relates to novel compounds which are inhibitors of acyl coenzyme A: diacylglycerol acyltransferase 1 (DGAT-1), to pharmaceutical compositions containing them, to processes for their preparation, and to their use in therapy, alone or in combination with weight management therapies or other triglyceride lowering therapy, for the prevention or treatment of diseases related to DGAT-1 dysfunction or where modulation of DGAT-1 activity may have therapeutic benefit including but not limited to obesity, obesity related disorders, genetic (Type 1, Type 5 hyperlipidemia) and acquired forms of hypertriglyceridemia or hyperlipoproteinemia-related disorders, caused by but not limited to lipodystrophy, hypothyroidism, medications (beta blockers, thiazides, estrogen, glucocorticoids, transplant) and other factors (pregnancy, alcohol intake), hyperlipoproteinemia, chylomicronemia, dyslipidemia, non-alcoholic steatohepatitis, diabetes, insulin resistance, metabolic syndrome, cardiovascular outcomes, angina, excess hair growth (including syndromes associated with hirsutism), nephrotic syndrome, fibrosis such as mycocardial, renal and liver fibrosis, hepatitis C virus infection and acne or other skin disorders.

BACKGROUND OF THE INVENTION

Obesity is a medical condition that is reaching epidemic proportions among humans in a number of countries throughout the world. It is a condition that is also associated with or induces other diseases or conditions that disrupt life activities and lifestyles. Obesity is recognized as a serious risk factor for other diseases and conditions such as diabetes, hypertension, and arteriosclerosis. It is also known that increased body weight due to obesity can place a burden on joints, such as knee joints, causing arthritis, pain, and stiffness.

Because overeating and obesity have become such a problem in the general population, many individuals are now interested in losing weight, reducing weight, and maintaining a healthy body weight and desirable lifestyle. One approach to treating obesity is to reduce food intake and/or hyperlipidemia. It has been suggested that molecules which are developed to prevent the accumulation of triglyceride would not only reduce obesity but also have the additional beneficial effect of reducing insulin resistance, a primary factor contributing to the development of diabetes.

Acyl coenzyme A: diacylglycerol acyltransferase 1 (DGAT-1) is one of two known DGAT enzymes that catalyze the final step in mammalian triglyceride synthesis. DGAT-1 is an enzyme that is implicated in the development of both diabetes and insulin resistance. Studies of DGAT-1 deficient mice show that DGAT-1 deficiency protects against insulin resistance and obesity, see Chen, H. C. et al., *J Clin Invest.*, 109(8), 1049-1055 (2002). Therefore, inhibitors of DGAT-1 should be useful for the treatment of metabolic disorders, e.g. obesity, Type 2 diabetes, and insulin resistance syndrome (or metabolic syndrome) and other associated or related diseases and conditions.

SUMMARY OF THE INVENTION

This invention relates to compounds for Formula (I):

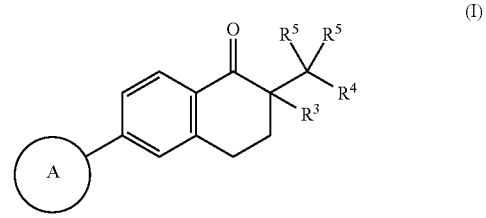

wherein:
A represents

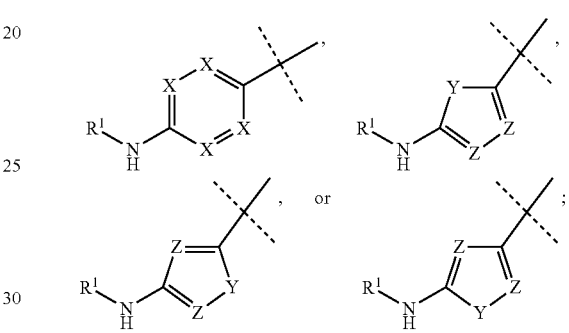

each X is independently CH, $CR^2$, or N, provided that at least one X is CH and at most two X's are N;
Y is O, S, or $NR^6$;
each Z is independently CH, $CR^2$, or N;
$R^1$ is phenyl or 5- or 6-membered heteroaryl, which is optionally substituted by —$O(C_1$-$C_2)$alkylO— or optionally substituted with one to three substituents independently selected from halogen, cyano, $(C_1$-$C_6)$alkyl, halo$(C_1$-$C_6)$alkyl, hydroxy$(C_1$-$C_4)$alkyl, cyano$(C_1$-$C_4)$alkyl, —C(O)$OR^6$, —C(O)$R^6$, and —$OR^6$;
each $R^2$ is independently selected from the group consisting of halogen, cyano, $(C_1$-$C_4)$alkyl, halo$(C_1$-$C_4)$alkyl, and —$OR^6$;
$R^3$ is $(C_1$-$C_4)$alkyl, halo$(C_1$-$C_4)$alkyl, hydroxyl, or $(C_1$-$C_4)$alkoxy;
$R^4$ is —$CH_2C(O)OH$ or —$C(O)OR^6$;
each $R^5$ is independently hydrogen or —$CH_3$; and
each $R^6$ is independently hydrogen, $(C_1$-$C_4)$alkyl, halo$(C_1$-$C_4)$alkyl, phenyl, or 5- or 6-membered heteroaryl;
or a pharmaceutically acceptable salt thereof.

This invention also relates to a pharmaceutical composition comprising a compound of Formula (I) and a pharmaceutically acceptable excipient.

This invention also relates to a method of treating obesity comprising administering to a human in need thereof an effective amount of a compound of Formula (I) or a pharmaceutically acceptable salt thereof.

DETAIL DESCRIPTION OF THE INVENTION

This invention relates to compounds of the Formula (I) as defined above.

In another embodiment, this invention also relates to compounds of Formula (II):

(II)

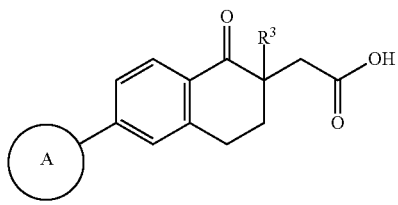

wherein:
A represents

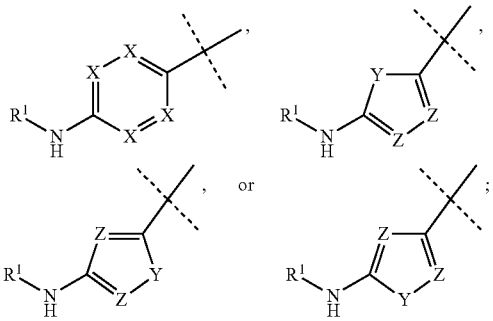

each X is independently CH, CR², or N, provided that at least one X is CH and at most two X's are N;
Y is O, S, or NR⁶;
each Z is independently CH, CR², or N;
R¹ is phenyl or 5- or 6-membered heteroaryl, which is optionally substituted by —O($C_1$-$C_2$)alkylO— or optionally substituted with one to three substituents independently selected from halogen, cyano, ($C_1$-$C_6$)alkyl, halo($C_1$-$C_6$)alkyl, hydroxy($C_1$-$C_4$)alkyl, cyano($C_1$-$C_4$)alkyl, —C(O)OR⁶, —C(O)R⁶, and —OR⁶;
each R² is independently selected from the group consisting of halogen, cyano, ($C_1$-$C_4$)alkyl, halo($C_1$-$C_4$)alkyl, and —OR⁶;
R³ is ($C_1$-$C_4$)alkyl, halo($C_1$-$C_4$)alkyl, hydroxyl, or ($C_1$-$C_4$)alkoxy; and
each R⁶ is independently hydrogen, ($C_1$-$C_4$)alkyl, halo($C_1$-$C_4$)alkyl, phenyl, or 5- or 6-membered heteroaryl;
or a pharmaceutically acceptable salt thereof.

In another embodiment, this invention also relates to compounds of Formula (III),

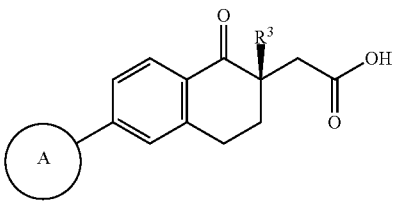

wherein:
A represents

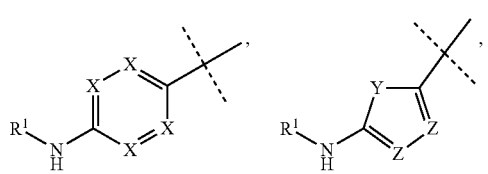

each X is independently CH, CR², or N, provided that at least one X is CH and at most two X's are N;
Y is O, S, or NR⁶;
each Z is independently CH, CR², or N;
R¹ is phenyl or 5- or 6-membered heteroaryl, which is optionally substituted by —O($C_1$-$C_2$)alkylO— or optionally substituted with one to three substituents independently selected from halogen, cyano, ($C_1$-$C_6$)alkyl, halo($C_1$-$C_6$)alkyl, hydroxy($C_1$-$C_4$)alkyl, cyano($C_1$-$C_4$)alkyl, —C(O)OR⁶, —C(O)R⁶, and —OR⁶;
each R² is independently selected from the group consisting of halogen, cyano, ($C_1$-$C_4$)alkyl, halo($C_1$-$C_4$)alkyl, and —OR⁶;
R³ is ($C_1$-$C_4$)alkyl, halo($C_1$-$C_4$)alkyl, hydroxyl, or ($C_1$-$C_4$)alkoxy; and
each R⁶ is independently hydrogen, ($C_1$-$C_4$)alkyl, halo($C_1$-$C_4$)alkyl, phenyl, or 5- or 6-membered heteroaryl;
or a pharmaceutically acceptable salt thereof.

In another embodiment, this invention also relates to compounds of Formula (IV):

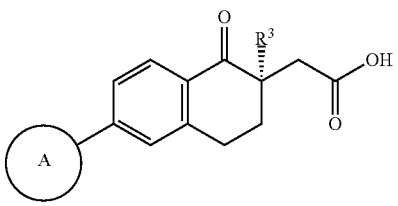

wherein:
A represents

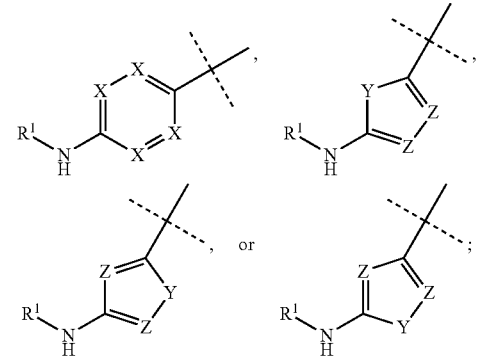

each X is independently CH, CR², or N, provided that at least one X is CH and at most two X's are N;
Y is O, S, or NR⁶;
each Z is independently CH, CR², or N;
R¹ is phenyl or 5- or 6-membered heteroaryl, which is optionally substituted by —O($C_1$-$C_2$)alkylO— or optionally substituted with one to three substituents independently selected from halogen, cyano, $(C_1-C_6)$alkyl, halo$(C_1-C_6)$alkyl, hydroxy$(C_1-C_4)$alkyl, cyano$(C_1-C_4)$alkyl, —C(O)OR$^6$, —C(O)R$^6$, and —OR$^6$;

each R$^2$ is independently selected from the group consisting of halogen, cyano, $(C_1-C_4)$alkyl, halo$(C_1-C_4)$alkyl, and —OR$^6$;

R$^3$ is $(C_1-C_4)$alkyl, halo$(C_1-C_4)$alkyl, hydroxyl, or $(C_1-C_4)$alkoxy; and each R$^6$ is independently hydrogen, $(C_1-C_4)$alkyl, halo$(C_1-C_4)$alkyl, phenyl, or 5- or 6-membered heteroaryl;

or a pharmaceutically acceptable salt thereof.

In another embodiment, this invention relates to compounds of Formula (I), (II), (III), or (IV), wherein A represents

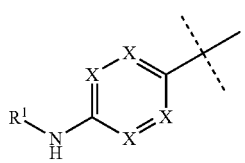

and each X is independently CH, CR$^2$, or N, provided that at least one X is CH and at most two X's are N. In another embodiment, this invention relates to compounds of Formula (I), (II), (III), or (IV), wherein A represents

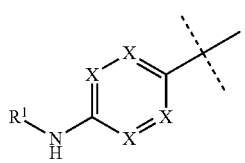

and each X is independently CH or N, provided that at most two X's are N. In another embodiment, this invention relates to compounds of Formula (I), (II), (III), or (IV), wherein A represents

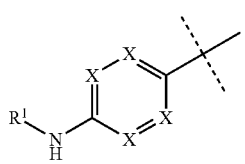

and two X's are each independently CH and the remaining two X's are each independently N. In another embodiment, this invention relates to compounds of Formula (I), (II), (III), or (IV), wherein A represents

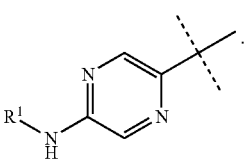

In another embodiment, this invention relates to compounds of Formula (I), (II), (III), or (IV), wherein A represents

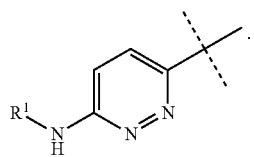

In another embodiment, this invention relates to compounds of Formula (I), (II), (III), or (IV), wherein A represents

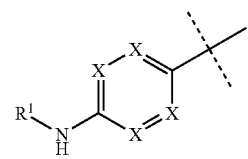

and three X's are each independently CH and the remaining X is N. In another embodiment, this invention relates to compounds of Formula (I), (II), (III), or (IV), wherein A represents

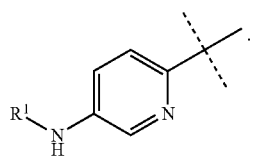

In another embodiment, this invention relates to compounds of Formula (I), (II), (III), or (IV), wherein A represents

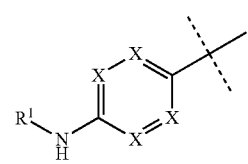

and each X is independently CH or CR$^2$, provided that at least one X is CH. In another embodiment, this invention relates to compounds of Formula (I), (II), (III), or (IV), wherein A represents

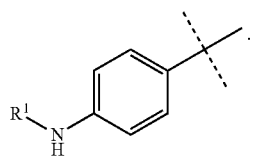

In another embodiment, this invention relates to compounds of Formula (I), (II), (III), or (IV), wherein A represents

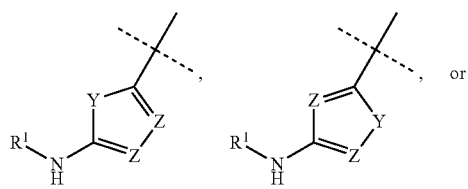

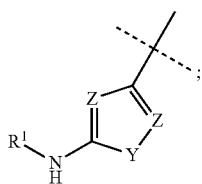

Y is O, S, or NR⁶; and each Z is independently CH, CR², or N. In another embodiment, this invention relates to compounds of Formula (I), (II), (III), or (IV), wherein A represents

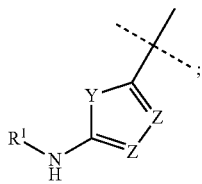

Y is O, S, or NR⁶; and each Z is independently CH, CR², or N. In another embodiment, this invention relates to compounds of Formula (I), (II), (III), or (IV), wherein A represents

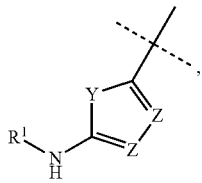

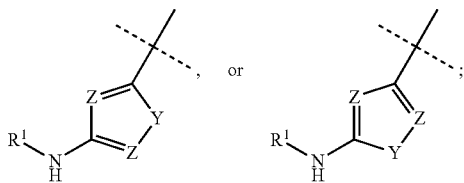

Y is O, S, or NH; and each Z is independently CH or N. In another embodiment, this invention relates to compounds of Formula (I), (II), (III), or (IV), wherein A represents

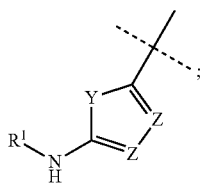

Y is O, S, or NH; and each Z is independently CH or N. In another embodiment, this invention relates to compounds of Formula (I), (II), (III), or (IV), wherein A represents

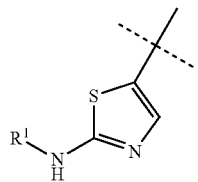

In another embodiment, this invention relates to compounds of Formula (I), (II), (III), or (IV), wherein each $R^2$ is independently selected from the group consisting of F, Cl, —CH₃, —CF₃, and —OCH₃.

In another embodiment, this invention relates to compounds of Formula (I), (II), (III), or (IV), wherein $R^3$ is (C₁-C₄)alkyl or halo(C₁-C₄)alkyl. In another embodiment, this invention relates to compounds of Formula (I), (II), (III), or (IV), wherein $R^3$ is (C₁-C₄)alkyl. In a specific embodiment, this invention relates to compounds of Formula (I), (II), (III), or (IV), wherein $R^3$ is —CH₂CH₃. In another embodiment, this invention relates to compounds of Formula (I), (II), (III), or (IV), wherein $R^3$ is halo(C₁-C₄)alkyl. In another specific embodiment, this invention relates to compounds of Formula (I), (II), (III), or (IV), wherein $R^3$ is —CH₂CF₃.

In another embodiment, this invention relates to compounds of Formula (I), (II), (III), or (IV), wherein $R^1$ is phenyl which is optionally substituted by —O(C₁-C₂)alkylO— or optionally substituted with one to three substituents independently selected from halogen, cyano, (C₁-C₆)alkyl, halo(C₁-C₆)alkyl, hydroxy(C₁-C₄)alkyl, cyano(C₁-C₄)alkyl, —C(O)OR⁶, —C(O)R⁶, and —OR⁶. In another embodiment, this invention relates to compounds of Formula (I), (II), (III), or (IV), wherein $R^1$ is phenyl which is optionally substituted by —O(C₁-C₂)alkylO— or with one or two substituents independently selected from halogen, (C₁-C₄)alkyl, halo(C₁-C₄)alkyl, hydroxyl, and (C₁-C₄)alkoxy. In another embodiment, this invention relates to compounds of Formula (I), (II), (III), or (IV), wherein $R^1$ is phenyl which is optionally substituted by —O(C₁-C₂)alkylO— or with one or two substituents independently selected from halogen, (C₁-C₄)alkyl, and halo(C₁-C₄)alkyl. In another embodiment, this invention relates to compounds of Formula (I), (II), (III), or (IV), wherein $R^1$ is phenyl which is optionally substituted by —OCH₂O— or with one or two substituents independently selected from fluorine, chlorine, methyl, and trifluoromethyl. In a specific embodiment, this invention relates to compounds of Formula (I), (II), (III), or (IV), wherein $R^1$ is 3-chlorophenyl, 4-chlorophenyl, 3,4-difluorophenyl, 4-methylphenyl, or benzo[d][1,3]dioxol-5-yl.

In another embodiment, this invention relates to compounds of Formula (I), (II), (III), or (IV), wherein $R^1$ is 5- or 6-membered heteroaryl which is optionally substituted with one to three substituents independently selected from halogen, cyano, (C₁-C₆)alkyl, halo(C₁-C₆)alkyl, hydroxy(C₁-C₄)alkyl, cyano(C₁-C₄)alkyl, —C(O)OR⁶, —C(O)R⁶, and —OR⁶. In another embodiment, this invention relates to compounds of Formula (I), (II), (III), or (IV), wherein $R^1$ is furanyl, thienyl, pyrrolyl, imidazolyl, pyrazolyl, triazolyl, tetrazolyl, oxazolyl, thiazolyl, isoxazolyl, isothiazolyl, oxadiazolyl, thiadiazolyl, pyridinyl, pyridazinyl, pyrazinyl, pyrimidinyl, or triazinyl, which is optionally substituted with one or two substituents independently selected from halogen, (C₁-C₄)alkyl, halo(C₁-C₄)alkyl, hydroxyl, and (C₁-C₄)alkoxy. In another embodiment, this invention relates to compounds of Formula (I), (II), (III), or (IV), wherein $R^1$ is furanyl, thienyl, pyrrolyl, imidazolyl, pyrazolyl, triazolyl, tetrazolyl, oxazolyl, thiazolyl, isoxazolyl, isothiazolyl, oxadiazolyl, or thiadiazolyl, which is optionally substituted with one or two substituents independently selected from halogen, $(C_1-C_4)$alkyl, halo$(C_1-C_4)$alkyl, hydroxyl, and $(C_1-C_4)$alkoxy. In a specific embodiment, this invention relates to compounds of Formula (I), (II), (III), or (IV), wherein $R^1$ is 5-methylthiazol-2-yl. In another embodiment, this invention relates to compounds of Formula (I), (II), (III), or (IV), wherein $R^1$ is pyridinyl, pyridazinyl, pyrazinyl, pyrimidinyl, or triazinyl, which is optionally substituted with one or two substituents independently selected from halogen, $(C_1-C_4)$alkyl, halo$(C_1-C_4)$alkyl, hydroxyl, and $(C_1-C_4)$alkoxy. In another embodiment, this invention relates to compounds of Formula (I), (II), (III), or (IV), wherein $R^1$ is pyridinyl which is optionally substituted with one or two substituents independently selected from halogen, $(C_1-C_4)$alkyl, and halo$(C_1-C_4)$alkyl. In another embodiment, this invention relates to compounds of Formula (I), (II), (III), or (IV), wherein $R^1$ is pyridinyl which is optionally substituted with one or two substituents independently selected from fluorine, chlorine, methyl, and trifluoromethyl. In another specific embodiment, this invention relates to compounds of Formula (I), (II), (III), or (IV), wherein $R^1$ is 5-chloropyridin-2-yl, 5-methylpyridin-2-yl, 6-methylpyridin-3-yl, or 6-(trifluoromethyl)pyridin-3-yl.

In a particular embodiment, this invention relates to compounds of Formula (I), (II), (III), or (IV), wherein:

A represents

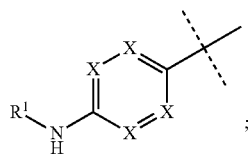

each X is independently CH or N, provided that at most two X's are N;

$R^1$ is phenyl or 5- or 6-membered heteroaryl, which is optionally substituted by —O$(C_1-C_2)$alkylO— or optionally substituted with one or two substituents independently selected from halogen, $(C_1-C_4)$alkyl, and halo$(C_1-C_4)$alkyl; and $R^3$ is $(C_1-C_4)$alkyl or halo$(C_1-C_4)$alkyl.

In another particular embodiment, this invention relates to compounds of Formula (I), (II), (III), or (IV), wherein:

A represents

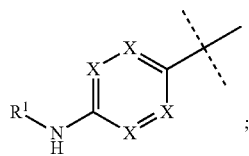

each X is independently CH or N, provided that at most two X's are N;

$R^1$ is phenyl or pyridinyl, which is optionally substituted by —O$(C_1-C_2)$alkylO— or optionally substituted with one or two substituents independently selected from halogen, $(C_1-C_4)$alkyl, and halo$(C_1-C_4)$alkyl; and $R^3$ is $(C_1-C_4)$alkyl or halo$(C_1-C_4)$alkyl.

This invention also relates to compounds that are exemplified in the Experimental section.

Specific compounds of this invention include:

2-(1-oxo-2-(2,2,2-trifluoroethyl)-6-(5-(6-(trifluoromethyl)pyridin-3-ylamino)pyridin-2-yl)-1,2,3,4-tetrahydronaphthalen-2-yl)acetic acid (enantiomer-1);

2-(6-(5-(4-chlorophenylamino)pyridin-2-yl)-1-oxo-2-(2,2,2-trifluoroethyl)-1,2,3,4-tetrahydronaphthalen-2-yl)acetic acid (enantiomer-1);

2-(2-methyl-1-oxo-6-(5-(6-(trifluoromethyl)pyridin-3-ylamino)pyridin-2-yl)-1,2,3,4-tetrahydronaphthalen-2-yl)acetic acid (enantiomer-1);

2-(2-ethyl-1-oxo-6-(5-(6-(trifluoromethyl)pyridin-3-ylamino)pyridin-2-yl)-1,2,3,4-tetrahydronaphthalen-2-yl)acetic acid (enantiomer-1);

2-(2-ethyl-1-oxo-6-(5-(6-(trifluoromethyl)pyridin-3-ylamino)pyridin-2-yl)-1,2,3,4-tetrahydronaphthalen-2-yl)acetic acid (enantiomer-2);

2-(6-(5-(4-chlorophenylamino)pyridin-2-yl)-1-oxo-2-(2,2,2-trifluoroethyl)-1,2,3,4-tetrahydronaphthalen-2-yl)acetic acid (enantiomer-2);

2-(6-(5-(5-chloropyridin-2-ylamino)pyridin-2-yl)-1-oxo-2-(2,2,2-trifluoroethyl)-1,2,3,4-tetrahydronaphthalen-2-yl)acetic acid (enantiomer-1);

2-(6-(5-(5-chloropyridin-2-ylamino)pyridin-2-yl)-1-oxo-2-(2,2,2-trifluoroethyl)-1,2,3,4-tetrahydronaphthalen-2-yl)acetic acid (enantiomer-2);

2-(1-oxo-6-(5-(p-tolylamino)pyridin-2-yl)-2-(2,2,2-trifluoroethyl)-1,2,3,4-tetrahydronaphthalen-2-yl)acetic acid (enantiomer-1);

2-(6-(5-(3,4-difluorophenylamino)pyridin-2-yl)-1-oxo-2-(2,2,2-trifluoroethyl)-1,2,3,4-tetrahydronaphthalen-2-yl)acetic acid (enantiomer-1);

2-(6-(5-(3-chlorophenylamino)pyridin-2-yl)-1-oxo-2-(2,2,2-trifluoroethyl)-1,2,3,4-tetrahydronaphthalen-2-yl)acetic acid (enantiomer-1);

2-(6-(5-(5-methylpyridin-2-ylamino)pyridin-2-yl)-1-oxo-2-(2,2,2-trifluoroethyl)-1,2,3,4-tetrahydronaphthalen-2-yl)acetic acid (enantiomer-1);

2-(6-(5-(5-methylpyridin-2-ylamino)pyridin-2-yl)-1-oxo-2-(2,2,2-trifluoroethyl)-1,2,3,4-tetrahydronaphthalen-2-yl)acetic acid (enantiomer-2);

2-(1-oxo-2-(2,2,2-trifluoroethyl)-6-(5-(6-(trifluoromethyl)pyridin-3-ylamino)pyrazin-2-yl)-1,2,3,4-tetrahydronaphthalen-2-yl)acetic acid (enantiomer-2);

2-(1-oxo-2-(2,2,2-trifluoroethyl)-6-(5-(6-(trifluoromethyl)pyridin-3-ylamino)pyrazin-2-yl)-1,2,3,4-tetrahydronaphthalen-2-yl)acetic acid (enantiomer-1);

2-(6-(5-(5-methylpyridin-2-ylamino)pyrazin-2-yl)-1-oxo-2-(2,2,2-trifluoroethyl)-1,2,3,4-tetrahydronaphthalen-2-yl)acetic acid (enantiomer-1);

2-(6-(5-(5-chloropyridin-2-ylamino)pyrazin-2-yl)-1-oxo-2-(2,2,2-trifluoroethyl)-1,2,3,4-tetrahydronaphthalen-2-yl)acetic acid (enantiomer-1);

2-(6-(5-(5-chloropyridin-2-ylamino)pyrazin-2-yl)-1-oxo-2-(2,2,2-trifluoroethyl)-1,2,3,4-tetrahydronaphthalen-2-yl)acetic acid (enantiomer-2);

2-(6-(5-(benzo[d][1,3]dioxol-5-ylamino)pyrazin-2-yl)-1-oxo-2-(2,2,2-trifluoroethyl)-1,2,3,4-tetrahydronaphthalen-2-yl)acetic acid (enantiomer-2);

2-(6-(5-(benzo[d][1,3]dioxol-5-ylamino)pyrazin-2-yl)-1-oxo-2-(2,2,2-trifluoroethyl)-1,2,3,4-tetrahydronaphthalen-2-yl)acetic acid (enantiomer-1);

2-(6-(6-(3-chlorophenylamino)pyridazin-3-yl)-1-oxo-2-(2,2,2-trifluoroethyl)-1,2,3,4-tetrahydronaphthalen-2-yl)acetic acid (enantiomer-1);

2-(6-(6-(6-methylpyridin-3-ylamino)pyridazin-3-yl)-1-oxo-2-(2,2,2-trifluoroethyl)-1,2,3,4-tetrahydronaphthalen-2-yl)acetic acid (enantiomer-1);

2-(1-oxo-2-(2,2,2-trifluoroethyl)-6-(6-(6-(trifluoromethyl)pyridin-3-ylamino)pyridazin-3-yl)-1,2,3,4-tetrahydronaphthalen-2-yl)acetic acid (enantiomer-1);

2-(1-oxo-2-(2,2,2-trifluoroethyl)-6-(6-(6-(trifluoromethyl)pyridin-3-ylamino)pyridazin-3-yl)-1,2,3,4-tetrahydronaphthalen-2-yl)acetic acid (enantiomer-2);

2-(6-(6-(5-methylthiazol-2-ylamino)pyridazin-3-yl)-1-oxo-2-(2,2,2-trifluoroethyl)-1,2,3,4-tetrahydronaphthalen-2-yl)acetic acid (enantiomer-1);

2-(6-(2-(3-chlorophenylamino)thiazol-5-yl)-1-oxo-2-(2,2,2-trifluoroethyl)-1,2,3,4-tetrahydronaphthalen-2-yl)acetic acid (enantiomer-2);

2-(1-oxo-2-(2,2,2-trifluoroethyl)-6-(2-(6-(trifluoromethyl)pyridin-3-ylamino)thiazol-5-yl)-1,2,3,4-tetrahydronaphthalen-2-yl)acetic acid (enantiomer-1); and 2-(1-oxo-2-(2,2,2-trifluoroethyl)-6-(2-(6-(trifluoromethyl)pyridin-3-ylamino)thiazol-5-yl)-1,2,3,4-tetrahydronaphthalen-2-yl)acetic acid (enantiomer-2);

or pharmaceutically acceptable salts thereof.

A person of ordinary skills in the art recognizes that compounds of the present invention may have alternative names when different naming software is used.

This invention also relates to compounds of Formula (I), (II), (III), (IV) or any of the exemplified compounds, or their pharmaceutically acceptable salts thereof, for use in therapy. In particular, for use in the treatment of diseases mediated by Acyl coenzyme A: diacylglycerol acyltransferase 1 (DGAT-1), such as obesity, obesity related disorders, genetic (Type 1, Type 5 hyperlipidemia) and acquired forms of hypertriglyceridemia or hyperlipoproteinemia-related disorders, hyperlipoproteinemia, chylomicronemia, dyslipidemia, non-alcoholic steatohepatitis, diabetes, insulin resistance, metabolic syndrome, cardiovascular outcomes, angina, excess hair growth (including syndromes associated with hirsutism), nephrotic syndrome, fibrosis such as mycocardial, renal and liver fibrosis, hepatitis C virus infection and acne or other skin disorders. In particular, this invention relates to compounds of Formula (I), (II), (III), (IV), or any of the exemplified compounds, or their pharmaceutically acceptable salts thereof, for use in the treatment of obesity.

This invention also relates to compounds of Formula (I), (II), (III), (IV) or any of the exemplified compounds, or their pharmaceutically acceptable salts thereof, for use as a medicament. This invention also relates to compounds of Formula (I), (II), (III), (IV), or any of the exemplified compounds, or their pharmaceutically acceptable salts thereof, in the manufacture of a medicament for the treatment of obesity.

Typically, but not absolutely, the salts of the present invention are pharmaceutically acceptable salts. Salts encompassed within the term "pharmaceutically acceptable salts" refer to non-toxic salts of the compounds of this invention. Salts of the disclosed compounds containing a basic amine or other basic functional group may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid or the like. Examples of pharmaceutically acceptable salts include sulfates, pyrosulfates, bisulfates, sulfites, bisulfites, phosphates, chlorides, bromides, iodides, acetates, propionates, decanoates, caprylates, acrylates, formates, isobutyrates, caproates, heptanoates, propiolates, oxalates, malonates succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, phenylacetates, phenylpropionates, phenylbutrates, citrates, lactates, γ-hydroxybutyrates, glycolates, tartrates mandelates, and sulfonates, such as xylenesulfonates, methanesulfonates, propanesulfonates, naphthalene-1-sulfonates and naphthalene-2-sulfonates.

Salts of the disclosed compounds containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, choline, quinine, quinoline, and basic amino acid such as lysine and arginine.

Other salts, which are not pharmaceutically acceptable, may be useful in the preparation of compounds of this invention and these should be considered to form a further aspect of the invention. These salts, such as oxalic or trifluoroacetate, while not in themselves pharmaceutically acceptable, may be useful in the preparation of salts useful as intermediates in obtaining the compounds of the invention and their pharmaceutically acceptable salts.

As used herein, the term "a compound of Formula (I)" or "the compound of Formula (I)" refers to one or more compounds according to Formula (I). The compound of Formula (I) may exist in solid or liquid form. In the solid state, it may exist in crystalline or noncrystalline form, or as a mixture thereof. The skilled artisan will appreciate that pharmaceutically acceptable solvates may be formed for crystalline or non-crystalline compounds. In crystalline solvates, solvent molecules are incorporated into the crystalline lattice during crystallization. Solvates may involve non-aqueous solvents such as, but not limited to, ethanol, isopropanol, DMSO, acetic acid, ethanolamine, or ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The compound of Formula (I) or a salt thereof may exist in stereoisomeric forms (e.g., it contains one or more asymmetric carbon atoms). The individual stereoisomers (enantiomers and diastereomers) and mixtures of these are included within the scope of the present invention. Likewise, it is understood that a compound or salt of Formula (I) may exist in tautomeric forms other than that shown in the formula and these are also included within the scope of the present invention. It is to be understood that the present invention includes all combinations and subsets of the particular groups defined hereinabove. The scope of the present invention includes mixtures of stereoisomers as well as purified enantiomers or enantiomerically/diastereomerically enriched mixtures. It is to be understood that the present invention includes all combinations and subsets of the particular groups defined hereinabove.

The subject invention also includes isotopically-labelled compounds, which are identical to those recited in Formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as $^{2}H$, $^{3}H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$, and $^{125}I$.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as $^{3}H$ or $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of Formula (I) and following of this invention can generally be prepared by carrying out the procedures disclosed in the Schemes and/or in the Examples below, by substituting a readily available isotopically labelled reagent for a non-isotopically labelled reagent.

DEFINITIONS

Terms are used within their accepted meanings. The following definitions are meant to clarify, but not limit, the terms defined.

As used herein, the term "alkyl" represents a saturated, straight or branched hydrocarbon moiety having the specified number of carbon atoms. The term "$(C_1-C_6)$alkyl" refers to an alkyl moiety containing from 1 to 6 carbon atoms. Exemplary alkyls include, but are not limited to methyl, ethyl, n-propyl, isopropyl, n-butyl, isobutyl, s-butyl, t-butyl, n-pentyl, isopentyl, n-hexyl and branched analogs thereof.

When the term "alkyl" is used in combination with other substituent groups, such as "halo$(C_1-C_4)$alkyl", "hydroxy$(C_1-C_4)$alkyl" or "cyano$(C_1-C_4)$alkyl", the term "alkyl" is intended to encompass a divalent straight or branched-chain hydrocarbon radical, wherein the point of attachment is through the alkyl moiety. "halo$(C_1-C_4)$alkyl" is intended to mean a radical having one or more halogen atoms, which may be the same or different, at one or more carbon atoms of an alkyl moiety containing from 1 to 4 carbon atoms, which is a straight or branched-chain carbon radical. Examples of "halo$(C_1-C_4)$alkyl" groups useful in the present invention include, but are not limited to, —$CF_3$ (trifluoromethyl), —$CCl_3$ (trichloromethyl), 1,1-difluoroethyl, 2,2,2-trifluoroethyl, and hexafluoroisopropyl. Examples of "hydroxy$(C_1-C_4)$alkyl" groups useful in the present invention include, but are not limited to, hydroxymethyl, hydroxyethyl, and hydroxyisopropyl. Examples of "cyano$(C_1-C_4)$alkyl" groups useful in the present invention include, but are not limited to, cyanomethyl, 1-cyanoethyl, 2-cyanoethyl, and 1-cyano-1-methylethyl.

"Alkoxy" refers to a group containing an alkyl radical, defined hereinabove, attached through an oxygen linking atom. The term "$(C_1-C_4)$alkoxy" refers to a straight- or branched-chain hydrocarbon radical having at least 1 and up to 4 carbon atoms attached through an oxygen linking atom. Exemplary "$(C_1-C_4)$alkoxy" groups useful in the present invention include, but are not limited to, methoxy, ethoxy, n-propoxy, isopropoxy, n-butoxy, s-butoxy, isobutoxy, and t-butoxy.

As used herein, "halogen" or "halo" refers to F, Cl, Br, or I. "Hydroxy" or "hydroxyl" is intended to mean the radical —OH. As used herein, the term "cyano" refers to the group —CN.

As used herein, "5- or 6-membered heteroaryl" represents a group or moiety comprising an aromatic monovalent monocyclic radical, containing 5 or 6 ring atoms, including at least one carbon atom and 1 to 4 heteroatoms independently selected from nitrogen, oxygen and sulfur. Selected 5-membered heteroaryl groups contain one nitrogen, oxygen, or sulfur ring heteroatom, and optionally contain 1, 2, or 3 additional nitrogen ring atoms. Selected 6-membered heteroaryl groups contain 1, 2, or 3 nitrogen ring heteroatoms. Illustrative examples of 5- or 6-membered heteroaryl groups useful in the present invention include, but are not limited to furanyl, thienyl, pyrrolyl, imidazolyl, pyrazolyl, triazolyl, tetrazolyl, oxazolyl, thiazolyl, isoxazolyl, isothiazolyl, oxadiazolyl, thiadiazolyl, pyridinyl, pyridazinyl, pyrazinyl, pyrimidinyl, and triazinyl.

As used herein, the term "optionally" means that the subsequently described event(s) may or may not occur, and includes both event(s) that occur and event(s) that do not occur.

The term "independently" means that where more than one substituent is selected from a number of possible substituents, those substituents may be the same or different. The alternative definitions for the various groups and substituent groups of Formula (I) provided throughout the specification are intended to particularly describe each compound species disclosed herein, individually, as well as groups of one or more compound species. The scope of this invention includes any combination of these group and substituent group definitions.

PHARMACEUTICAL COMPOSITIONS

The invention further provides a pharmaceutical composition (also referred to as pharmaceutical formulation) comprising a compound of Formula (I), (II), (III), or (IV) or a pharmaceutically acceptable salt thereof, and one or more excipients (also referred to as carriers and/or diluents in the pharmaceutical arts). The excipients are pharmaceutically acceptable in the sense of being compatible with the other ingredients of the formulation and not deleterious to the recipient thereof (i.e., the patient).

In accordance with another aspect of the invention there is provided a process for the preparation of a pharmaceutical composition comprising mixing (or admixing) a compound of Formula (I), (II), (III), or (IV) or a pharmaceutically acceptable salt thereof, with at least one excipient.

Pharmaceutical compositions may be in unit dose form containing a predetermined amount of active ingredient per unit dose. Such a unit may contain a therapeutically effective dose of the compound of Formula (I), (II), (III), or (IV) or a pharmaceutically acceptable salt thereof, or a fraction of a therapeutically effective dose such that multiple unit dosage forms might be administered at a given time to achieve the desired therapeutically effective dose. Preferred unit dosage formulations are those containing a daily dose or sub-dose, as herein above recited, or an appropriate fraction thereof, of an active ingredient. Furthermore, such pharmaceutical compositions may be prepared by any of the methods well-known in the pharmacy art.

Pharmaceutical compositions may be adapted for administration by any appropriate route, for example, by oral (including buccal or sublingual), rectal, nasal, topical (including buccal, sublingual, or transdermal), vaginal, or parenteral (including subcutaneous, intramuscular, intravenous, or intradermal) routes. Such compositions may be prepared by any method known in the art of pharmacy, for example, by bringing into association the active ingredient with the excipient(s).

When adapted for oral administration, pharmaceutical compositions may be in discrete units such as tablets or capsules, powders or granules, solutions or suspensions in aqueous or non-aqueous liquids, edible foams or whips, oil-in-water liquid emulsions or water-in-oil liquid emulsions. The compound or salt thereof of the invention or the pharmaceutical composition of the invention may also be incorporated into a candy, a wafer, and/or tongue tape formulation for administration as a "quick-dissolve" medicine.

For instance, for oral administration in the form of a tablet or capsule, the active drug component can be combined with an oral, non-toxic pharmaceutically acceptable inert carrier such as ethanol, glycerol, water, and the like. Powders or granules are prepared by comminuting the compound to a suitable fine size and mixing with a similarly comminuted pharmaceutical carrier such as an edible carbohydrate, as, for example, starch or mannitol. Flavoring, preservative, dispersing, and coloring agents can also be present.

Capsules are made by preparing a powder mixture, as described above, and filling formed gelatin or non-gelatinous sheaths. Glidants and lubricants such as colloidal silica, talc, magnesium stearate, calcium stearate, solid polyethylene glycol can be added to the powder mixture before the filling operation. A disintegrating or solubilizing agent such as agar-agar, calcium carbonate, or sodium carbonate can also be added to improve the availability of the medicine when the capsule is ingested.

Moreover, when desired or necessary, suitable binders, lubricants, disintegrating agents, and coloring agents can also be incorporated into the mixture. Suitable binders include starch, gelatin, natural sugars, such as glucose or beta-lactose, corn sweeteners, natural and synthetic gums such as acacia, tragacanth, sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methylcellulose, agar, bentonite, xanthan gum, and the like.

Tablets are formulated, for example, by preparing a powder mixture, granulating or slugging, adding a lubricant and disintegrant, and pressing into tablets. A powder mixture is prepared by mixing the compound, suitably comminuted, with a diluent or base as described above, and optionally, with a binder such as carboxymethylcellulose, and aliginate, gelatin, or polyvinyl pyrrolidone, a solution retardant such as paraffin, a resorption accelerator such as a quaternary salt, and/or an absorption agent such as bentonite, kaolin, or dicalcium phosphate. The powder mixture can be granulated by wetting a binder such as a syrup, starch paste, acadia mucilage, or solutions of cellulosic or polymeric materials and forcing through a screen. As an alternative to granulating, the powder mixture can be run through a tablet machine, resulting in imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compound or salt of the present invention can also be combined with a free-flowing inert carrier and compressed into tablets directly without going through the granulating or slugging steps. A clear opaque protective coating consisting of a sealing coat of shellac, a coating of sugar, or polymeric material, and a polish coating of wax can be provided. Dyestuffs can be added to these coatings to distinguish different dosages.

Oral fluids such as solutions, syrups, and elixirs can be prepared in dosage unit form so that a given quantity contains a predetermined amount of active ingredient. Syrups can be prepared by dissolving the compound or salt thereof of the invention in a suitably flavoured aqueous solution, while elixirs are prepared through the use of a non-toxic alcoholic vehicle. Suspensions can be formulated by dispersing the compound or salt of the invention in a non-toxic vehicle. Solubilizers and emulsifiers, such as ethoxylated isostearyl alcohols and polyoxyethylene sorbitol ethers, preservatives, flavor additives such as peppermint oil, natural sweeteners, saccharin, or other artificial sweeteners, and the like, can also be added.

Where appropriate, dosage unit formulations for oral administration can be microencapsulated. The formulation can also be prepared to prolong or sustain the release as, for example, by coating or embedding particulate material in polymers, wax, or the like.

In the present invention, tablets and capsules are preferred for delivery of the pharmaceutical composition.

As used herein, the term "treatment" refers to alleviating the specified condition, eliminating or reducing one or more symptoms of the condition, slowing or eliminating the progression of the condition, and preventing or delaying the reoccurrence of the condition in a previously afflicted or diagnosed patient or subject.

The present invention provides a method of treatment in a mammal, especially a human, suffering from obesity, diabetes, hypertension, depression, anxiety, drug addiction, substance addiction, or a combination thereof. Such treatment comprises the step of administering a therapeutically effective amount of a compound of Formula (I), (II), (III), or (IV) or a pharmaceutically acceptable salt thereof, to said mammal, particularly a human. Treatment can also comprise the step of administering a therapeutically effective amount of a pharmaceutical composition containing a compound of Formula (I), (II), (III), or (IV) or a pharmaceutically acceptable salt thereof, to said mammal, particularly a human.

As used herein, the term "effective amount" means that amount of a drug or pharmaceutical agent that will elicit the biological or medical response of a tissue, system, animal, or human that is being sought, for instance, by a researcher or clinician.

The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. For use in therapy, therapeutically effective amounts of a compound of Formula (I), (II), (III), or (IV), as well as salts thereof, may be administered as the raw chemical. Additionally, the active ingredient may be presented as a pharmaceutical composition. While it is possible that, for use in therapy, a therapeutically effective amount of a compound of Formula (I), (II), (III), or (IV) or a pharmaceutically acceptable salt thereof, may be administered as the raw chemical, it is typically presented as the active ingredient of a pharmaceutical composition or formulation.

The precise therapeutically effective amount of a compound or salt thereof of the invention will depend on a number of factors, including, but not limited to, the age and weight of the subject (patient) being treated, the precise disorder requiring treatment and its severity, the nature of the pharmaceutical formulation/composition, and route of administration, and will ultimately be at the discretion of the attending physician or veterinarian. Typically, a compound of Formula (I), (II), (III), or (IV) or a pharmaceutically acceptable salt thereof, will be given for the treatment in the range of about 0.1 to 100 mg/kg body weight of recipient (patient, mammal) per day and more usually in the range of 0.1 to 10 mg/kg body weight per day. Acceptable daily dosages may be from about 0.1 to about 1000 mg/day, and preferably from about 1 to about 100 mg/day. This amount may be given in a single dose per day or in a number (such as two, three, four, five, or more) of sub-doses per day such that the total daily dose is the same. An effective amount of a salt thereof may be determined as a proportion of the effective amount of the compound of Formula (I), (II), (III), or (IV) per se. Similar dosages should be appropriate for treatment of the other conditions referred herein for treatment. In general, determination of appropriate dosing can be readily arrived at by one skilled in medicine or the pharmacy art.

Additionally, the present invention provides the use of a compound of the invention in combination with weight management therapies or other triglyceride lowering therapy. In particular, the present invention provides a combination of a compound of Formula (I), (II), (III), or (IV) or a pharmaceutically acceptable salt thereof, or a pharmaceutical composition thereof with at least one other therapeutically active agent, including another anti-obesity drug and/or an anti-diabetes drug. Such other therapeutically active agent can include, for example, metformin (Glucophage®), CB1 receptor antagonists, GLP-1 agonists, opioid antagonists, and neurotransmitter reuptake inhibitors. When a compound of the invention is employed in combination with another anti-obesity drug or anti-diabetes drug, it is to be appreciated by those skilled in the art that the dose of each compound or drug of the combination may differ from that when the drug or compound is used alone. Appropriate doses will be readily appreciated and determined by those skilled in the art. The appropriate dose of the compound of Formula (I), (II), (III), or (IV) or a pharmaceutically acceptable salt thereof, and the other therapeutically active agent(s) and the relative timings of administration will be selected in order to achieve the desired combined therapeutic effect, and are within the expertise and discretion of the attending doctor or clinician.

Compounds Preparation

Generic Synthesis Schemes

The compounds of this invention may be made by a variety of methods, including well-known standard synthetic methods. Illustrative general synthetic methods are set out below and then specific compounds of the invention are prepared in the working examples. The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. In all of the schemes described below, protecting groups for sensitive or reactive groups are employed where necessary in accordance with general principles of synthetic chemistry. Protecting groups are manipulated according to standard methods of organic synthesis (T. W. Green and P. G. M. Wuts, (1991) *Protecting Groups in Organic Synthesis*, John Wiley & Sons, incorporated by reference with regard to protecting groups). These groups are removed at a convenient stage of the compound synthesis using methods that are readily apparent to those skilled in the art. The selection of processes as well as the reaction conditions and order of their execution shall be consistent with the preparation of compounds of the present invention.

The synthesis of the compounds of the general Formula (I) and pharmaceutically acceptable derivatives and salts thereof may be accomplished as outlined below in Schemes 1-4 by those skilled in the art. In the following description, the groups are as defined above for compounds of Formula (I) unless otherwise indicated. Starting materials are commercially available or are made from commercially available starting materials using methods known to those skilled in the art.

Compounds of Formula (I) may be prepared as illustrated in Scheme 1. 6-Methoxytetralone can be converted to α,β-unsaturated carboxylic acid A using glyoxalic acid followed by sulfuric acid in diglyme under heating conditions. Reduction of the olefin in the presence of reducing agents such as Zn in AcOH affords intermediate B which can be esterified to the ethyl ester with ethanol in the presence of methane sulfonic acid to provide C. Alkylation of C with an appropriately substituted alkyl halide ($R^3$—X) such as methyl iodide, ethyl iodide or trifluoroethyl iodide provides alkylated intermediate D. Demethylation of D by heating with aq. HBr reveals the masked phenol but also simultaneously hydrolyses the ethyl ester to afford acid E. Esterification of E under standard conditions provides the phenol F which is converted to the corresponding triflate G with base-catalyzed treatment using trifluoroacetic anhydride and then to the boronate ester H upon palladium-catalysed coupling with bis(pinacolato)diboron.

Boronate ester H is then coupled with an appropriate nitro aryl or heteroaryl bromide under standard Suzuki conditions to afford nitro aryl or heteroaryl intermediate I. Reduction of the nitro group is achieved using iron and ammonium chloride in aqueous ethanol at 80° C. to give the corresponding aniline J. Intermediate J can then be coupled to an aryl or a heteroaryl group under Buchwald conditions using an appropriate halide such as $R^1$—Br in the presence of reagents such as palladium dibenzylidene acetone, ligands such as BINAP and a base such as cesium carbonate in toluene at a temperature such as 80° C. to afford the corresponding disubstituted aniline K, initially as a racemic mixture. The racemate K is separated into its constituent enantiomers by HPLC using an appropriate chiral column to afford the pure R and S enantiomers as represented by the enantiomer 1a, a compound of Formula (I). Alternatively, the individual enantiomers of disubstituted aniline K, such as 1a, may be prepared by first separating racemic phenol intermediate F into its constituent enantiomers by HPLC using an appropriate chiral column to afford the pure R and S enantiomers as represented by the enantiomer F'. F' may be transformed into 1a following the same five step synthetic sequence (steps g-k in Scheme 1) employed in the conversion of racemic intermediate F into racemic disubstituted aniline K. Hydrolysis of the ester group of compound 1a with a base such as LiOH provides 1b, another compound of Formula (I).

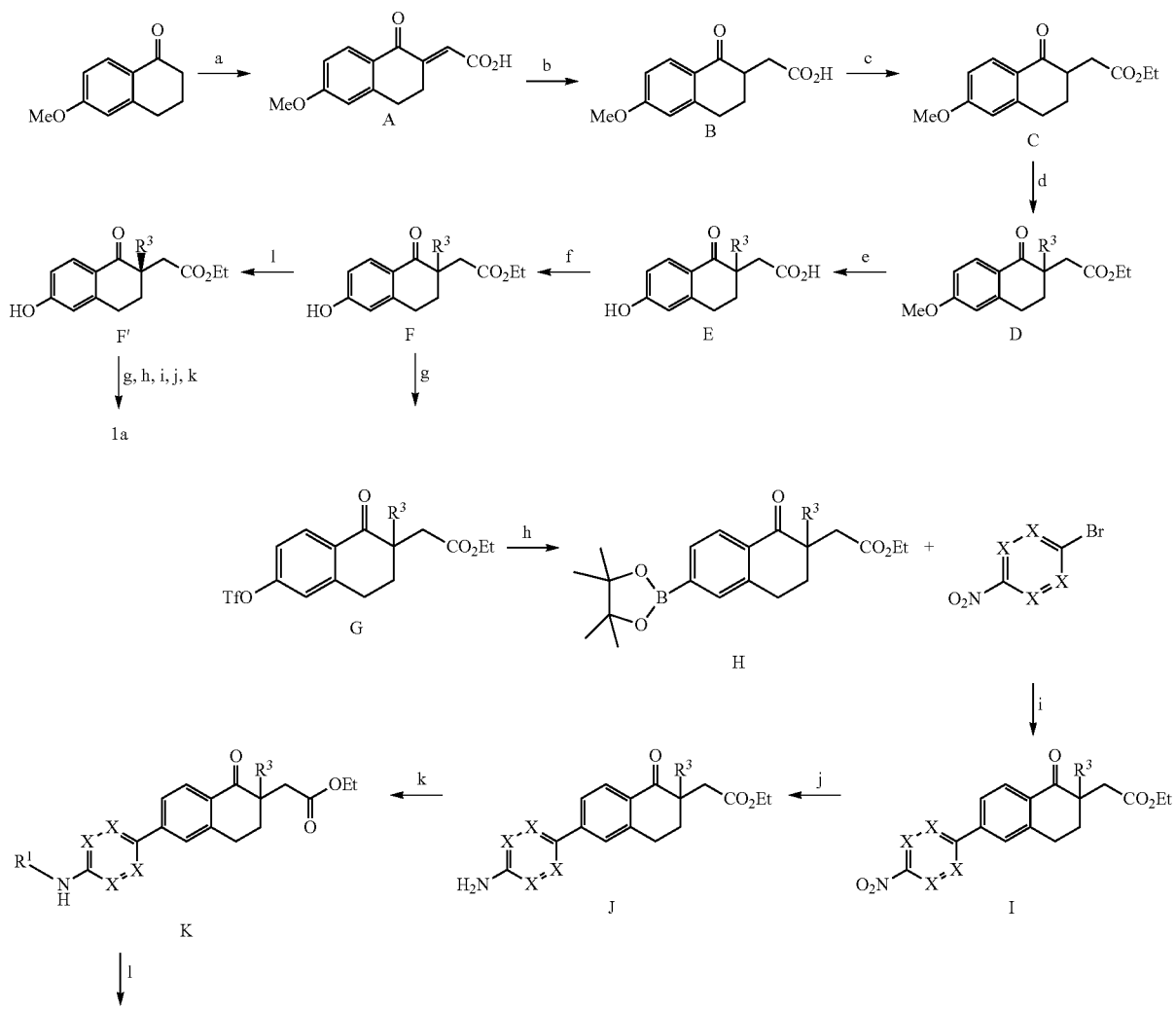

Scheme 1.

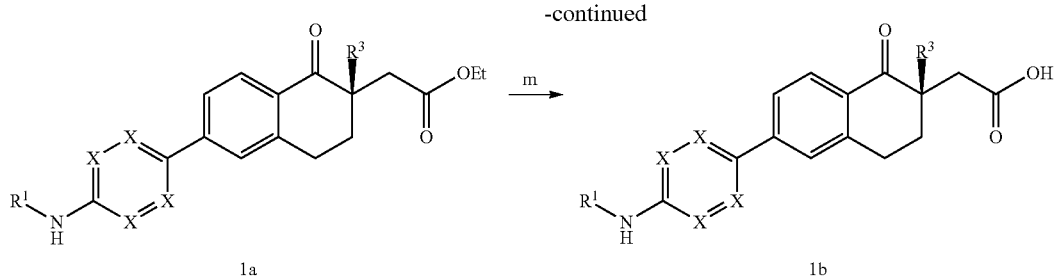

Reagents and conditions: a) glyoxalic acid, H$_2$SO$_4$, diglyme, 110° C.; b) Zn, AcOH, 100° C.; c) MeSO$_3$H, EtOH, RT; d) R$^3$—X, NaH, DMF, RT; e) Aq. HBr, 100° C.; f) MeSO$_3$H, EtOH, RT; g) Tf$_2$O, CH$_2$Cl$_2$, Py, RT; h) bis(pinacolato)diboron, PdCl$_2$(dppf), KOAc, dioxane, 80° C.; i) Pd(PPh$_3$)$_4$, Cs$_2$CO$_3$, dioxane-H$_2$O, 80° C.; j) Fe—NH$_4$Cl, EtOH—H$_2$O, 80° C.; k) R$^1$—Br, Pd$_2$(dba)$_3$, BINAP, Cs$_2$CO$_3$, toluene, 80 or 100° C.; l) Separation of racemate into its constituent enantiomers on HPLC using a chiral column; m) LiOH, EtOH—H$_2$O, RT.

Intermediate K may also be prepared as illustrated in Scheme 2. An appropriate aryl or heteroaryl amine L is reacted with a substituted aryl or heteroaryl dibromide to afford the bromoaniline M. Boronate ester H, which may be synthesized via the sequence shown in Scheme 1, can be coupled with aryl bromide M to give racemic intermediate K.

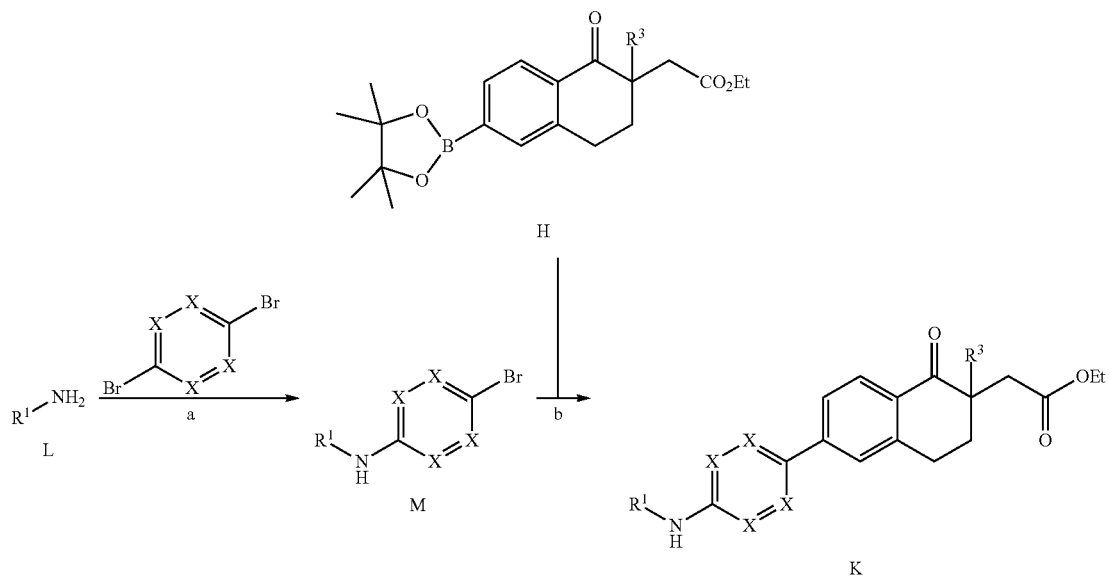

Reagents and conditions: a) Pd(OAc)$_2$, Xantphos, substituted aryl/heteroaryl dibromide, toluene, 100° C.; b) Pd(PPh$_3$)$_4$ Cs$_2$CO$_3$, dioxane-H$_2$O, 80° C..

Intermediate K may also be prepared as illustrated in Scheme 3. Boronate ester H, which may be synthesized via the sequence shown in Scheme 1, is treated with an appropriately substituted aryl or heteroaryl dibromide under palladium-catalysed Suzuki conditions in dioxane at elevated temperatures to produce bromide N. Bromide N is then treated with an appropriate aryl or heteroaryl amine (R$^1$—NH$_2$) under standard Buchwald conditions using Pd$_2$(dba)$_3$ and Xantphos to give racemic intermediate K.

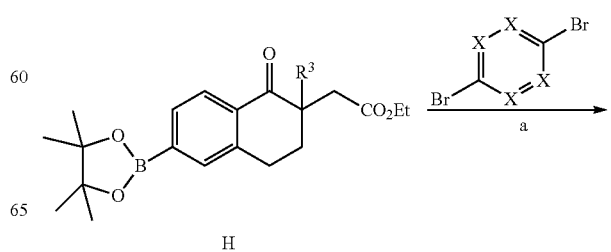

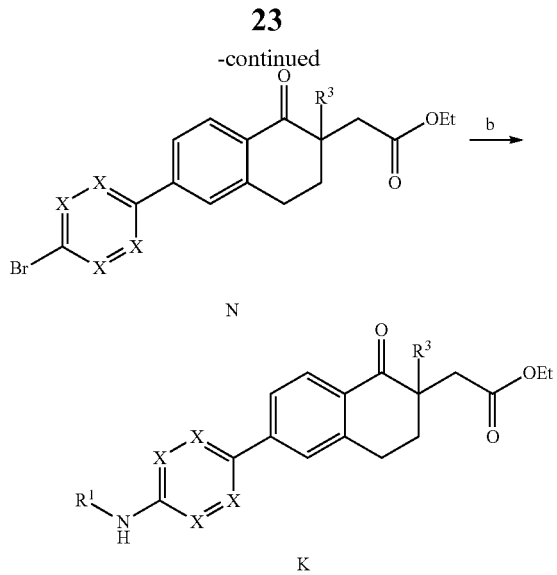

Reagents and conditions: a) PdCl₂(dppf), substituted aryl heteroaryl dibromide, Cs₂CO₃, dioxane-H₂O, 80° C.; b) R¹—NH₂, Pd₂(dba)₃, Xantphos, Cs₂CO₃, dioxane, 80° C..

Compounds of Formula (I) may also be prepared as illustrated in Scheme 4. An appropriately substituted aryl or heteroaryl isothiocyanate O is transformed to the corresponding thiourea P upon treatment with ammonia in dioxane at room temperature. Intermediate P is then treated with chloroacetaldehyde at elevated temperatures to afford the amino thiazole Q. Bromination of Q with NBS at room temperature provides the bromide R. Bromide R is then coupled with boronate ester H under palladium-catalysed conditions to give amine S as a racemic mixture. Amine S can be separated by HPLC using an appropriate chiral column to afford the pure R and S enantiomers as represented by the enantiomer 1c, a compound of Formula (I). Alternatively, enantiopure 1c can be derived from using an enantiopure boronate ester derived from phenol intermediate F' instead of the racemic boronate ester H. Hydrolysis of the ester group of compound 1c with a base such as LiOH provides 1d, another compound of Formula (I).

EXPERIMENTALS

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention. Unless otherwise noted, reagents are commercially available or are prepared according to procedures in the literature. The symbols and conventions used in the descriptions of processes, schemes, and examples are consistent with those used in the contemporary scientific literature, for example, the Journal of the American Chemical Society or the Journal of Biological Chemistry.

In the Examples:

Chemical shifts are expressed in parts per million (ppm) units. Coupling constants (J) are in units of hertz (Hz). Splitting patterns describe apparent multiplicities and are designated as s (singlet), d (doublet), t (triplet), q (quartet), dd (double doublet), dt (double triplet), dq (double quartet), m (multiplet), br (broad).

Flash column chromatography was performed on silica gel.

The naming programs used are ACDLABs 11.0 Namebatch, ACD IUPAC, or Chem Draw.

Abbreviations

Ac acetyl
AcOH acetic acid
Aq aqueous
BINAP 2,2'-bis(diphenylphosphino)-1,1'-binaphthyl
dba dibenzylidene acetone
Cs₂CO₃ cesium carbonate
DCE dichloroethane
DCM dichloromethane
DEA diethyl amine
DMF N,N-dimethylformamide Scheme 4.

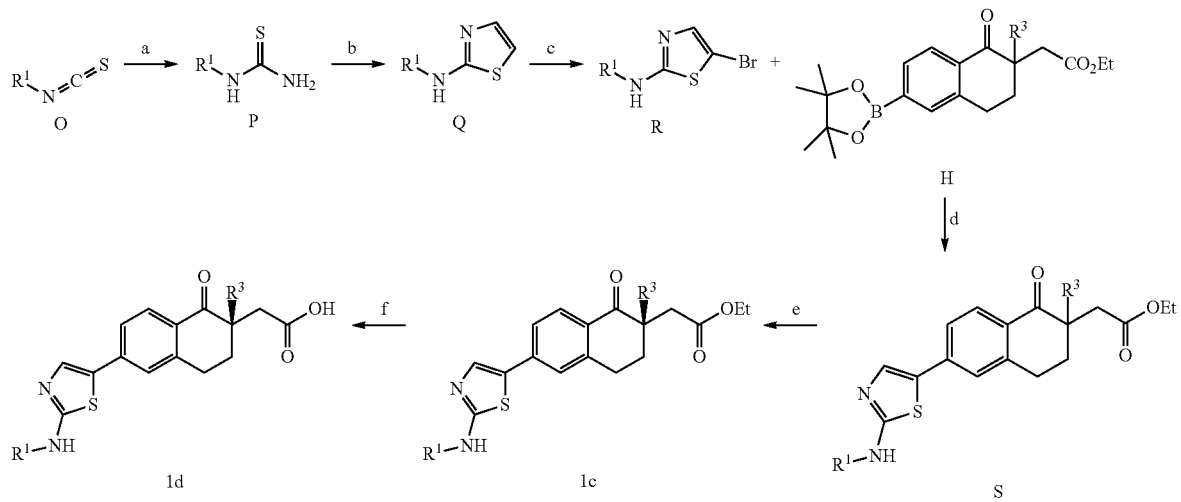

Reagents and conditions: a) 0.5 M NH₃, dioxane, RT; b) ClCH₂CHO, EtOH—H₂O, 60° C.; c) NBS, CH₂Cl₂, RT; d) PdCl₂(dppf)-CH₂Cl₂, Cs₂CO₃, Dioxane-H₂O, 80° C.; e) Separation of racemate into its constituent enantiomers on HPLC using a chiral column; f) LiOH, EtOH—H₂O, RT.

DMSO dimethyl sulfoxide
dppf 1,1'-bis(diphenylphosphino)ferrocene
ESI-MS electrospray ionization mass spectrometry
EtOH ethanol
g grams
h hours
H₂O water
H₂SO₄ sulfuric acid
HBr hydrobromic acid
HPLC high performance liquid chromatography
KOAc potassium acetate
LiOH lithium hydroxide
m/z charge to mass ratio
MeOH methanol
MeSO₃H methane sulfonic acid
MHz megahertz
min minutes
mm millimeters
mmol millimoles
NaCl sodium chloride
NaH sodium hydride
NH₄Cl ammonium chloride
NMR nuclear magnetic resonance
Pd(Cl₂)dppf [1,1'-bis(diphenylphosphino)ferrocene]dichloropalladium(II)
Pd₂(dba)₃ tris(dibenzylideneacetone)dipalladium(0)
Pd(PPh₃)₄ tetrakis(triphenylphosphine)palladium(0)
Ph phenyl
Py pyridine
RT room temperature
Rt retention time
Tf₂O trifluoroacetic anhydride
Xantphos 4,5-bis(diphenylphosphino)-9,9-dimethylxanthene
μ micron Example 1

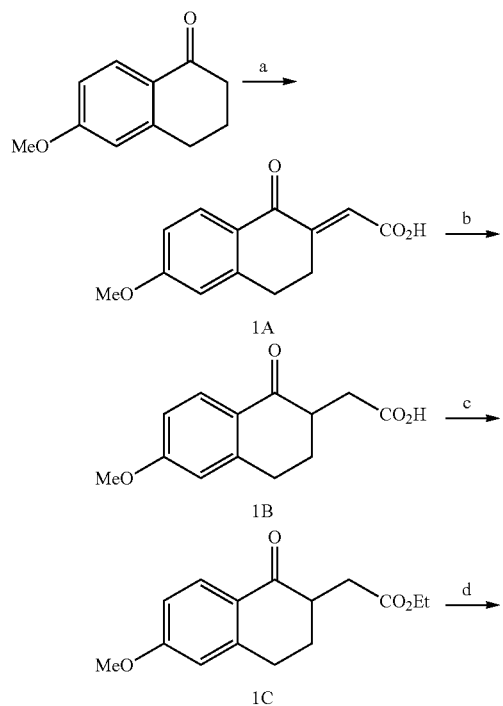

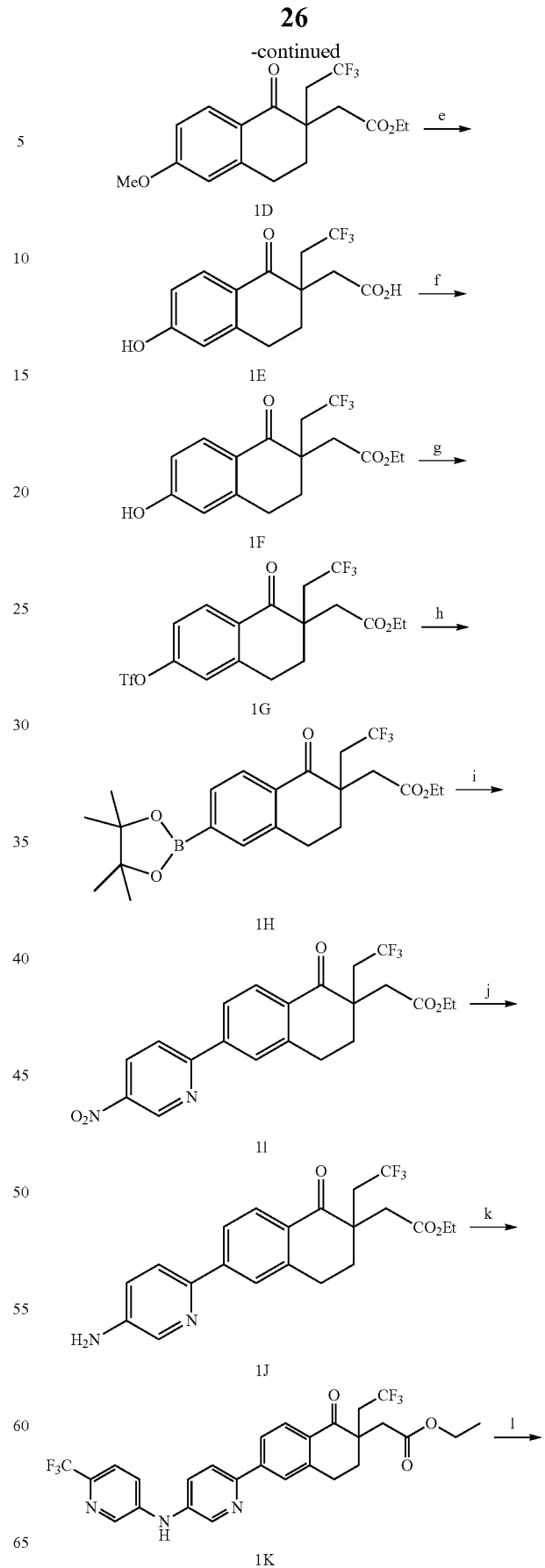

-continued

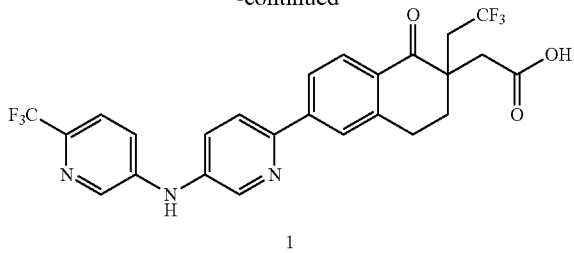

Reagents and conditions: a) glyoxalic acid, H₂SO₄, diglyme, 110° C., 12 h; b) Zn, AcOH, 100° C., 3 h; c) MeSO₃H, EtOH, 100° C., 16 h; d) CF₃CH₂I, NaH, DMF, RT, 3 h; e) Aq. HBr, 100° C., 12 h; f) MeSO₃H, EtOH, RT, 12 h; g) Tf₂O, CH₂Cl₂, Py, RT, 2 h; h) bis(pinacolato)diboron, PdCl₂(dppf), KOAc, dioxane, 80° C., 5 h; i) Pd(PPh₃)₄, Cs₂CO₃, dioxane-H₂O, 80° C., 6 h; j) Fe—NH₄Cl, EtOH—H₂O, 80° C., 3 h; k) 5-bromo-(2-trifluoromethyl)pyridine, Pd₂(dba)₃, BINAP, Cs₂CO₃, toluene, 80° C., 3 h; then chiral separation: l) LiOH, EtOH—H₂O, RT, 12 h Procedures 2-(1-Oxo-2-(2,2,2-trifluoroethyl)-6-(5-(6-(trifluoromethyl)pyridin-3-ylamino)pyridin-2-yl)-1,2,3,4-tetrahydronaphthalen-2-yl)acetic acid (enantiomer-1)

2-(6-Methoxy-1-oxo-3,4-dihydronaphthalen-2(1H)-ylidene)acetic acid (1A)

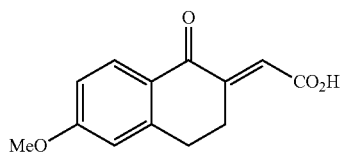

Glyoxalic acid (190 mL, 1702 mmol) and water (180 mL) were added to a stirred solution of 6-methoxy tetralone (300 g, 1702 mmol) in diglyme (600 mL) followed by sulfuric acid (80 mL, 1500 mmol). The reaction mixture was heated to 110° C. overnight. The reaction mixture was cooled to 0° C., and resulting solids were filtered off and washed with water (3×200 mL), dried under reduced pressure to afford the title compound (350 g, 88%) as a solid. ¹H NMR (300 MHz, DMSO-d₆): δ 12.9 (bs, 1H), 7.9 (d, J=8.4 Hz, 1H), 7.0 (m, 2H), 6.6 (s, 1H), 3.8 (s, 3H), 3.3 (m, 2H), 3.0 (m, 2H). ESI-MS m/z: 233 (M+H)⁺.

2-(6-Methoxy-1-oxo-1,2,3,4-tetrahydronaphthalen-2-yl)acetic acid (1B)

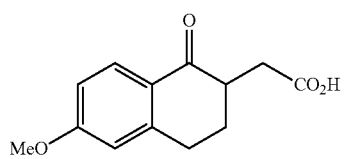

Zinc (493 g, 7536 mmol) was added to a solution of 1A (350 g, 1507 mmol) in acetic acid-water mixture (1 L+420 mL), and the mixture was stirred at 100° C. for 3 h. The reaction mixture was then filtered over celite bed, and the organic layer was removed under reduced pressure to give a residue. Water (5 L) was added to the residue. The resulting solids were filtered off and dried under vacuum to afford the title compound (280 g, 77%) as a solid. ¹H NMR (400 MHz, DMSO-d₆): δ 12.2 (bs, 1H), 7.8 (d, J=8.4 Hz, 1H), 6.9 (m, 2H), 3.8 (s, 3H), 3.1 (m, 1H), 3.0-2.8 (m, 2H), 2.7 (m, 1H), 2.4 (m, 1H), 2.2 (m, 1H), 1.9 (m, 1H). ESI-MS m/z: 235 (M+H)⁺.

Ethyl 2-(6-methoxy-1-oxo-1,2,3,4-tetrahydronaphthalen-2-yl)acetate (1C)

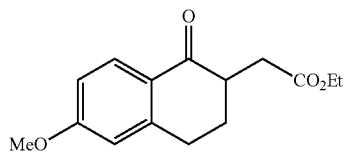

Methane sulfonic acid (450 mL) was added to a solution of 1B (250 g, 1067 mmol) in ethanol (1.5 L), and the mixture was stirred at room temperature for 16 h. Ethanol was removed from the reaction mixture under reduced pressure, and residue was diluted with ethyl acetate and extracted with brine solution. The organic layer was dried over sodium sulfate and filtered, and the filtrate was concentrated under vacuum to afford the title compound (241 g, 81%) as a solid. ¹H NMR (400 MHz, CDCl₃): δ 7.99 (d, J=8.8 Hz, 1H), 6.82 (dd, J₁=2.4 Hz, J₂=8.8 Hz, 1H), 6.68 (d, J=2.4 Hz, 1H), 4.18 (q, J=8.1 Hz, 2H), 3.8 (s, 3H), 3.12-2.85 (m, 4H), 2.39 (q, J=9.0 Hz, 1H), 2.23 (m, 1H), 1.94 (dq, J₁=4.5 Hz, J₂=12.6 Hz, 1H), 1.28 (t, J=7.5 Hz, 3H). ESI-MS m/z: 263 (M+H)⁺.

Ethyl 2-(6-methoxy-1-oxo-2-(2,2,2-trifluoroethyl)-1,2,3,4-tetrahydronaphthalen-2-yl)acetate (1D)

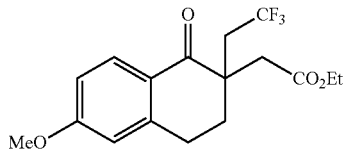

A solution of 1C (25 g, 95 mmol) in DMF (40 mL) was added over a period of 30 min to an ice cold solution of NaH (9.53 g, 238 mmol) in DMF (20 mL), and the mixture was stirred for 10 min. Trifluoroethyl iodide (50 g, 238 mmol) was then added, and the mixture was stirred for 3 h at room temperature. The reaction mixture was then brought to 0° C., excess NaH was quenched with ice water, and the aqueous layer with extracted with ethyl acetate (2×200 mL). The combined organic layers were dried over sodium sulfate and filtered, and the filtrate was concentrated under vacuum to give the title compound (16.2 g, 42%) as a solid. ¹H NMR (300 MHz, CDCl₃): δ 8.02 (d, J=9.3 Hz, 1H), 6.85 (dd, J₁=2.7 Hz, J₂=9.0 Hz, 1H), 6.68 (d, J=2.7 Hz, 1H), 4.1 (q, J=6.9 Hz, 2H), 3.86 (s, 3H), 3.05-2.9 (m, 4H), 2.6-2.4 (m, 4H), 1.23 (t, J=6.9 Hz, 3H). ESI-MS m/z: 345 (M+H)⁺.

2-(6-Hydroxy-1-oxo-2-(2,2,2-trifluoroethyl)-1,2,3,4-tetrahydronaphthalen-2-yl)acetic acid (1E)

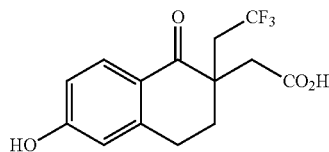

1E

Aqueous HBr (100 mL) was added to 1D (10 g, 29 mmol), and the reaction mixture was refluxed overnight. The reaction mixture was then brought to room temperature and extracted with ethyl acetate (2×100 mL). The organic layer was dried over sodium sulfate and filtered. The filtrate was removed under reduced pressure to afford crude compound (8 g) as a solid, which was carried on to the next step without further purification. $^1$H NMR (400 MHz, DMSO-$d_6$): δ 12.4 (s, 1H), 10.4 (s, 1H), 7.76 (d, J=8.0 Hz, 1H), 6.75 (dd, $J_1$=2.4 Hz, $J_2$=8.8 Hz, 1H), 6.64 (d, J=2.4 Hz, 1H), 3.0-2.85 (m, 3H), 2.73 (d, J=16.4 Hz, 1H), 2.7-2.61 (m, 1H), 2.48 (m, 1H), 2.38 (m, 1H), 2.11 (m, 1H). ESI-MS m/z: 301 (M−H)$^−$.

Ethyl 2-(6-hydroxy-1-oxo-2-(2,2,2-trifluoroethyl)-1,2,3,4-tetrahydronaphthalen-2-yl)acetate (1F)

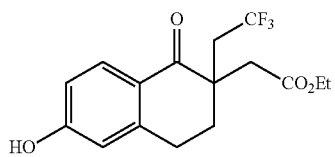

1F

Methane sulfonic acid (12 mL) was added to a solution of 1E (8 g, 26.5 mmol) in ethanol (50 mL), and the mixture was stirred at room temperature for 12 h. Ethanol was removed from reaction mixture under reduced pressure, and the residue was diluted with ethyl acetate and washed with brine solution. The organic layer was dried over sodium sulfate and filtered, and the filtrate was concentrated under reduced pressure. The crude product was purified by flash chromatography using 20% ethyl acetate in hexanes to give the title compound (6 g, 56%) as a syrup. $^1$H NMR (400 MHz, CDCl$_3$): δ 7.97 (d, J=9.2 Hz, 1H), 6.75 (dd, $J_1$=2.4 Hz, $J_2$=8.8 Hz, 1H), 6.64 (d, J=2.4 Hz, 1H), 4.1 (q, J=6.8 Hz, 2H), 3.0-2.8 (m, 4H), 2.62-2.5 (m, 2H), 2.4 (m, 1H), 2.3 (m, 1H), 1.23 (t, J=7.2 Hz, 3H). ESI-MS m/z: 331 (M+H)$^+$.

Ethyl 2-(1-oxo-2-(2,2,2-trifluoroethyl)-6-(trifluoromethylsulfonyloxy)-1,2,3,4-tetrahydronaphthalen-2-yl)acetate (1G)

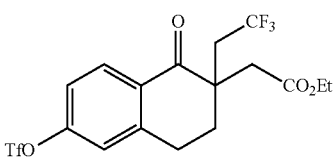

1G

Trifluoroacetic anhydride (3.68 g, 21.8 mmol) was added to an ice cold solution of 1F (6 g, 18.17 mmol) and pyridine (1.76 g, 21.8 mmol) in dichloromethane (60 mL), and the mixture was stirred at room temperature for 2 h. The reaction mixture was diluted with dichloromethane and extracted with saturated aqueous solution of NaCl (25 mL). The organic layer was dried over sodium sulfate and filtered, and the filtrate was concentrated under reduced pressure. The crude product was purified by flash chromatography using 5% ethyl acetate in hexanes to give the title compound (6 g, 71%) as a syrup. $^1$H NMR (300 MHz, CDCl$_3$): δ 8.16 (d, J=8.7 Hz, 1H), 7.28-7.18 (m, 2H), 4.13 (q, J=7.2 Hz, 2H), 3.09 (t, J=6.3 Hz, 2H), 2.96-2.72 (m, 2H), 2.66-2.45 (m, 3H), 2.34 (m, 1H), 1.24 (t, J=7.2 Hz, 3H).

Ethyl 2-(1-oxo-6-(4,4,5,5-tetramethyl-1,3,2-dioxaborolan-2-yl)-2-(2,2,2-trifluoroethyl)-1,2,3,4-tetrahydronaphthalen-2-yl)acetate (1H)

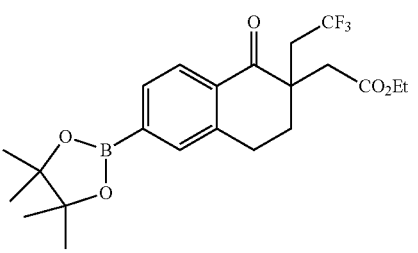

1H

PdCl$_2$(dppf)-CH$_2$Cl$_2$ adduct (0.265 g, 0.324 mmol) was added to a solution of 1G (3 g, 6.49 mmol) in 30 mL 1,4-dioxane in argon atmosphere, followed by potassium acetate (1.91 g, 19.47 mmol) and 4,4,4',4',5,5,5',5'-octamethyl-2,2'-bi(1,3,2-dioxaborolane) (1.97 g, 7.79 mmol). The mixture was degassed for 5 min. The reaction mixture was refluxed for 5 h, allowed to warm to room temperature and filtered over celite bed. The filtrate was concentrated under reduced pressure, and the residue was purified by flash chromatography using 10% ethyl acetate in hexane to afford the title compound (2.4 g, 43%) as a syrup. $^1$H NMR (400 MHz, CDCl$_3$): δ 8.02 (d, J=7.6 Hz, 1H), 7.75 (d, J=7.6 Hz, 1H), 7.70 (s, 1H), 4.11 (q, J=7.2 Hz, 2H), 3.06-3.03 (m, 2H), 2.89-2.82 (m, 2H), 2.63-2.56 (m, 2H), 2.42-2.29 (m, 2H), 1.35 (s, 12H), 1.22 (t, J=6.8 Hz, 3H). ESI-MS m/z: 441 (M+H)$^+$.

Ethyl 2-(6-(5-nitropyridin-2-yl)-1-oxo-2-(2,2,2-trifluoroethyl)-1,2,3,4-tetrahydronaphthalen-2-yl)acetate (1I)

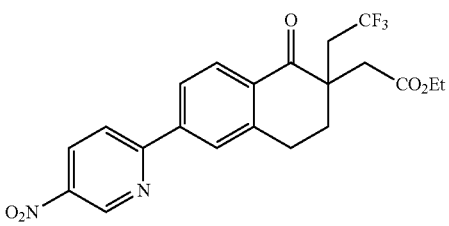

1I

Pd(PPh$_3$)$_4$ (0.315 g, 0.273 mmol) was added to a solution of 1H (2.4 g, 5.45 mmol) in 25 mL of 1,4 dioxane-H$_2$O (4:1) mixture under argon atmosphere, followed by addition of cesium carbonate (5.33 g, 16.35 mmol) and 2-bromo-5-nitro pyridine (1.328 g, 6.54 mmol). The mixture was degassed for 10 min. The reaction mixture was refluxed for 6 h, and solvent was removed under reduced pressure. The residue was partitioned between ethyl acetate and water. The separated organic layer was dried over sodium sulfate and filtered, and the filtrate was concentrated. The crude product was purified by flash chromatography using 12% ethyl acetate in hexane to afford the title compound (1.7 g, 58%) as a solid. $^1$H NMR (400 MHz, CDCl$_3$): δ 9.53 (d, J=2.6 Hz, 1H), 8.58 (dd, J$_1$=2.7 Hz, J$_2$=8.7 Hz, 1H), 8.20 (d, J=8.2 Hz, 1H), 8.07-7.94 (m, 3H), 4.14 (q, J=7.2 Hz, 2H), 3.21-3.12 (m, 2H), 2.98-2.80 (m, 2H), 2.66 (d, J=15.6 Hz, 1H), 2.71 (dd, J$_1$=4.4 Hz, J$_2$=11.2 Hz, 1H), 2.32 (m, 2H), 1.24 (t, J=7.2 Hz, 3H). ESI-MS m/z: 437 (M+H)$^+$.

Ethyl 2-(6-(5-aminopyridin-2-yl)-1-oxo-2-(2,2,2-trifluoroethyl)-1,2,3,4-tetrahydronaphthalen-2-yl)acetate (1J)

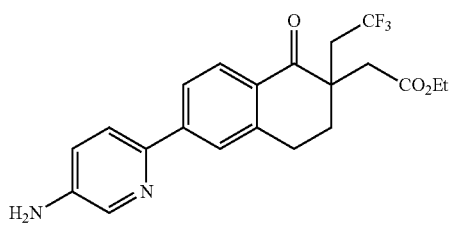

1J

Iron powder (0.218 g, 3.9 mmol) and NH$_4$Cl (0.208 g, 3.9 mmol) was added to a solution of 1I (1.7 g, 3.9 mmol) in 15 mL of ethanol-water (2:1) mixture. The reaction mixture was refluxed for 3 h, and solvent was removed under reduced pressure. The crude product was purified by flash chromatography using 25% ethyl acetate in hexane to afford the title compound (1.2 g, 53%) as a solid. $^1$H NMR (400 MHz, CDCl$_3$) δ 8.20 (d, J=2.8 Hz, 1H), 8.09 (d, J=8.2 Hz, 1H), 7.88-7.78 (m, 2H), 7.60 (d, J=8.4 Hz, 1H), 7.06 (dd, J$_1$=2.9 Hz, J$_2$=8.5 Hz, 1H), 4.13 (q, J=7.2 Hz, 2H), 3.86 (s, 2H), 3.20-3.02 (m, 2H), 2.98-2.81 (m, 2H), 2.72-2.53 (m, 2H), 2.51-2.28 (m, 2H), 1.24 (t, J=7.6 Hz, 3H). ESI-MS m/z: 407 (M+H)$^+$.

Ethyl 2-(1-oxo-2-(2,2,2-trifluoroethyl)-6-(5-(6-(trifluoromethyl)pyridin-3-ylamino)pyridin-2-yl)-1,2,3,4-tetrahydronaphthalen-2-yl)acetate (enantiomer-1) (1K1)

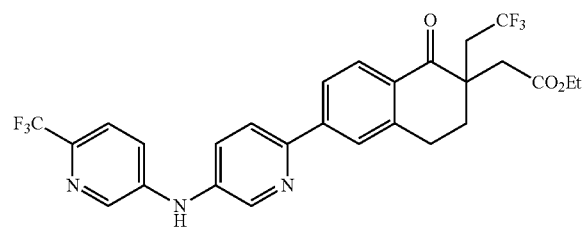

1K1

Pd$_2$(dba)$_3$ (0.158 g, 0.172 mmol) and BINAP (0.107 g, 0.172 mmol) were added to a solution of 1J (0.7 g, 1.72 mmol) in 10 mL of toluene under argon atmosphere, followed by cesium carbonate (1.68 g, 5.17 mmol) and 5-bromo-2-(trifluoromethyl)pyridine (0.389 g, 1.72 mmol). The mixture was degassed for 10 min. The reaction mixture was stirred at 80° C. for 3 h and allowed to room temperature. The reaction mixture was diluted with ethyl acetate and water. The separated organic layer was dried over sodium sulfate and filtered, and the filtrate was concentrated. The crude product was purified by flash chromatography using 25% ethyl acetate in hexane to afford racemic compound 1K (0.5 g, 51%) as a solid.

Compound 1K (0.5 g) was separated by chiral HPLC to obtain 1K1 (Rt 13.29 min) and 1K2 (Rt 16.33 min) using following conditions.

Column: CHIRAL PAK IA 4.6×250 mm, 5µ

Column ID: ANL_CHIRAL_IA 152

Mobile Phase: D=n-HEXANE (0.1% DEA), C=Ethanol; ISOCRATIC: 60:40; Flow rate: 1.0 mL/min $^1$H NMR for Compound 1K1 (400 MHz, CDCl$_3$): δ 8.77 (d, J=1.6 Hz, 1H), 8.55 (d, J=2.0 Hz, 1H), 8.17 (d, J=8.0 Hz, 1H), 7.88-7.78 (m, 4H), 7.64 (d, J=8.4 Hz, 1H), 7.58 (d, J$_1$=2.4 Hz, J$_2$=8.4 Hz, 1H), 7.19 (bs, 1H), 4.14 (q, J=7.2 Hz, 2H), 3.20-3.1 (m, 2H), 2.91-2.85 (m, 2H), 2.66 (d, J=15.6 Hz, 1H), 2.57 (m, 1H), 2.51-2.33 (m, 2H), 1.25 (t, J=7.2 Hz, 3H). ESI-MS m/z: 552 (M+H)$^+$.

2-(1-Oxo-2-(2,2,2-trifluoroethyl)-6-(5-(6-(trifluoromethyl)pyridin-3-ylamino)pyridin-2-yl)-1,2,3,4-tetrahydronaphthalen-2-yl)acetic acid (enantiomer-1) (1)

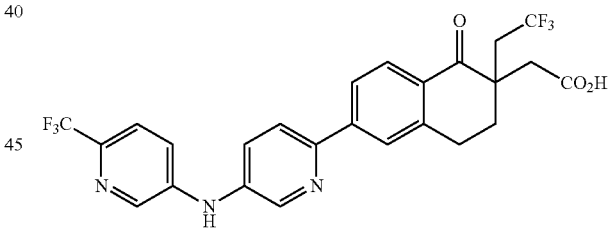

1

Lithium hydroxide (0.03 g, 1.27 mmol) was added to a solution of 1K1 (0.14 g, 0.254 mmol) in 4 mL of ethanol-water (3:1) mixture, and the reaction mixture was stirred at room temperature overnight. After the solvent was removed in vacuo, the residue was dissolved in water and washed with ethyl acetate. The aqueous layer was acidified by addition of saturated citric acid solution until pH 3 was attained. The resulting solution was cooled to 0° C., and solids obtained were filtered off and dried under vacuum to afford the title compound (0.12 g, 89%) as a white solid. $^1$H NMR (400 MHz, DMSO-d$_6$) δ 12.5 (s, 1H), 9.35 (s, 1H), 8.6 (d, J=3.2 Hz, 1H), 8.51 (s, 1H), 8.1-8.0 (m, 3H), 7.96 (d, J=8.8 Hz, 1H), 7.79 (dd, J$_1$=2.8 Hz, J$_2$=8.8 Hz, 1H), 7.75-7.69 (m, 2H), 3.14-2.96 (m, 3H), 2.81-2.74 (m, 2H), 2.54-2.4 (m, 2H), 2.16 (m, 1H). ESI-MS m/z: 524 (M+H)$^+$; HPLC purity: 98%.

Example 2

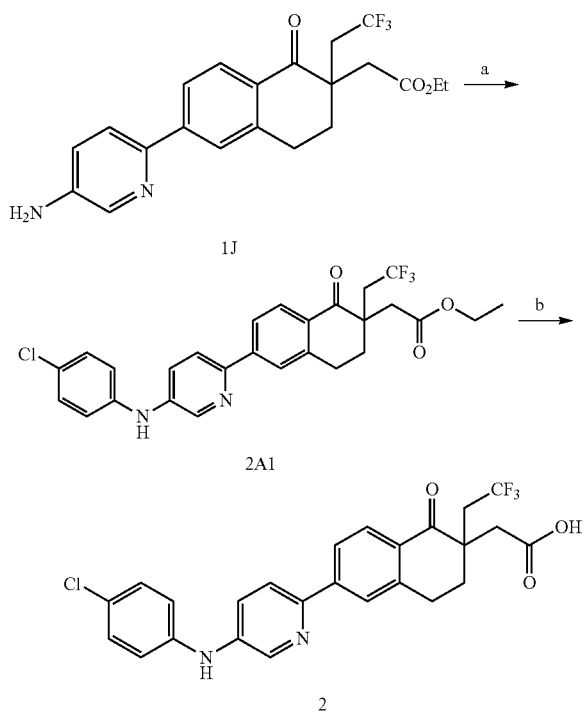

Reagents and conditions: a) 1-Bromo-4-chlorobenzene, Pd₂(dba)₃, BINAP, Cs₂CO₃, Toluene, 120° C., 5 h: then chiral separation; b) LiOH, Dioxane-H₂O, RT, 12 h.

Procedures 2-(6-(5-(4-Chlorophenylamino)pyridin-2-yl)-1-oxo-2-(2,2,2-trifluoroethyl)-1,2,3,4-tetrahydronaphthalen-2-yl)acetic acid (enantiomer-1)

Ethyl 2-(6-(5-(4-chlorophenylamino)pyridin-2-yl)-1-oxo-2-(2,2,2-trifluoroethyl)-1,2,3,4-tetrahydronaphthal-en-2-yl)acetate (enantiomer-1) (2A1)

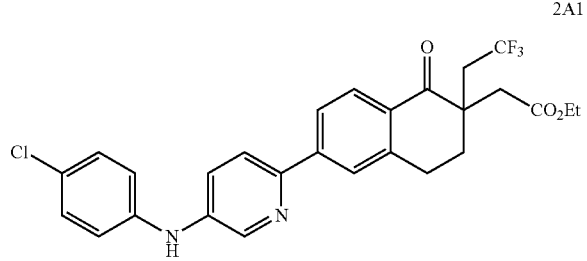 [SMILES: O=C(O)CC1(CC(F)(F)F)CCc2cc(-c3ccc(Nc4ccc(Cl)cc4)cn3)ccc2C1=O]

Pd₂(dba)₃ (0.011 g, 0.123 mmol) and BINAP (0.077 g, 0.123 mmol) were added to a solution of 1J (1 g, 2.46 mmol) in 15 mL of toluene under argon atmosphere, followed by addition of cesium carbonate (2.4 g, 7.38 mmol) and 1-bromo-4-chlorobenzene (0.471 g, 2.46 mmol). The mixture was degassed for 10 min. The reaction mixture was stirred at 120° C. for 5 h in a sealed tube and then allowed to room temperature. The reaction mixture was diluted with ethyl acetate and water. The separated organic layer was dried over sodium sulfate and filtered, and the filtrate was concentrated under reduced pressure. The crude product was purified by flash chromatography using 10% ethyl acetate in hexane to afford racemic 2A (0.8 g, 63%) as a yellow solid.

Compound 2A (0.8 g) was separated by chiral HPLC to obtain 2A1 (Rt 9.068 min) and 2A2 (Rt 10.27 min) using following conditions.

Column: CHIRAL PAK IA 4.6×250 mm, 5μ
Column ID: ANL_CHIRAL_IA 141
Mobile Phase: A=n-HEXANE (0.1% TFA), B=IPA; ISOCRATIC: 70:30; Flow rate: 1.0 mL/min $^1$H NMR for Compound 2A1 (400 MHz, CDCl₃): δ 9.0 (m, 1H), 8.20 (dd, J₁=4.4 Hz, J₂=8.3 Hz, 1H), 7.95 (d, J=8.8 Hz, 1H), 7.84 (d, J=8.8 Hz, 1H), 7.76-7.61 (m, 2H), 7.41 (d, J=8.8 Hz, 2H), 7.21 (d, J=8.8 Hz, 2H), 6.53 (s, 1H), 4.13 (q, J=7.2 Hz, 2H), 3.13 (t, J=5.6 Hz, 2H), 2.94 (d, J=16.4 Hz, 1H), 2.84 (m, 1H), 2.68 (d, J=16.4 Hz, 1H), 2.58 (m, 1H), 2.52-2.32 (m, 2H), 1.24 (t, J=7.2 Hz, 3H). ESI-MS m/z: 517 (M+H)⁺.

2-(6-(5-(4-Chlorophenylamino)pyridin-2-yl)-1-oxo-2-(2,2,2-trifluoroethyl)-1,2,3,4-tetrahydronaphthalen-2-yl)acetic acid (enantiomer-1) (2)

Lithium hydroxide (0.073 g, 1.74 mmol) was added to a solution of 2A1 (0.3 g, 0.58 mmol) in 7 mL of 1,4-dioxane-water (3:1) mixture, and the mixture was stirred at room temperature overnight. After the solvent was removed in vacuo, the residue was dissolved in water and washed with ethyl acetate. The aqueous layer was acidified by addition of saturated citric acid solution until pH 5 was attained. The resulting solution was cooled to 0° C., and solids obtained were filtered off and dried under vacuum to afford the title compound (0.2 g, 70%) as a white solid. $^1$H NMR (300 MHz, DMSO-d₆): δ 12.46 (s, 1H), 8.77 (s, 1H), 8.45 (d, J=2.7 Hz, 1H), 8.03-7.87 (m, 4H), 7.55 (dd, J₁=2.9 Hz, J₂=8.7 Hz, 1H), 7.31 (d, J=9.0 Hz, 2H), 7.14 (d, J=8.7 Hz, 2H), 3.22-2.85 (m, 3H), 2.84-2.61 (m, 2H), 2.54-2.35 (m, 2H), 2.14 (m, 1H). ESI-MS m/z: 489 (M+H)⁺; HPLC purity: 96%

Example 3

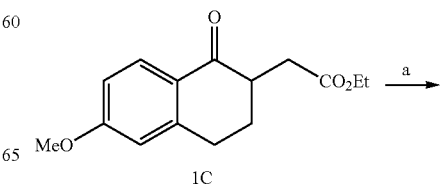

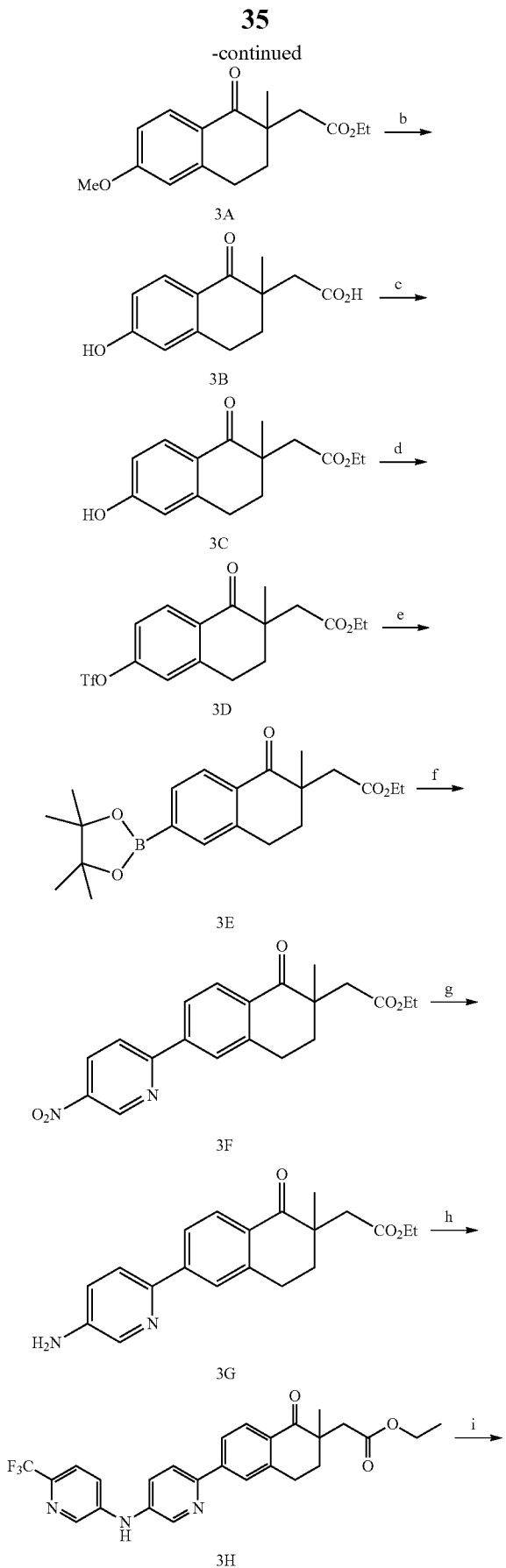
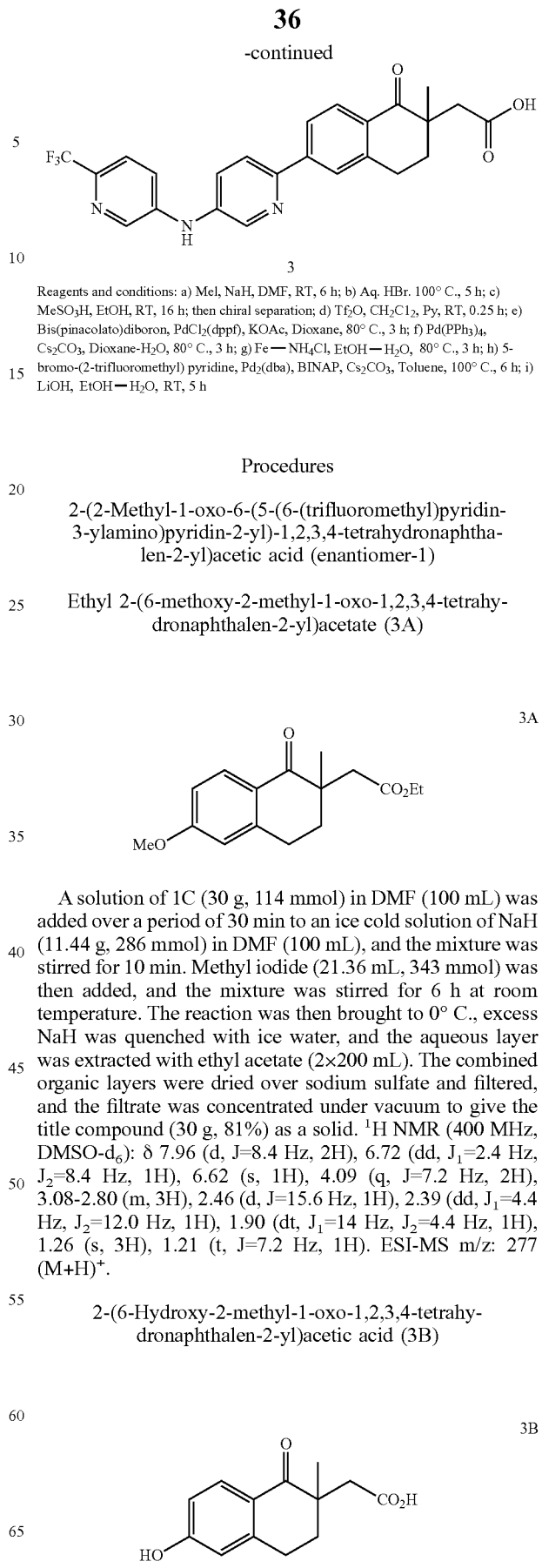

Reagents and conditions: a) MeI, NaH, DMF, RT, 6 h; b) Aq. HBr. 100° C., 5 h; c) MeSO₃H, EtOH, RT, 16 h; then chiral separation; d) Tf₂O, CH₂Cl₂, Py, RT, 0.25 h; e) Bis(pinacolato)diboron, PdCl₂(dppf), KOAc, Dioxane, 80° C., 3 h; f) Pd(PPh₃)₄, Cs₂CO₃, Dioxane-H₂O, 80° C., 3 h; g) Fe—NH₄Cl, EtOH—H₂O, 80° C., 3 h; h) 5-bromo-(2-trifluoromethyl) pyridine, Pd₂(dba), BINAP, Cs₂CO₃, Toluene, 100° C., 6 h; i) LiOH, EtOH—H₂O, RT, 5 h Procedures 2-(2-Methyl-1-oxo-6-(5-(6-(trifluoromethyl)pyridin-3-ylamino)pyridin-2-yl)-1,2,3,4-tetrahydronaphthalen-2-yl)acetic acid (enantiomer-1)

Ethyl 2-(6-methoxy-2-methyl-1-oxo-1,2,3,4-tetrahydronaphthalen-2-yl)acetate (3A)

A solution of 1C (30 g, 114 mmol) in DMF (100 mL) was added over a period of 30 min to an ice cold solution of NaH (11.44 g, 286 mmol) in DMF (100 mL), and the mixture was stirred for 10 min. Methyl iodide (21.36 mL, 343 mmol) was then added, and the mixture was stirred for 6 h at room temperature. The reaction was then brought to 0° C., excess NaH was quenched with ice water, and the aqueous layer was extracted with ethyl acetate (2×200 mL). The combined organic layers were dried over sodium sulfate and filtered, and the filtrate was concentrated under vacuum to give the title compound (30 g, 81%) as a solid. $^1$H NMR (400 MHz, DMSO-$d_6$): δ 7.96 (d, J=8.4 Hz, 2H), 6.72 (dd, $J_1$=2.4 Hz, $J_2$=8.4 Hz, 1H), 6.62 (s, 1H), 4.09 (q, J=7.2 Hz, 2H), 3.08-2.80 (m, 3H), 2.46 (d, J=15.6 Hz, 1H), 2.39 (dd, $J_1$=4.4 Hz, $J_2$=12.0 Hz, 1H), 1.90 (dt, $J_1$=14 Hz, $J_2$=4.4 Hz, 1H), 1.26 (s, 3H), 1.21 (t, J=7.2 Hz, 1H). ESI-MS m/z: 277 (M+H)$^+$.

2-(6-Hydroxy-2-methyl-1-oxo-1,2,3,4-tetrahydronaphthalen-2-yl)acetic acid (3B)

Aqueous HBr (300 mL) was added to 3A (30 g, 109 mmol), and the reaction mixture was refluxed for 5 h. The reaction mixture was then brought to room temperature, diluted with water and extracted with ethyl acetate (2×300 mL). The separated organic layers were dried over sodium sulfate and filtered, and the filtrate was concentrated under reduced pressure. The crude product was purified by flash chromatography using 40% ethyl acetate in hexanes to afford the title compound (22 g, 73%) as a solid. $^1$H NMR (400 MHz, DMSO-d$_6$): δ 12.08 (bs, 1H), 10.29 (s, 1H), 7.74 (d, J=8.4 Hz, 1H), 6.7 (m, 1H), 6.62 (m, 1H), 3.0-2.71 (m, 3H), 2.49-2.33 (m, 2H), 1.8 (m, 1H), 1.1 (s, 3H). ESI-MS m/z: 235 (M+H)$^+$.

Ethyl 2-(6-hydroxy-2-methyl-1-oxo-1,2,3,4-tetrahydronaphthalen-2-yl)acetate (entantiomer-1) (3C1)

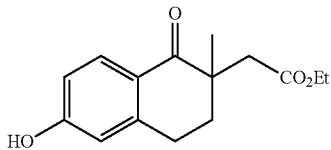

3C1

Methane sulfonic acid (30 mL) was added to a solution of 3B (22 g, 94 mmol) in ethanol (100 mL), and the mixture was stirred at room temperature for 16 h. Ethanol was removed from reaction mixture under reduced pressure, and the residue was diluted with ethyl acetate and washed with brine solution. The organic layer was dried was over sodium sulfate and filtered. Filtrate was concentrated under vacuum to afford racemic compound 3C (9 g, 36.5%) as a solid.

Compound 3C (9 g) was separated by chiral HPLC to obtain 3C1 (Rt 4.76 min) and 3C2 (Rt 5.43 min) using following conditions.

Column: CHIRAL PAK IA 4.6×250 mm, 5μ
Mobile Phase: A=n-HEXANE, B=Ethanol; ISOCRATIC: 80:20; Flow rate: 1.0 mL/min $^1$H NMR for Compound 3C1 (400 MHz, DMSO-d$_6$): δ 7.92 (d, J=9.0 Hz, 1H), 6.72 (dd, J$_1$=2.1 Hz, J$_2$=8.4 Hz, 1H), 6.63 (s, 1H), 6.2 (bs, 1H), 4.1 (q, J=6.9 Hz, 2H), 3.06-2.8 (m, 3H), 2.46 (d, J=15.6 Hz, 1H), 2.39 (dd, J$_1$=4.0 Hz, J$_2$=11.6 Hz, 1H), 1.90 (m, 1H), 1.26 (s, 3H), 1.21 (t, J=7.2 Hz, 3H). ESI-MS m/z: 263 (M+H)$^+$.

Ethyl 2-(2-methyl-1-oxo-6-(trifluoromethylsulfonyloxy)-1,2,3,4-tetrahydronaphthalen-2-yl)acetate (enantiomer-1) (3D)

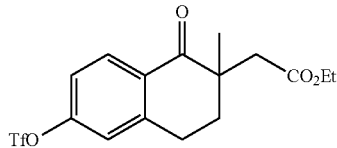

3D

Trifluoroacetic anhydride (1.12 mL, 6.63 mmol) was added to an ice cold solution of 3C1 (1.45 g, 5.53 mmol) and pyridine (0.53 mL, 6.63 mmol) in dichloromethane (15 mL), and the mixture was stirred at 10° C. for 0.25 h. The reaction mixture was diluted with dichloromethane (50 mL) and extracted with saturated aqueous solution of NaCl. The organic layer dried over sodium sulfate and filtered, and the filtrate was concentrated under reduced pressure to give the title compound (1.9 g, 86%) as a syrup. $^1$H NMR (300 MHz, CDCl$_3$): δ 8.16 (d, J=8.8 Hz, 1H), 7.2 (dd, J$_1$=2.4 Hz, J$_2$=8.8 Hz, 1H), 7.16 (s, 1H), 4.1 (q, J=7.2 Hz, 2H), 3.2-2.9 (m, 3H), 2.55-2.4 (m, 2H), 1.95 (dt, J$_1$=4.4 Hz, J$_2$=13.4 Hz, 1H), 1.27 (s, 3H), 1.21 (t, J=7.2 Hz, 3H). ESI-MS m/z: 395 (M+H)$^+$.

Ethyl 2-(2-methyl-1-oxo-6-(4,4,5,5-tetramethyl-1,3,2-dioxaborolan-2-yl)-1,2,3,4-tetrahydronaphthalen-2-yl)acetate (enantiomer-1) (3E)

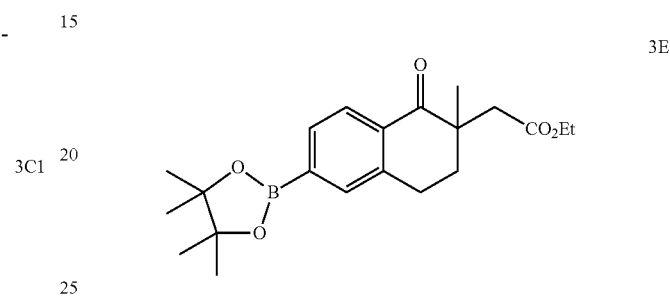

3E

PdCl$_2$(dppf)-CH$_2$Cl$_2$ adduct (0.197 g, 0.241 mmol) was added to a solution of 3D (1.9 g, 4.82 mmol) in 15 mL of 1,4-dioxane in argon atmosphere, followed by potassium acetate (0.473 g, 4.82 mmol) and 4,4,4',4',5,5,5',5'-octamethyl-2,2'-bi(1,3,2-dioxaborolane) (1.22 g, 4.82 mmol), and mixture was degassed for 5 min. The reaction mixture was refluxed for 3 h, allowed to warm to room temperature and filtered over celite bed. The filtrate was concentrated under reduced pressure, diluted with water and extracted with ethyl acetate. The organic layer was dried over sodium sulfate and filtered, and the filtrate was concentrated under reduced pressure to afford the title compound (1.6 g, 89%) as a syrup. $^1$H NMR (300 MHz, CDCl$_3$): δ 8.03 (d, J=7.9 Hz, 1H), 7.73 (d, J=8.1 Hz, 1H), 7.69 (s, 1H), 4.09 (q, J=7.5 Hz, 2H), 3.11-2.97 (m, 2H), 2.84 (d, J=15.5 Hz, 1H), 2.49 (d, J=15.5 Hz, 1H), 2.45-2.3 (m, 1H), 2.02-1.88 (m, 1H), 1.38-1.15 (m, 18H). ESI-MS m/z: 373 (M+H)$^+$.

Ethyl 2-(2-methyl-6-(5-nitropyridin-2-yl)-1-oxo-1,2,3,4-tetrahydronaphthalen-2-yl)acetate (enantiomer-1) (3F)

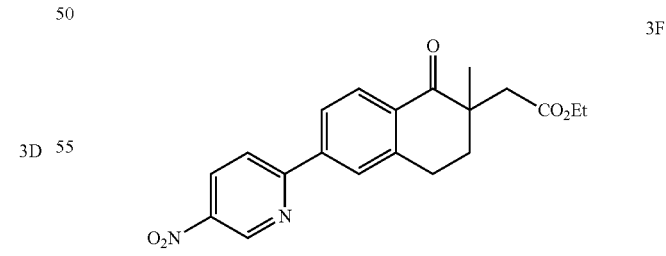

3F

Pd(PPh$_3$)$_4$ (0.248 g, 0.215 mmol) was added to a solution of 3E (1.6 g, 4.3 mmol) in 20 mL of 1,4 dioxane-H$_2$O (3:1) mixture under argon atmosphere, followed by cesium carbonate (4.2 g, 12.89 mmol) and 2-bromo-5-nitropyridine (0.872 g, 4.3 mmol). The mixture was degassed for 5 min. The reaction mixture was refluxed for 3 h, and solvent was removed under reduced pressure. The residue was partitioned between ethyl acetate and water. The separated organic layer was dried over sodium sulfate and filtered, and the filtrate was concentrated under reduced pressure. The product was purified by triturating in ethanol to afford the title compound (1.6 g, 69%) as a solid. $^1$H NMR (400 MHz, CDCl$_3$): δ 9.52 (d, J=2.6 Hz, 1H), 8.57 (dd, J$_1$=2.6 Hz, J$_2$=8.7 Hz, 1H), 8.20 (d, J=8.2 Hz, 1H), 8.02 (s, 1H), 7.97 (dd, J$_1$=3.2 Hz, J$_2$=8.0 Hz, 2H), 4.10 (q, J=7.2 Hz, 2H), 3.19 (m, 1H), 3.06 (dt, J$_1$=17.2 Hz, J$_2$=4.4 Hz, 1H), 2.98 (d, J=15.6 Hz, 1H), 2.56-2.43 (m, 2H), 2.00 (dt, J$_1$=13.5 Hz, J$_2$=4.6 Hz, 1H), 1.31 (s, 3H), 1.22 (t, J=7.2 Hz, 3H). ESI-MS m/z: 369 (M+H)$^+$.

Ethyl 2-(6-(5-aminopyridin-2-yl)-2-methyl-1-oxo-1,2,3,4-tetrahydronaphthalen-2-yl)acetate (enantiomer-1) (3G)

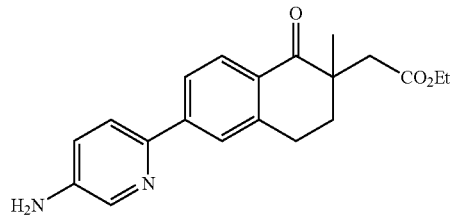

Iron powder (0.2 g, 3.58 mmol) was added to a solution of 3F (1.32 g, 3.58 mmol) in 10 mL of ethanol-water mixture (2:1) followed by NH$_4$Cl (0.192 g, 3.58 mmol), and the mixture was refluxed for 3 h. The solvent was removed under reduced pressure, and residue was partitioned between ethyl acetate and water. The separated organic layer was dried over sodium sulfate and filtered, and the filtrate was concentrated under reduced pressure. The crude product was purified by flash chromatography using 25% ethyl acetate in hexane to afford the title compound (1.01 g, 82%) as a solid. $^1$H NMR (300 MHz, DMSO-d$_6$): δ 8.05 (d, J=2.7 Hz, 1H), 7.94-7.86 (m, 3H), 7.74 (d, J=8.5 Hz, 1H), 7.00 (dd, J$_1$=2.8 Hz, J$_2$=8.6 Hz, 1H), 5.67 (s, 2H), 4.00 (q, J=7.2 Hz, 2H), 3.18-2.88 (m, 2H), 2.82 (d, J=15.8 Hz, 1H), 2.48-2.26 (m, 2H), 1.90 (dt, J$_1$=13.2 Hz, J$_2$=4.5 Hz, 1H), 1.17 (s, 3H), 1.13 (t, J=6.9 Hz, 3H). ESI-MS m/z: 339 (M+H)$^+$.

Ethyl 2-(2-methyl-1-oxo-6-(5-(6-(trifluoromethyl)pyridin-3-ylamino)pyridin-2-yl)-1,2,3,4-tetrahydronaphthalen-2-yl)acetate (enantiomer-1) (3H)

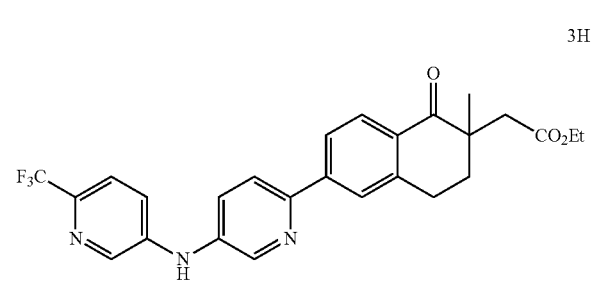 [SMILES: CCOC(=O)CC1(C)CCc2cc(-c3ccc(Nc4ccc(C(F)(F)F)nc4)cn3)ccc2C1=O]

Pd$_2$(dba)$_3$ (0.068 g, 0.074 mmol) and BINAP (0.046 g, 0.074 mmol) were added to a solution of 3G (0.5 g, 1.478 mmol) in 10 mL of toluene under argon atmosphere, followed by cesium carbonate (1.44 g, 4.43 mmol) and 5-bromo-2-(trifluoromethyl)pyridine (0.334 g, 1.478 mmol). The mixture was degassed for 10 min. The reaction mixture was stirred at 100° C. for 6 h and allowed to warm to room temperature. The reaction mixture was diluted with ethyl acetate and water. The separated organic layer was dried over sodium sulfate and filtered, and the filtrate was concentrated. The crude product was purified by flash chromatography using 8% ethyl acetate in hexane to afford the title compound 3H (0.4 g, 53%) as a solid. $^1$H NMR (300 MHz, DMSO-d$_6$): δ 9.34 (s, 1H), 8.60 (d, J=2.7 Hz, 1H), 8.51 (d, J=2.2 Hz, 1H), 8.08-7.91 (m, 4H), 7.88-7.63 (m, 3H), 4.01 (q, J=7.1 Hz, 2H), 3.08 (m, 2H), 2.85 (d, J=15.9 Hz, 1H), 2.50-2.29 (m, 2H), 1.93 (m, 1H), 1.19 (s, 3H), 1.13 (t, J=6.9 Hz, 3H). ESI-MS m/z: 484 (M+H)$^+$.

2-(2-Methyl-1-oxo-6-(5-(6-(trifluoromethyl)pyridin-3-ylamino)pyridin-2-yl)-1,2,3,4-tetrahydronaphthalen-2-yl)acetic acid (enantiomer-1) (3)

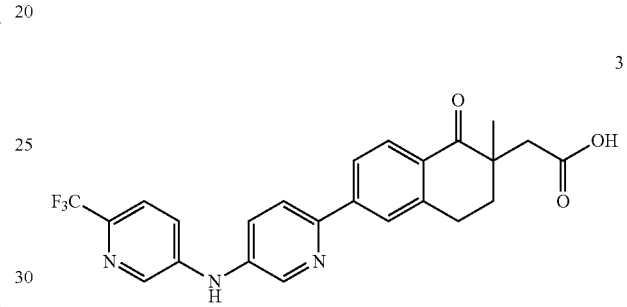

Lithium hydroxide (0.174 g, 4.14 mmol) was added to a solution of 3H (0.4 g, 0.827 mmol) in 12 mL of ethanol-water (4:1) mixture, and the mixture was stirred at room temperature for 5 h. After the solvent was removed in vacuo, the residue was dissolved in water and washed with ethyl acetate. The aqueous layer was acidified by addition of 2N aqueous solution of HCl until pH 2 was attained. The resulting solution was cooled to 0° C., and solids obtained were filtered off and dried under vacuum to afford the title compound (0.1 g, 26%) as a white solid. $^1$H NMR (300 MHz, DMSO-d$_6$): δ 12.08 (s, 1H), 9.34 (s, 1H), 8.60 (d, J=2.7 Hz, 1H), 8.51 (d, J=2.3 Hz, 1H), 8.08-7.90 (m, 4H), 7.83-7.65 (m, 3H), 3.23-2.94 (m, 2H), 2.83 (d, J=16.2 Hz, 1H), 2.48-2.36 (m, 2H), 2.02-1.85 (m, 1H), 1.17 (s, 3H). ESI-MS m/z: 456 (M+H)$^+$; HPLC Purity: 97%.

Example 4

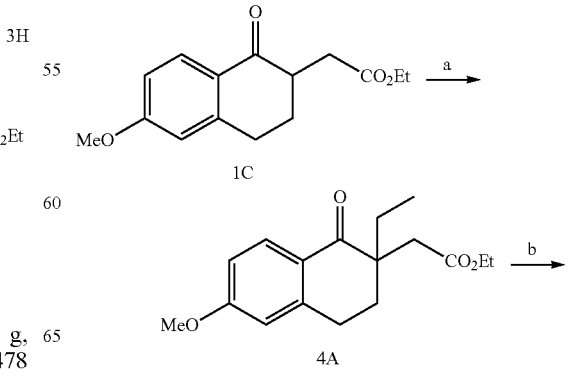

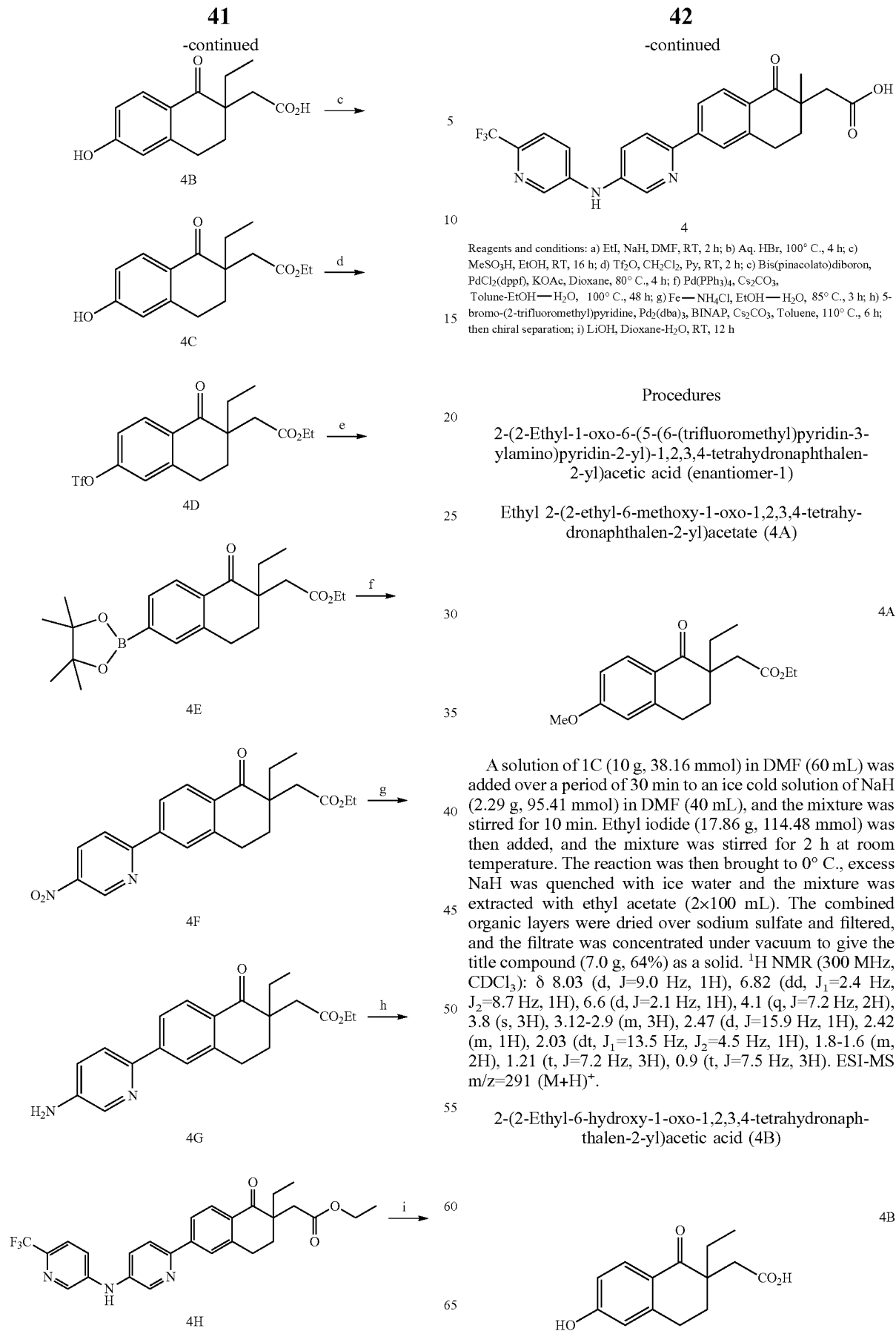

Reagents and conditions: a) EtI, NaH, DMF, RT, 2 h; b) Aq. HBr, 100° C., 4 h; c) MeSO₃H, EtOH, RT, 16 h; d) Tf₂O, CH₂Cl₂, Py, RT, 2 h; e) Bis(pinacolato)diboron, PdCl₂(dppf), KOAc, Dioxane, 80° C., 4 h; f) Pd(PPh₃)₄, Cs₂CO₃, Tolune-EtOH—H₂O, 100° C., 48 h; g) Fe—NH₄Cl, EtOH—H₂O, 85° C., 3 h; h) 5-bromo-(2-trifluoromethyl)pyridine, Pd₂(dba)₃, BINAP, Cs₂CO₃, Toluene, 110° C., 6 h; then chiral separation; i) LiOH, Dioxane-H₂O, RT, 12 h Procedures 2-(2-Ethyl-1-oxo-6-(5-(6-(trifluoromethyl)pyridin-3-ylamino)pyridin-2-yl)-1,2,3,4-tetrahydronaphthalen-2-yl)acetic acid (enantiomer-1)

Ethyl 2-(2-ethyl-6-methoxy-1-oxo-1,2,3,4-tetrahydronaphthalen-2-yl)acetate (4A)

A solution of 1C (10 g, 38.16 mmol) in DMF (60 mL) was added over a period of 30 min to an ice cold solution of NaH (2.29 g, 95.41 mmol) in DMF (40 mL), and the mixture was stirred for 10 min. Ethyl iodide (17.86 g, 114.48 mmol) was then added, and the mixture was stirred for 2 h at room temperature. The reaction was then brought to 0° C., excess NaH was quenched with ice water and the mixture was extracted with ethyl acetate (2×100 mL). The combined organic layers were dried over sodium sulfate and filtered, and the filtrate was concentrated under vacuum to give the title compound (7.0 g, 64%) as a solid. $^1$H NMR (300 MHz, CDCl₃): δ 8.03 (d, J=9.0 Hz, 1H), 6.82 (dd, $J_1$=2.4 Hz, $J_2$=8.7 Hz, 1H), 6.6 (d, J=2.1 Hz, 1H), 4.1 (q, J=7.2 Hz, 2H), 3.8 (s, 3H), 3.12-2.9 (m, 3H), 2.47 (d, J=15.9 Hz, 1H), 2.42 (m, 1H), 2.03 (dt, $J_1$=13.5 Hz, $J_2$=4.5 Hz, 1H), 1.8-1.6 (m, 2H), 1.21 (t, J=7.2 Hz, 3H), 0.9 (t, J=7.5 Hz, 3H). ESI-MS m/z=291 (M+H)⁺.

2-(2-Ethyl-6-hydroxy-1-oxo-1,2,3,4-tetrahydronaphthalen-2-yl)acetic acid (4B)

Aqueous HBr (70 mL) was added to 4A (7 g, 24.13 mmol) and the reaction mixture was refluxed for 4 h. The reaction mixture was then brought to room temperature, diluted with water and extracted with ethyl acetate (2×100 mL). The organic layers were dried over sodium sulfate and filtered, and the filtrate was concentrated under reduced pressure. The crude product was purified using flash chromatography using 40% ethyl acetate in hexanes to afford the title compound (5 g, 83.6%) as a solid. $^1$H NMR (400 MHz, DMSO-$d_6$): δ 12.0 (s, 1H), 10.3 (s, 1H), 7.8 (d, J=8.4 Hz, 1H), 6.7 (d, J=7.4 Hz, 1H), 6.6 (s, 1H), 3.0 (m, 1H), 2.7 (m, 2H), 2.4 (m, 2H), 1.9 (m, 1H), 1.7-1.5 (m, 2H), 0.9 (t, J=7.6 Hz, 3H). ESI-MS m/z=247 (M−H)$^-$.

Ethyl 2-(2-ethyl-6-hydroxy-1-oxo-1,2,3,4-tetrahydronaphthalen-2-yl)acetate (4C)

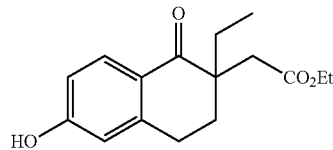

4C

Methane sulfonic acid (5 mL) was added to a solution of 4B (5 g, 20.16 mmol) in ethanol (50 mL), and the mixture was stirred at room temperature for 16 h. Ethanol was removed under reduced pressure, and the residue was diluted with ethyl acetate and washed with saturated NaCl solution. The organic layer was dried over sodium sulfate and filtered, and the filtrate was concentrated under vacuum to afford the title compound (4 g, 72%) as a solid. $^1$H NMR (300 MHz, CDCl$_3$): δ 7.92 (d, J=8.7 Hz, 1H), 6.86 (bs, 1H), 6.7 (dd, $J_1$=2.4 Hz, $J_2$=8.7 Hz, 1H), 6.61 (d, J=2.1 Hz, 1H), 4.08 (q, J=7.2 Hz, 2H), 3.1-2.9 (m, 2H), 2.77 (dt, $J_1$=16.9 Hz, $J_2$=4.5 Hz, 1H), 2.5-2.35 (m, 2H), 2.02 (dt, $J_1$=13.5 Hz, $J_2$=4.8 Hz, 1H), 1.8-1.58 (m, 2H), 1.2 (t, J=7.2 Hz, 3H), 0.9 (t, J=7.5 Hz, 3H). ESI-MS m/z=275 (M−H)$^-$.

Ethyl 2-(2-ethyl-1-oxo-6-(trifluoromethylsulfonyloxy)-1,2,3,4-tetrahydronaphthalen-2-yl)acetate (4D)

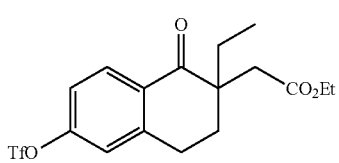

4D

Trifluoroacetic anhydride (3.67 mL, 21.71 mmol) was added to an ice cold solution of 4C (4 g, 14.48 mmol) and pyridine (1.756 mL, 21.71 mmol) in dichloromethane (50 mL), and the mixture was stirred at room temperature for 2 h. The reaction mixture was diluted with dichloromethane (100 mL) and extracted with saturated aqueous solution of NaCl (75 mL). The organic layer was dried over sodium sulfate and filtered, and the filtrate was concentrated under vacuum. The crude product was purified by flash chromatography using 5% ethyl acetate in hexanes to afford the title compound (4 g, 67.7%) as a syrup. $^1$H NMR (300 MHz, CDCl$_3$): δ 8.16 (d, J=8.7 Hz, 1H), 7.23-7.12 (m, 2H), 4.09 (q, J=7.2 Hz, 2H), 3.2-2.85 (m, 3H), 2.58-2.4 (m, 2H), 2.06 (dt, $J_1$=9.6 Hz, $J_2$=4.2 Hz, 1H), 1.8-1.55 (m, 2H), 1.21 (t, J=7.2 Hz, 3H), 0.92 (t, J=7.5 Hz, 3H). ESI-MS m/z=409 (M+H)$^+$.

Ethyl 2-(2-ethyl-1-oxo-6-(4,4,5,5-tetramethyl-1,3,2-dioxaborolan-2-yl)-1,2,3,4-tetrahydronaphthalen-2-yl)acetate (4E)

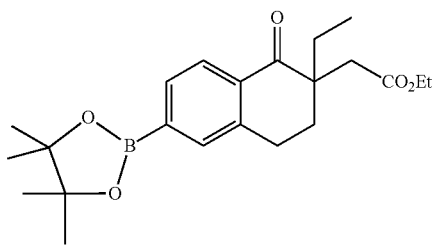

4E

PdCl$_2$(dppf)-CH$_2$Cl$_2$ adduct (0.4 g, 0.49 mmol) and dppf (0.271 g, 0.490 mmol were added to a solution of 4D (4 g, 9.79 mmol) in 120 mL of 1,4-dioxane in argon atmosphere, followed by potassium acetate (2.88 g, 29.4 mmol) and 4,4,4',4',5,5,5',5'-octamethyl-2,2'-bi(1,3,2-dioxaborolane) (2.74 g, 10.77 mmol). The mixture was degassed for 5 min. The reaction mixture was refluxed for 4 h, allowed to warm to room temperature and filtered over celite bed. The filtrate was concentrated under reduced pressure, diluted with water and extracted with ethyl acetate. The organic layer was dried over sodium sulfate and filtered, and the filtrate was concentrated under reduced pressure to afford the title compound (3.2 g, 85%) as a syrup. $^1$H NMR (300 MHz, CDCl$_3$): δ 8.02 (d, J=7.5 Hz, 1H), 7.72 (d, J=8.1 Hz, 1H), 7.67 (s, 1H), 4.08 (q, J=7.2 Hz, 2H), 3.12-2.86 (m, 3H), 2.50-2.35 (m, 2H), 2.06 (m, 1H), 1.78-1.6 (m, 2H), 1.33 (s, 12H), 1.24 (t, J=6.3 Hz, 3H), 0.85 (t, J=8.4 Hz, 3H); ESI-MS m/z=387 (M+H)$^+$.

Ethyl 2-(2-ethyl-6-(5-nitropyridin-2-yl)-1-oxo-1,2,3,4-tetrahydronaphthalen-2-yl)acetate (4F)

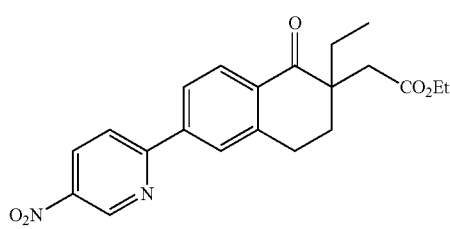

4F

Pd(PPh$_3$)$_4$ (0.479 g, 0.414 mmol) was added to a solution of 4E (3.2 g, 8.28 mmol), 2-bromo-5-nitropyridine (1.84 g, 9.11 mmol) and cesium carbonate (8.1 g, 24.85 mmol) in a mixture of ethanol (4 mL), water (4 mL) and toluene (80 mL) under argon atmosphere. The resulting mixture was degassed for further 10 min and stirred at 100° C. for 48 h. The solvent was removed under reduced pressure, and the residue was partitioned between ethyl acetate and water. The separated organic layer was treated with saturated NaCl solution, dried over sodium sulfate and filtered, and the filtrate was concentrated under reduced pressure. The crude product was triturated in ethanol to afford the title compound (2.1 g, 66%) as a solid. $^1$H NMR (300 MHz, CDCl$_3$): δ 9.52 (d, J=2.7 Hz, 1H), 8.56 (dd, J$_1$=2.1 Hz, J$_2$=8.4 Hz, 1H), 8.21 (d, J=8.4 Hz, 1H), 7.97 (m, 3H), 4.11 (q, J=7.5 Hz, 2H), 3.23-3.12 (m, 1H), 3.06-2.93 (m, 2H), 2.56-2.46 (m, 2H), 2.14-2.07 (m, 1H), 1.85-1.61 (m, 2H), 1.22 (t, J=6.9 Hz, 3H), 0.94 (t, J=7.8 Hz, 3H). ESI-MS m/z=383 (M+H).

Ethyl 2-(6-(5-aminopyridin-2-yl)-2-ethyl-1-oxo-1,2,3,4-tetrahydronaphthalen-2-yl)acetate (4G)

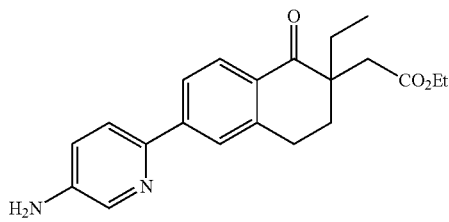

4G

Iron powder (1.533 g, 27.5 mmol) was added to a solution of 4F (2.1 g, 5.49 mmol) in 30 mL of ethanol-water mixture (5:1) followed by NH$_4$Cl (0.015 g, 0.275 mmol), and the mixture was refluxed for 5 h. The solvent was removed under reduced pressure, and residue was partitioned between ethyl acetate and water. The separated organic layer was dried over sodium sulfate, filtered, and the filtrate was concentrated in vacuo. The crude product was purified by flash chromatography using 40% ethyl acetate in hexane to afford the title compound (1.65 g, 85%) as a solid. $^1$H NMR (300 MHz, CDCl$_3$): δ 8.20 (d, J=2.7 Hz, 1H), 8.11 (d, J=7.5 Hz, 1H), 7.82 (s, 1H), 7.78 (d, J=8.4 Hz, 1H), 7.58 (d, J=8.4 Hz, 1H), 7.06 (dd, J$_1$=2.7 Hz, J$_2$=8.4 Hz, 1H), 4.11 (q, J=5.7 Hz, 2H), 3.84 (bs, 2H), 3.23-3.12 (m, 1H), 3.06-2.93 (m, 2H), 2.56-2.46 (m, 2H), 2.14-2.07 (m, 1H), 1.85-1.61 (m, 2H), 1.24 (t, J=6.9 Hz, 3H), 0.92 (t, J=7.8 Hz, 3H). ESI-MS m/z=353 (M+H).

Ethyl 2-(2-ethyl-1-oxo-6-(5-(6-(trifluoromethyl)pyridin-3-ylamino)pyridin-2-yl)-1,2,3,4-tetrahydronaphthalen-2-yl)acetate (enantiomer-1) (4H1)

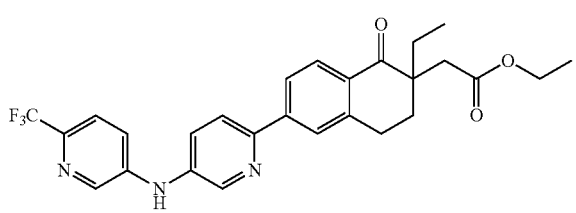

4H1

Pd$_2$(dba)$_3$ (0.377 g, 0.411 mmol) and BINAP (0.256 g, 0.411 mmol) were added to a solution of 4G (1.45 g, 4.11 mmol) in 20 mL of toluene under argon atmosphere, followed by cesium carbonate (4.02 g, 12.34 mmol) and 5-bromo-2-(trifluoromethyl)pyridine (1.023 g, 4.53 mmol). The mixture was degassed for 10 min. The reaction mixture was stirred at 110° C. for 6 h and then allowed to room temperature. The reaction mixture was diluted with ethyl acetate and water. The separated organic layer was dried over sodium sulfate and filtered, and the filtrate was concentrated under reduced pressure. The crude product was purified by flash chromatography using dichloromethane, and the resulting solid was triturated with ethanol to afford racemic 4H (0.85 g, 41%) as a solid.

Compound 4H (0.85 g) was separated by chiral HPLC to obtain 4H1 (Rt 18.33 min) and 4H2 (Rt 20.53 min) using following conditions.

Column: CHIRAL PAK IA (4.6×250 mm) 5µ

Mobile phase: A: Hexane, B: Ethanol; ISOCRATIC: 70:30; Flow rate: 1 mL/min.

$^1$H NMR for compound 4H1 (400 MHz, DMSO-d$_6$): δ 9.33 (s, 1H), 8.60 (d, J=2.4 Hz, 1H), 8.51 (d, J=1.6 Hz, 1H), 8.05-7.90 (m, 4H), 7.80-7.65 (m, 3H), 4.01 (q, J=6.8 Hz, 2H), 3.2-2.95 (m, 2H), 2.82 (d, J=16.0 Hz, 1H), 2.47 (m, 1H), 2.39 (dt, J$_1$=4.8 Hz, J$_2$=12.4 Hz, 1H), 2.01 (m, 1H), 1.75-1.50 (m, 2H), 1.14 (t, J=7.2 Hz, 3H), 0.84 (t, J=7.6 Hz, 3H). ESI-MS m/z: 498 (M+H)$^+$.

2-(2-Ethyl-1-oxo-6-(5-(6-(trifluoromethyl)pyridin-3-ylamino)pyridin-2-yl)-1,2,3,4-tetrahydronaphthalen-2-yl)acetic acid (enantiomer-1) (4)

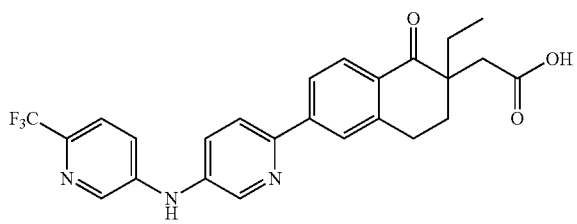

4

Lithium hydroxide (0.058 g, 2.41 mmol) was added to a solution of 4H1 (0.24 g, 0.482 mmol) in 10 mL of dioxane-water (3:1) mixture, and the mixture was stirred at room temperature overnight. After the solvent was removed in vacuo, the residue was dissolved in water and washed with ethyl acetate. The aqueous layer was acidified by addition of saturated solution of citric acid until pH 3 was attained. The resulting solution was cooled to 0° C., and solids obtained were filtered off and dried under vacuum to afford the title compound (0.2 g, 85%) as a white solid. $^1$H NMR (300 MHz, DMSO-d$_6$) δ 12.09 (bs, 1H), 9.35 (s, 1H), 8.60 (d, J=2.1 Hz, 1H), 8.51 (s, 1H), 8.07-7.84 (m, 4H), 7.83-7.60 (m, 3H), 3.20-2.89 (m, 2H), 2.78 (d, J=16.2 Hz, 1H), 2.45-2.3 (m, 2H), 1.99 (m, 1H), 1.72-1.45 (m, 2H), 0.84 (t, J=7.3 Hz, 3H). ESI-MS m/z: 470 (M+H)$^+$; HPLC purity: 96.4%.

Examples 5-13 were prepared using procedures analogous to those described in Examples 1 to 4 with appropriate starting materials.

| Ex | Structure | Analytical Data | Mass/Purity |
|---|---|---|---|
| 5 | 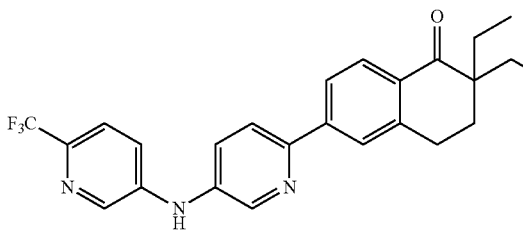<br>(enantiomer-2) | $^1$H NMR (300 MHz, DMSO-$d_6$) δ 12.07 (s, 1H), 9.34 (s, 1H), 8.60 (d, J = 2.7 Hz, 1H), 8.51 (d, J = 2.2 Hz, 1H), 8.07-7.84 (m, 4H), 7.83-7.65 (m, 3H), 3.15-2.91 (m, 2H), 2.79 (d, J = 16.3 Hz, 1H), 2.48-2.35 (m, 2H), 2.00 (m, 1H), 1.75-1.45 (m, 2H), 0.85 (t, J = 7.3 Hz, 3H). | ESI-MS m/z = 470 (M + H)$^+$; HPLC purity: 97%. |
| 6 | 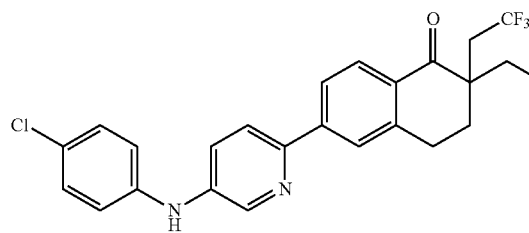<br>(enantiomer-2) | $^1$H NMR (300 MHz, DMSO-$d_6$) δ 12.34 (s, 1H), 8.77 (s, 1H), 8.45 (d, J = 2.7 Hz, 1H), 8.03-7.87 (m, 4H), 7.55 (d, $J_1$ = 8.7 Hz, $J_2$ = 2.8 Hz, 1H), 7.31 (d, J = 8.4 Hz, 2H), 7.14 (d, J = 8.7 Hz, 2H), 3.20-2.62 (m, 5H), 2.51-2.35 (m, 2H), 2.14 (m, 1H). | ESI-MS m/z = 489 (M + H)$^+$; HPLC purity: 95%. |
| 7 | 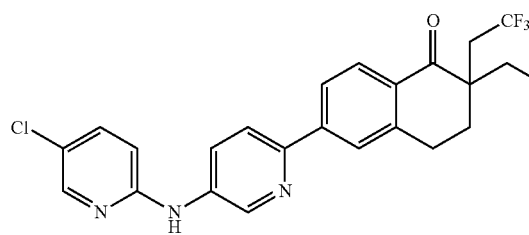<br>(enantiomer-1) | $^1$H NMR (300 MHz, DMSO-$d_6$) δ 12.2 (bs, 1H), 9.70 (s, 1H), 8.88 (d, J = 2.6 Hz, 1H), 8.35 (dd, $J_1$ = 2.7 Hz, $J_2$ = 8.8 Hz, 1H), 8.25 (d, J = 2.6 Hz, 1H), 8.08-7.90 (m, 4H), 7.73 (dd, $J_1$ = 8.9 Hz, $J_2$ = 2.7 Hz, 1H), 6.95 (d, J = 8.9 Hz, 1H), 3.19-2.73 (m, 5H), 2.49-2.33 (m, 2H), 2.16 (m, 1H). | ESI-MS m/z = 490 (M + H)$^+$; HPLC purity: 96%. |
| 8 | 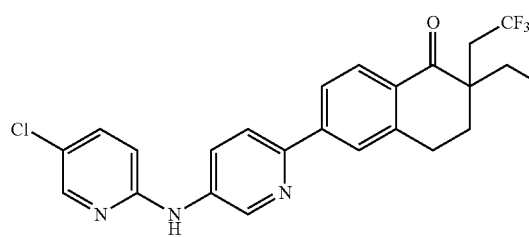<br>(enantiomer-2) | $^1$H NMR (300 MHz, DMSO-$d_6$) δ 12.38 (s, 1H), 9.70 (s, 1H), 8.88 (d, J = 2.7 Hz, 1H), 8.35 (dd, $J_1$ = 8.8 Hz, $J_2$ = 2.7 Hz, 1H), 8.25 (d, J = 2.7 Hz, 1H), 8.08-7.90 (m, 4H), 7.73 (dd, $J_1$ = 8.9 Hz, $J_2$ = 2.7 Hz, 1H), 6.95 (d, J = 8.9 Hz, 1H), 3.20-2.73 (m, 4H), 2.72-2.49 (m, 2H), 2.49-2.33 (m, 1H), 2.17 (m, 1H). | ESI-MS m/z = 490 (M + H)$^+$; HPLC purity: 99%. |
| 9 | 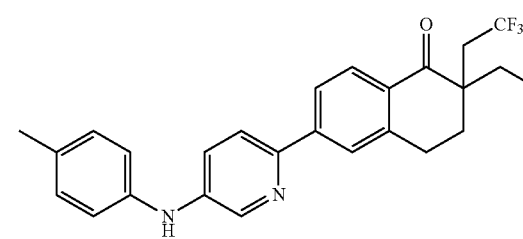<br>(enantiomer-1) | $^1$H NMR (300 MHz, DMSO-$d_6$) δ 12.4 (bs, 1H), 8.55 (s, 1H), 8.41 (d, J = 2.4 Hz, 1H), 8.03-7.85 (m, 4H), 7.48 (dd, $J_1$ = 8.7 Hz, $J_2$ = 2.8 Hz, 1H), 7.11 (q, J = 8.5 Hz, 4H), 3.17-2.68 (m, 5H), 2.49 (m, 2H), 2.27 (s, 3H), 2.14 (m, 1H). | HPLC purity: 96.3%. |

-continued

| Ex | Structure | Analytical Data | Mass/Purity |
|---|---|---|---|
| 10 | 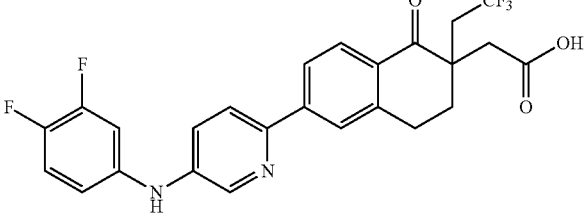(enantiomer-1) | $^1$H NMR (300 MHz, DMSO-$d_6$) δ 12.66 (s, 1H), 8.80 (s, 1H), 8.46 (d, J = 2.8 Hz, 1H), 7.97 (q, J = 8.0 Hz, 4H), 7.58 (dd, $J_1$ = 8.8 Hz, $J_2$ = 2.8 Hz, 1H), 7.35 (q, J = 9.6 Hz, 1H), 7.17 (m, 1H), 6.97 (dd, $J_1$ = 8.8 Hz, $J_2$ = 4.3 Hz, 1H), 3.17-2.66 (m, 6H), 2.43 (m, 1H), 2.15 (m, 1H). | ESI-MS m/z = 491 (M + H)$^+$; HPLC purity: 96.7%. |
| 11 | 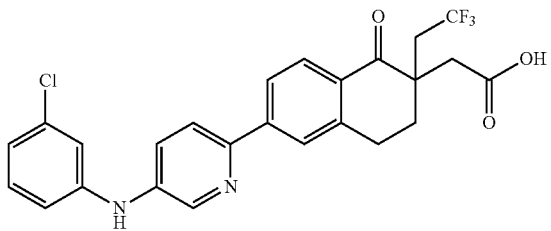 [SMILES: O=C(O)CC1(CC(F)(F)F)CCc2cc(-c3ccc(Nc4cccc(Cl)c4)cn3)ccc2C1=O](enantiomer-1) | $^1$H NMR (400 MHz, DMSO-$d_6$) δ 8.88 (s, 1H), 8.49 (d, J = 2.8 Hz, 1H), 7.97 (m, 4H), 7.62 (dd, $J_1$ = 8.7 Hz, $J_2$ = 2.8 Hz, 1H), 7.31 (t, J = 8.0 Hz, 1H), 7.21-7.08 (m, 2H), 6.94 (dd, $J_1$ = 7.9 Hz, $J_2$ = 2.0 Hz, 1H), 3.25-2.7 (m, 6H), 2.14-1.95 (m, 2H). | ESI-MS m/z = 489 (M + H)$^+$; HPLC purity: 90%. |
| 12 | 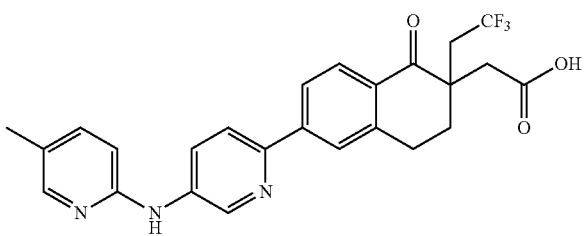 [SMILES: Cc1ccc(Nc2ccc(-c3ccc4c(c3)CCC(CC(=O)O)(CC(F)(F)F)C4=O)nc2)nc1](enantiomer-1) | $^1$H NMR (300 MHz, DMSO-$d_6$) δ 12.42 (bs, 1H), 9.39 (s, 1H), 8.88 (d, J = 2.6 Hz, 1H), 8.38 (dd, $J_1$ = 8.8 Hz, $J_2$ = 2.7 Hz, 1H), 8.11-7.89 (m, 5H), 7.49 (dd, $J_1$ = 8.4 Hz, $J_2$ = 2.4 Hz, 1H), 6.85 (d, J = 8.4 Hz, 1H), 3.12 (s, 2H), 3.07-2.91 (m, 1H), 2.77 (d, J = 15.7 Hz, 2H), 2.52-2.4 (m, 2H), 2.21 (m, 4H). | ESI-MS m/z = 470 (M + H)$^+$; HPLC purity: 97%. |
| 13 | 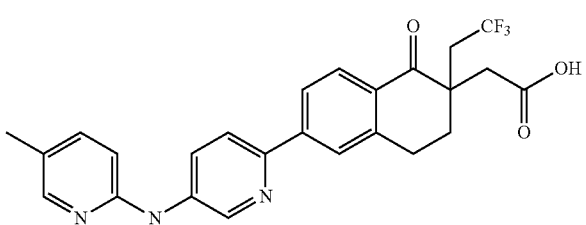(enantiomer-2) | $^1$H NMR (300 MHz, DMSO-$d_6$) δ 12.42 (bs, 1H), 9.39 (s, 1H), 8.88 (d, J = 2.6 Hz, 1H), 8.38 (dd, $J_1$ = 8.8 Hz, $J_2$ = 2.7 Hz, 1H), 8.11-7.89 (m, 5H), 7.49 (dd, $J_1$ = 8.4 Hz, $J_2$ = 2.4 Hz, 1H), 6.85 (d, J = 8.5 Hz, 1H), 3.18-2.84 (m, 3H), 2.77 (d, J = 16.1 Hz, 2H), 2.52-2.38 (m, 2H), 2.21 (m, 4H). | ESI-MS m/z = 470 (M + H)$^+$; HPLC purity: 90%. |

Example 14

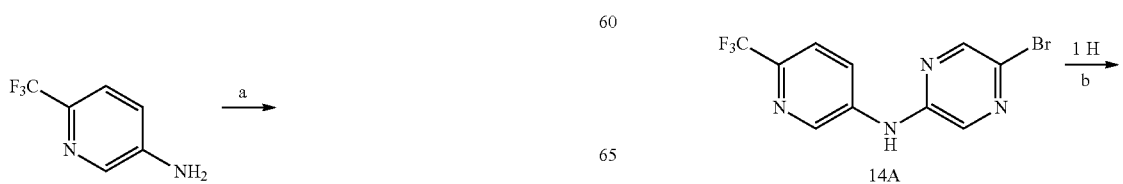

-continued

-continued

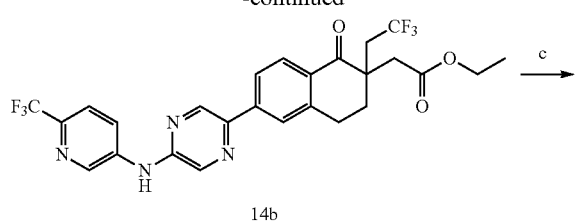

14b

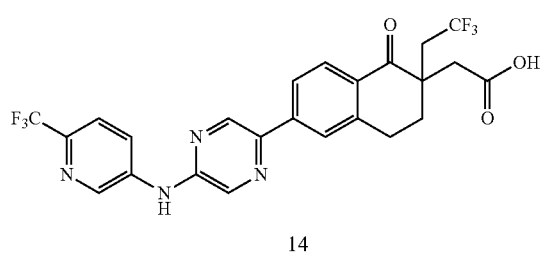

14

Reagents and conditions: a) Pd(OAc)₂, Xantphos, 2,5-dibromopyrazine, Toluene, 100° C., 4 h; b) Pd(PPh₃)₄, Cs₂CO₃, Dioxane-H₂O, 80° C., 3 h; then chiral separation; c) LiOH, EtOH—H₂O, RT, 5 h.

Procedures 2-(1-Oxo-2-(2,2,2-trifluoroethyl)-6-(5-(6-(trifluoromethyl)pyridin-3-ylamino)pyrazin-2-yl)-1,2,3,4-tetrahydro-naphthalen-2-yl)acetic acid (enantiomer-2)

5-Bromo-N-(6-(trifluoromethyl)pyridin-3-yl)pyrazin-2-amine (14A)

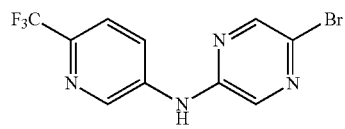

14A

Pd(OAc)₂ (0.097 g, 0.432 mmol) and Xantphos (0.25 g, 0.432 mmol) were added to a solution of 2,5-dibromopyrazine (2.05 g, 8.64 mmol) in 15 mL of toluene under argon atmosphere, followed by cesium carbonate (8.44 g, 25.9 mmol) and 6-(trifluoromethyl)pyridin-3-amine (1.4 g, 8.64 mmol). The mixture was degassed for 10 min. The reaction mixture was stirred at 100° C. for 4 h, allowed to warm to room temperature, and diluted with ethyl acetate and water. The separated organic layer was dried over sodium sulfate and filtered, and the filtrate was concentrated under reduced pressure. The crude product was purified by flash chromatography using 20% ethyl acetate in hexane to afford the title compound (1 g, 36%) as a white solid. ¹H NMR (300 MHz, DMSO-d₆) δ 10.34 (s, 1H), 8.88 (d, J=2.5 Hz, 1H), 8.47-8.35 (m, 2H), 8.17 (d, J=1.4 Hz, 1H), 7.84 (d, J=8.7 Hz, 1H). ESI-MS m/z: 319 (M+H)⁺.

Ethyl 2-(1-oxo-2-(2,2,2-trifluoroethyl)-6-(5-(6-(trifluoromethyl)pyridin-3-ylamino)pyrazin-2-yl)-1,2,3,4-tetrahydronaphthalen-2-yl)acetate (enantiomer-2) (14B2)

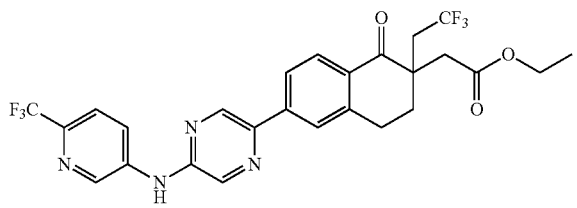

14B2

Pd(PPh₃)₄ (0.131 g, 0.114 mmol) was added to a solution of 1H (1 g, 2.27 mmol) in 16 mL of 1,4 dioxane-H₂O (3:1) mixture under argon atmosphere, followed by 14A (0.725 g, 2.27 mmol) and cesium carbonate (2.22 g, 6.81 mmol). The mixture was degassed for 15 min. The reaction mixture was refluxed for 3 h, and solvent was removed under reduced pressure. The residue was partitioned between ethyl acetate and water. The separated organic layer was dried over sodium sulfate and filtered, and the filtrate was concentrated under reduced pressure. The crude product was purified by flash chromatography using 20% ethyl acetate in hexane to afford racemic compound 14B (0.8 g, 54%) as a yellow solid.

Compound 14B (0.8 g) was separated by chiral HPLC to obtain 14B1 (Rt 7.96 min) and 14B2 (Rt 9.40 min) using following conditions.

Column: CHIRAL PAK IC (4.6×250 mm), 5μ
Mobile Phase: A=n-HEXANE, B=IPA, C=DCM; ISOCRATIC: 60:20:20; Flow rate: 1.0 mL/min ¹H NMR for Compound 14B2 (400 MHz, DMSO-d₆) δ 10.45 (s, 1H), 8.98 (dd, J₁=2.0 Hz, J₂=9.1 Hz, 2H), 8.53 (dd, J₁=2.5 Hz, J₂=8.7 Hz, 1H), 8.46 (d, J=1.4 Hz, 1H), 8.08-8.02 (m, 2H), 7.98 (d, J=8.8 Hz, 1H), 7.88 (d, J=8.8 Hz, 1H), 4.04 (q, J=7.2 Hz, 2H), 3.25-3.03 (m, 2H), 3.04-2.94 (m, 1H), 2.90 (d, J=16.0 Hz, 1H), 2.82-2.64 (m, 2H), 2.41 (m, 1H), 2.19 (m, 1H), 1.15 (t, J=6.8 Hz, 3H). ESI-MS m/z: 551 (M−H)⁻.

2-(1-Oxo-2-(2,2,2-trifluoroethyl)-6-(5-(6-(trifluoromethyl)pyridin-3-ylamino)pyrazin-2-yl)-1,2,3,4-tetrahydro-naphthalen-2-yl)acetic acid (enantiomer-2) (14)

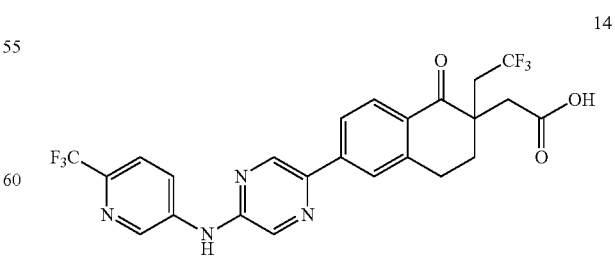

14

Lithium hydroxide (0.114 g, 2.72 mmol) was added to a solution of 14B2 (0.3 g, 0.543 mmol) in 6 mL of ethanol-water (3:1) mixture, and the mixture was stirred at room temperature for 5 h. After the solvent was removed in vacuo, the residue was diluted with water. The aqueous layer was acidified with addition of saturated citric acid solution until pH 3 was attained. The resulting solution was cooled to 0° C., and solids obtained were filtered off and dried under vacuum to afford the title compound (0.2 g, 88%) as a solid. $^1$H NMR (300 MHz, DMSO-d$_6$) δ 12.47 (s, 1H), 10.47 (s, 1H), 8.98 (dd, $J_1$=1.9 Hz, $J_2$=7.7 Hz, 2H), 8.53 (dd, $J_1$=2.1 Hz, $J_2$=8.7 Hz, 1H), 8.46 (s, 1H), 8.10-7.93 (m, 3H), 7.88 (d, J=8.7 Hz, 1H), 3.26-2.92 (m, 3H), 2.88-2.64 (m, 2H), 2.58-2.42 (m, 2H), 2.17 (m, 1H). ESI-MS m/z: 525 (M+H)$^+$; HPLC purity: 97%.

Examples 15-20 were prepared using procedures analogous to those described in Example 14 with appropriate starting materials.

| Ex | Structure | Analytical Data | Mass/Purity |
|---|---|---|---|
| 15 | (enantiomer-1) | $^1$H NMR (400 MHz, DMSO-d$_6$) δ 12.46 (s, 1H), 10.47 (s, 1H), 8.99 (d, J = 2.4 Hz, 1H), 8.96 (s, 1H), 8.53 (dd, $J_1$ = 2.4 Hz, $J_2$ = 8.8 Hz, 1H), 8.47 (s, 1H), 8.10-7.95 (m, 3H), 7.88 (d, J = 8.8 Hz, 1H), 3.26-2.92 (m, 3H), 2.83 (d, J = 16.8 Hz, 1H), 2.70-2.65 (m, 1H), 2.58 (d, J = 16.0 Hz, 1H), 2.46 (m, 1H), 2.18 (m, 1H). | ESI-MS m/z = 525 (M + H)$^+$; HPLC purity: 95.5%. |
| 16 | (enantiomer-1) | $^1$H NMR (400 MHz, DMSO-d$_6$) δ 12.4 (bs, 1H), 10.21 (s, 1H), 9.11 (s, 1H), 8.93 (s, 1H), 8.15 (s, 1H), 8.09-8.02 (m, 2H), 7.96 (d, J = 8.8 Hz, 1H), 7.68 (d, J = 8.4 Hz, 1H), 7.59 (d, J = 8.0 Hz, 1H), 3.23-2.90 (m, 3H), 2.83 (d, J = 16.0 Hz, 1H), 2.76-2.55 (m, 3H), 2.25 (s, 3H), 2.18 (m, 1H). | ESI-MS m/z = 471 (M + H)$^+$; HPLC purity: 99%. |
| 17 | (enantiomer-1) | $^1$H NMR (300 MHz, DMSO-d$_6$) δ 12.42 (bs, 1H), 10.47 (bs, 1H), 9.06 (s, 1H), 8.93 (s, 1H), 8.32 (d, J = 2.4 Hz, 1H), 8.06-7.74 (m, 5H), 3.15-2.77 (m, 4H), 2.68 (d, J = 15.6 Hz, 1H), 2.42-2.3 (m, 2H), 2.11 (m, 1H). | ESI-MS m/z = 491 (M + H)$^+$; HPLC purity: 90%. |
| 18 | (enantiomer-2) | $^1$H NMR (400 MHz, DMSO-d$_6$) δ 12.43 (bs, 1H), 10.50 (s, 1H), 9.09 (s, 1H), 8.97 (s, 1H), 8.35 (d, J = 2.6 Hz, 1H), 8.09-8.02 (m, 2H), 7.97 (d, J = 8.8 Hz, 1H), 7.91-7.79 (m, 2H), 3.23-2.90 (m, 3H), 2.82 (d, J = 16.5 Hz, 1H), 2.76-2.44 (m, 3H), 2.18 (m, 1H). | ESI-MS m/z = 491 (M + H)$^+$; HPLC purity: 96%. |
| 19 | (enantiomer-2) | $^1$H NMR (300 MHz, DMSO-d$_6$) δ 12.2 (bs, 1H), 9.69 (s, 1H), 8.81 (s, 1H), 8.27 (s, 1H), 8.05-7.92 (m, 3H), 7.48 (d, J = 2.1 Hz, 1H), 7.10 (d, J = 8.2 Hz, 1H), 6.90 (d, J = 8.4 Hz, 1H), 6.00 (s, 2H), 3.20-2.86 (m, 4H), 2.82-2.54 (m, 3H), 2.17 (m, 1H). | ESI-MS m/z = 500 (M + H)$^+$; HPLC purity: 95%. |

| Ex | Structure | Analytical Data | Mass/Purity |
|---|---|---|---|
| 20 | 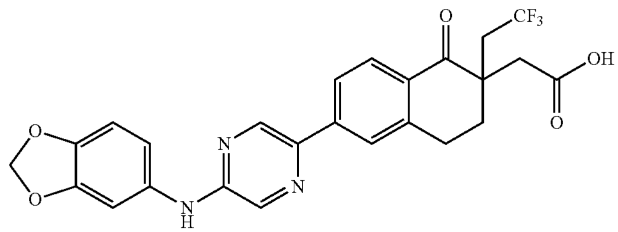 [SMILES: O=C(O)CC1(CC(F)(F)F)CCc2cc(-c3cnc(Nc4ccc5c(c4)OCO5)cn3)ccc2C1=O] | $^1$H NMR (300 MHz, DMSO-$d_6$) δ 12.2 (bs, 1H), 9.68 (s, 1H), 8.81 (d, J = 1.4 Hz, 1H), 8.27 (d, J = 1.4 Hz, 1H), 8.04-7.89 (m, 3H), 7.48 (d, J = 2.1 Hz, 1H), 7.09 (dd, J$_1$ = 2.1 Hz, J$_2$ = 8.4 Hz, 1H), 6.90 (d, J = 8.4 Hz, 1H), 6.00 (s, 2H), 3.18-2.87 (m, 3H), 2.86-2.67 (m, 2H), 2.56-2.43 (m, 2H), 2.16 (m, 1H). | ESI-MS m/z = 500 (M + H)$^+$; HPLC purity: 93%. |

Example 21

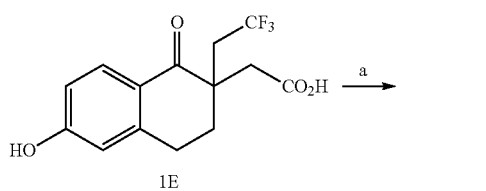

1E

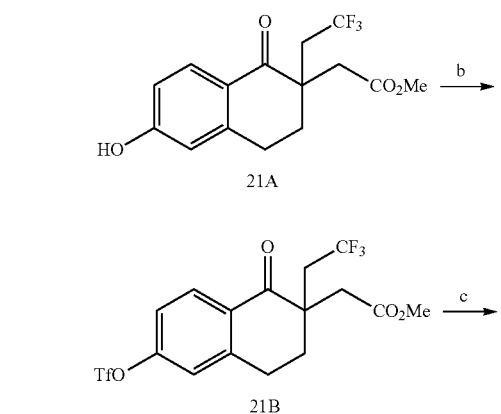

21A

21B

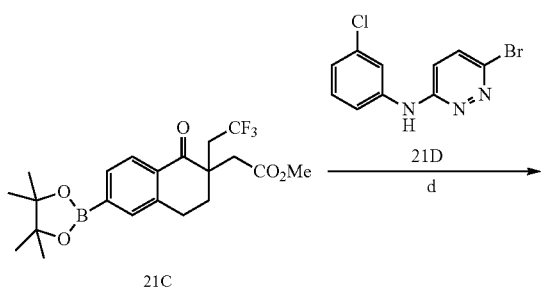

21C

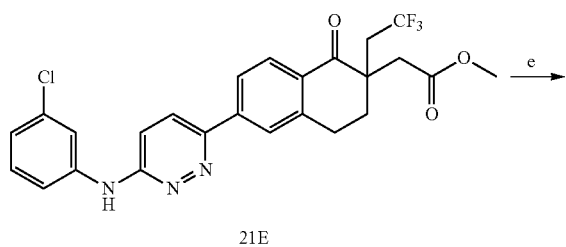

21E

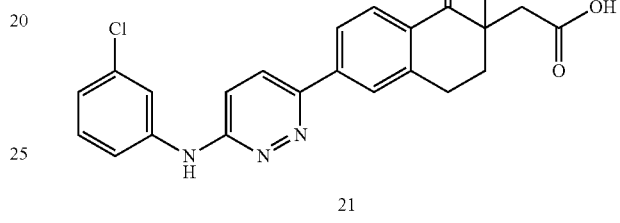

21

Reagents and conditions: a) cat. H$_2$SO$_4$, MeOH, 80° C., 3 h; b) Tf$_2$O, Py, CH$_2$Cl$_2$, RT, 3 h; c) PdCl$_2$(dppf)-CH$_2$Cl$_2$, KOAc, Dioxane, 80° C., 5 h; d) Pd(PPh$_3$)$_4$, Cs$_2$CO$_3$, Dioxane-H$_2$O, 80° C., 3 h; then chiral separation; e) LiOH, EtOH—H$_2$O, RT, 4 h.

Procedures 2-(6-(6-(3-chlorophenylamino)pyridazin-3-yl)-1-oxo-2-(2,2,2-trifluoroethyl)-1,2,3,4-tetrahydronaphthalen-2-yl)acetic acid (enantiomer-1)

Methyl 2-(6-hydroxy-1-oxo-2-(2,2,2-trifluoroethyl)-1,2,3,4-tetrahydronaphthalen-2-yl)acetate (21A)

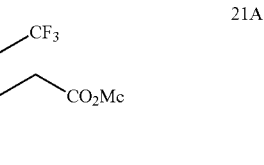

21A

Sulfuric acid (2 mL) was added to a solution of 1E (8.5 g, 28.1 mmol) in methanol (80 mL), and the mixture was stirred at 80° C. for 3 h. Methanol was removed from reaction mixture under reduced pressure, and the residue was diluted with ethyl acetate and extracted with saturated NaHCO$_3$ solution and brine solution. The organic layer was dried over sodium sulfate and filtered, and the filtrate was concentrated under reduced pressure to give the title compound (8.5 g, 91%) as a syrup. $^1$H NMR (400 MHz, DMSO-d$_6$) δ 10.43 (s, 1H), 7.77 (d, J=8.6 Hz, 1H), 6.75 (dd, J$_1$=8.7 Hz, J$_2$=2.4 Hz, 1H), 6.65 (s, 1H), 3.57 (s, 3H), 3.05-2.78 (m, 4H), 2.73-2.55 (m, 2H), 2.32 (m, 1H), 2.09 (m, 1H). ESI-MS m/z: 317 (M+H)$^+$.

Methyl 2-(1-oxo-2-(2,2,2-trifluoroethyl)-6-(trifluoromethylsulfonyloxy)-1,2,3,4-tetrahydronaphthalen-2-yl)acetate (21B)

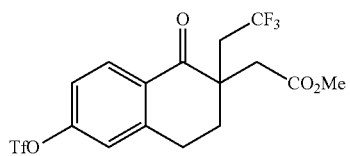

Trifluoroacetic anhydride (5.45 mL, 32.3 mmol) was added to an ice cold solution of 21A (8.5 g, 26.9 mmol) and pyridine (2.61 mL, 32.3 mmol) in dichloromethane (100 mL), and the mixture was stirred at room temperature for 3 h. The reaction mixture was diluted with dichloromethane and extracted with saturated aqueous solution NaCl. The organic layer was dried over sodium sulfate and filtered, and the filtrate was concentrated under reduced pressure to give the title compound (9 g, 74%) as a syrup. $^1$H NMR (300 MHz, CDCl$_3$): δ 8.16 (d, J=8.7 Hz, 1H), 7.29-7.15 (m, 2H), 3.68 (s, 3H), 3.09 (t, J=6.3 Hz, 2H), 2.98-2.78 (m, 2H), 2.66 (d, J=16.5 Hz, 1H), 2.59-2.44 (m, 2H), 2.36 (m, 1H).

Methyl 2-(1-oxo-6-(4,4,5,5-tetramethyl-1,3,2-dioxaborolan-2-yl)-2-(2,2,2-trifluoroethyl)-1,2,3,4-tetrahydronaphthalen-2-yl)acetate (21C)

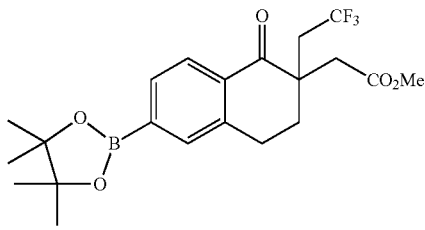

PdCl$_2$(dppf)-CH$_2$Cl$_2$ adduct (0.114 g, 0.156 mmol) was added to a solution of 21B (1.4 g, 3.12 mmol) in 30 mL of 1,4 dioxane in argon atmosphere, followed by potassium acetate (0.919 g, 9.37 mmol) and 4,4,4',4',5,5,5',5'-octamethyl-2,2'-bi(1,3,2-dioxaborolane) (0.952 g, 3.75 mmol). The mixture was degassed for 5 min. The reaction mixture was refluxed for 5 h, cooled to room temperature and filtered over celite bed. The filtrate was concentrated under reduced pressure, and the residue was purified by flash chromatography using 10% ethyl acetate in hexane to afford the title compound (1.2 g, 51%) as viscous liquid. $^1$H NMR (400 MHz, CDCl$_3$): δ 8.01 (d, J=8.0 Hz, 1H), 7.75 (d, J=7.6 Hz, 1H), 7.70 (s, 1H), 3.66 (s, 3H), 3.04 (t, J=6.4 Hz, 2H), 2.88-2.78 (m, 2H), 2.66-2.55 (m, 2H), 2.46-2.25 (m, 2H), 1.24-1.19 (m, 12H). ESI-MS m/z: 427 (M+H)$^+$.

6-Bromo-N-(3-chlorophenyl)pyridazin-3-amine (21D)

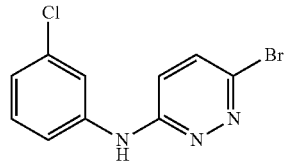

3,6-Dibromopyridazine (1 g, 4.20 mmol) was added to a solution of 3-chloroaniline (0.536 g, 4.20 mmol) in 1,4-dioxane (10 mL) followed by 4M HCl in 1,4-dioxane (6 mL, 24 mmol). The mixture was refluxed for 3 h. The slurry obtained was filtered, and the crude product was purified by preparative HPLC to afford the title compound 21D (0.3 g, 23%) as a solid. $^1$H NMR (300 MHz, DMSO-d$_6$): δ 9.67 (s, 1H), 8.09 (t, J=1.8 Hz, 1H), 7.7 (d, J=9.0 Hz, 1H), 7.5 (dd, J$_1$=9.0 Hz, J$_2$=0.9 Hz, 1H), 7.35 (t, J=8.1 Hz, 1H), 7.12 (d, J=9.6 Hz, 1H), 7.05 (dd, J$_1$=8.1 Hz, J$_2$=0.9 Hz, 1H). ESI-MS m/z: 284 (M+H)$^+$.

Methyl 2-(6-(6-((3-chlorophenyl)amino)pyridazin-3-yl)-1-oxo-2-(2,2,2-trifluoroethyl)-1, 2, 3,4-tetrahydronaphthalen-2-yl)acetate (enantiomer-1) (21E1)

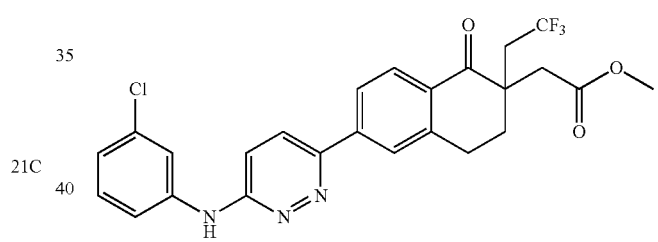

Pd(PPh$_3$)$_4$ (0.095 g, 0.082 mmol) was added to a solution of 21D (0.7 g, 1.642 mmol) in 13 mL of 1,4 dioxane-H$_2$O (3:1) mixture under argon atmosphere, followed by 21C (0.374 g, 1.314 mmol) and cesium carbonate (1.605 g, 4.93 mmol). The mixture was degassed for 15 min. The reaction mixture was refluxed for 3 h, and solvent was removed under reduced pressure. The residue was partitioned between ethyl acetate and water. The separated organic layer was dried over sodium sulfate and filtered, and the filtrate was concentrated under reduced pressure to give the crude product which was purified by flash chromatography using 35% ethyl acetate in hexane to afford racemic 21E (0.3 g, 36%) as a yellow solid.

Compound 21E (0.3 g) was separated by chiral HPLC to obtain 21E1 (Rt 7.41 min) and 21E2 (Rt 8.31 min) using following conditions.

Column: CHIRAL PAK IA 4.6×250 mm, 5µ
Mobile Phase: A=n-HEXANE (0.1% DEA), B=Ethanol; ISOCRATIC: 60:40; Flow rate: 1.0 mL/min $^1$H NMR for compound 21E1 (300 MHz, DMSO-d6): δ 9.69 (s, 1H), 8.16 (d, J=1.6 Hz, 1H), 8.12 (d, J=9.6 Hz, 1H), 8.05 (m, 2H), 7.97 (d, J=8.0 Hz, 1H), 7.54 (dd, J$_1$=8.4 Hz, J$_2$=1.2 Hz, 1H), 7.33 (t, J=8.0 Hz, 1H), 7.24 (d, J=9.2 Hz, 1H), 7.01 (dd, J$_1$=8.0 Hz, J$_2$=1.6 Hz, 1H), 3.55 (s, 3H), 3.28-2.89 (m, 4H), 2.74-2.66 (m, 2H), 2.40 (m, 1H), 2.17 (m, 1H). ESI-MS m/z: 504 (M+H)⁺.

2-(6-(6-((3-chlorophenyl)amino)pyridazin-3-yl)-1-oxo-2-(2,2,2-trifluoroethyl)-1,2,3,4-tetrahydronaphthalen-2-yl) acetic acid (enantiomer-1) (21)

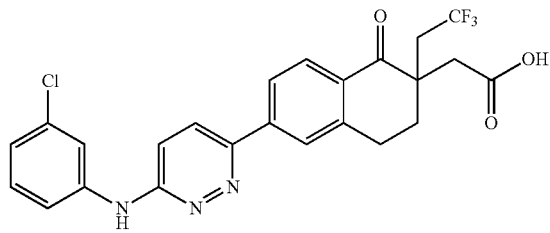

Lithium hydroxide (0.063 g, 1.49 mmol) was added to a solution of 21E1 (0.15 g, 0.298 mmol) in 6 mL of ethanol-water (3:1) mixture, and the reaction mixture was stirred at room temperature for 4 h. After the solvent was removed in vacuo, the residue was diluted with water. The aqueous layer was acidified by addition of saturated citric acid solution until pH 2 was attained. The resulting solution was cooled to 0° C., and solids obtained were filtered off and dried under vacuum to afford the title compound 21 (0.118 g, 78%) as a yellow solid. ¹H NMR (400 MHz, DMSO-d₆) δ 12.6 (bs, 1H), 9.78 (s, 1H), 8.19 (s, 1H), 8.13 (d, J=9.6 Hz, 1H), 8.07-7.95 (m, 3H), 7.58 (d, J=8.0 Hz, 1H), 7.36 (t, J=8.0 Hz, 1H), 7.28 (d, J=9.2 Hz, 1H), 7.03 (d, J=7.6 Hz, 1H), 3.24-2.87 (m, 5H), 2.68 (d, J=15.2 Hz, 1H), 2.34 (d, J=14.4 Hz, 1H), 2.14 (m, 1H). ESI-MS m/z: 490 (M+H)⁺; HPLC purity: 97%.

Example 22

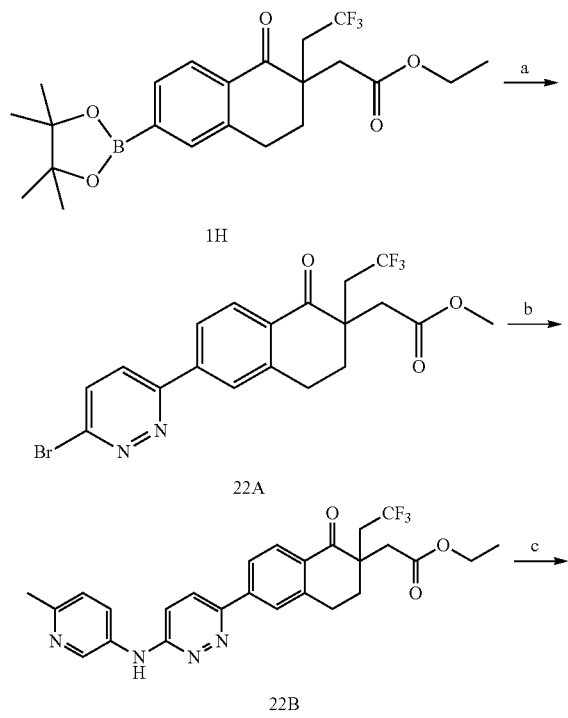

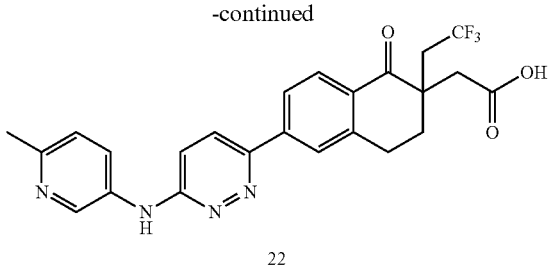

Reagents and conditions: a) PdCl₂(dppf), 3,6-dibromopyridazine, Cs₂CO₃, Dioxane-H₂O, 80°C., 2 h; b) 6-methylpyridin-3-amine, Pd₂(dba)₃, Xantphos, Cs₂CO₃, Dioxane, 80° C., 2 h; then chiral separation; c) LiOH, EtOH—H₂O, RT, 8 h.

Procedures 2-(6-(6-(6-methylpyridin-3-ylamino)pyridazin-3-yl)-1-oxo-2-(2,2,2-trifluoroethyl)-1,2,3,4-tetrahydronaphtha-len-2-yl)acetic acid (enantiomer-1)

Ethyl 2-(6-(6-bromopyridazin-3-yl)-1-oxo-2-(2,2,2-trifluoroethyl)-1,2,3,4-tetrahydronaphthalen-2-yl)acetate (22A)

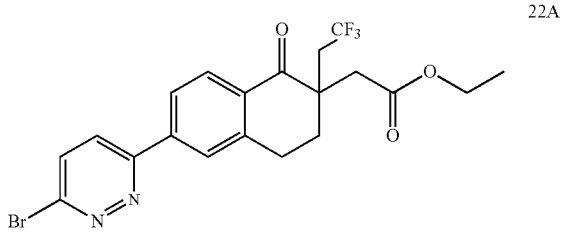 [SMILES: CCOC(=O)CC1(CC(F)(F)F)CCc2cc(-c3ccc(Br)nn3)ccc2C1=O]

Pd(dppf)Cl₂ (0.154 g, 0.21 mmol) was added to a solution of 3,6-dibromo pyridazine (1 g, 4.2 mmol) in 16 mL of 1,4 dioxane-H₂O (3:1) mixture under argon atmosphere, followed by cesium carbonate (4.11 g, 12.61 mmol) and 1H (1.85 g, 4.2 mmol). The mixture was degassed for 5 min. The reaction mixture was refluxed for 2 h, solvent was removed under reduced pressure, and the residue was partitioned between ethyl acetate and water. The separated organic layer was dried over sodium sulfate and filtered, and the filtrate was concentrated under reduced pressure. The crude product was purified by flash chromatography using 10% ethyl acetate in hexane to afford the title compound (0.8 g, 40%) as a solid. ¹H NMR (300 MHz, CDCl₃): δ 8.19 (d, J=8.1 Hz, 1H), 8.06 (s, 1H), 7.90 (dd, J₁=2.1 Hz, J₂=8.7 Hz, 1H), 7.77 (s, 2H), 4.14 (q, J=6.9 Hz, 2H), 3.16 (t, J=6.0 Hz, 2H), 2.95-2.82 (m, 2H), 2.69-2.57 (m, 2H), 2.53-2.32 (m, 2H), 1.24 (t, J=7.2 Hz, 3H). ESI-MS m/z: 471 (M+H)⁺.

Ethyl 2-(6-(6-(6-methylpyridin-3-ylamino)pyridazin-3-yl)-1-oxo-2-(2,2,2-trifluoroethyl)-1,2,3,4-tetrahydro-naphthalen-2-yl)acetate (enantiomer-1) (22B1)

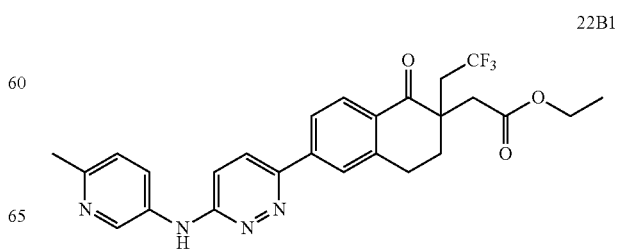

Pd$_2$(dba)$_3$ (0.29 g, 0.318 mmol) and Xantphos (0.184 g, 0.318 mmol) were added to a solution of 22A (1.5 g, 3.18 mmol) in 20 mL of 1,4-dioxane under argon atmosphere, followed by cesium carbonate (3.11 g, 9.55 mmol) and 6-methylpyridin-3-amine (0.344 g, 3.18 mmol). The mixture was degassed for 10 min. The reaction mixture was stirred at 80° C. for 3 h in a sealed tube and allowed to room temperature. The reaction mixture was diluted with ethyl acetate and water. The separated organic layer was dried over sodium sulfate and filtered, and the filtrate was concentrated under reduced pressure. The crude product was purified by flash chromatography using chloroform to afford racemic compound 22B (0.38 g, 24%) as a solid.

Compound 22B (0.37 g) was a racemic mixture with 1:1 enantiomeric ratio and was separated on a chiral column to obtain 22B1 (Rt 8.27 min) and 22B2 (Rt 14.7 min) using following conditions.

Column: CHIRAL PAK IA 4.6×250 mm, 5μ

Mobile Phase: A=n-HEXANE (0.1% DEA), B=Ethanol; ISOCRATIC: 30:70; Flow rate: 1.0 mL/min.

$^1$H NMR for compound 22B1 (300 MHz, DMSO-d$_6$): δ 9.58 (s, 1H), 8.76 (d, J=2.7 Hz, 1H), 8.22 (dd, J$_1$=8.4 Hz, J$_2$=2.7 Hz, 1H), 8.12 (d, J=8.7 Hz, 1H), 8.09-7.97 (m, 3H), 7.25 (d, J=2.7 Hz, 1H), 7.23 (s, 1H), 4.04 (q, J=6.9 Hz, 2H), 3.15-2.97 (m, 3H), 2.92 (d, J=15.9 Hz, 1H), 2.78-2.66 (m, 2H), 2.44 (s, 3H), 2.40 (m, 1H), 2.22 (m, 1H), 1.15 (t, J=7.2 Hz, 3H). ESI-MS m/z: 499 (M+H)$^+$.

2-(6-(6-(6-methylpyridin-3-ylamino)pyridazin-3-yl)-1-oxo-2-(2,2,2-trifluoroethyl)-1,2,3,4-tetrahydronaphtha-len-2-yl)acetic acid (enantiomer-1) (22)

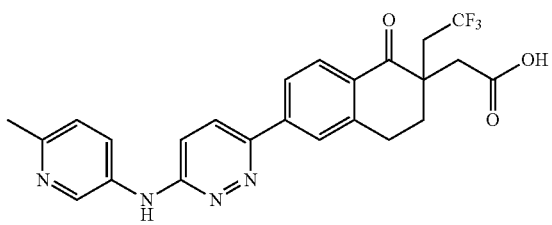

22

Lithium hydroxide (0.042 g, 1 mmol) was added to a solution of 22B1 (0.125 g, 0.25 mmol) in 6 mL of ethanol-water (3:1) mixture, and the reaction mixture was stirred at room temperature for 8 h. After the solvent was removed in vacuo, the residue was dissolved in water. The aqueous layer was acidified by addition of saturated solution of citric acid until pH 4 was attained. The resulting solution was cooled to 0° C., and solids obtained were filtered off and dried under vacuum to afford the title compound (0.105 g, 89%) as a solid. $^1$H NMR (300 MHz, DMSO-d$_6$): δ 12.4 (bs, 1H), 9.59 (s, 1H), 8.76 (d, J=2.7 Hz, 1H), 8.22 (dd, J$_1$=2.7 Hz, J$_2$=8.4 Hz, 1H), 8.11 (d, J=9.6 Hz, 1H), 8.05-7.97 (m, 3H), 7.25 (d, J=3.0 Hz, 1H), 7.23 (s, 1H), 3.15-2.95 (m, 3H), 2.84 (d, J=16.2 Hz, 1H), 2.78-2.65 (m, 1H), 2.58 (d, J=16.5 Hz, 1H), 2.46 (m, 1H), 2.43 (s, 3H), 2.19 (m, 1H). ESI-MS m/z: 471 (M+H)$^+$; HPLC purity: 98%.

Examples 23-25 were prepared using procedures analogous to those described in Example 21-22 with appropriate starting materials.

| Ex | Structure | Analytical Data | Mass/Purity |
| --- | --- | --- | --- |
| 23 (enantiomer-1) | | $^1$H NMR (400 MHz, DMSO-d$_6$) δ 12.4 (bs, 1H), 10.23 (s, 1H), 8.99 (d, J = 2.0 Hz, 1H), 8.71 (d, J = 7.2 Hz, 1H), 8.21 (d, J = 9.2 Hz, 1H), 8.09-8.0 (m, 3H), 7.89 (d, J = 8.8 Hz, 1H), 7.38 (d, J = 9.6 Hz, 1H), 3.18-2.92 (m, 4H), 2.78-2.62 (m, 2H), 2.48 (m, 1H), 2.17 (m, 1H). | ESI-MS m/z = 525 (M + H)$^+$; HPLC purity: 99%. |
| 24 (enantiomer-2) | | $^1$H NMR (400 MHz, DMSO-d$_6$) δ 12.4 (bs, 1H), 10.23 (s, 1H), 8.99 (s, 1H), 8.71 (d, J = 8.0 Hz, 1H), 8.21 (d, J = 9.2 Hz, 1H), 8.1-7.95 (m, 3H), 7.89 (d, J = 8.8 Hz, 1H), 7.38 (d, J = 9.2 Hz, 1H), 3.20-2.92 (m, 4H), 2.78-2.62 (m, 2H), 2.48 (m, 1H), 2.17 (m, 1H). | ESI-MS m/z = 525 (M + H)$^+$; HPLC purity: 99%. |

| Ex | Structure | Analytical Data | Mass/Purity |
|---|---|---|---|
| 25 | (enantiomer-1) | $^1$H NMR (300 MHz, DMSO-$d_6$) δ 11.57 (bs, 1H), 8.21 (d, J = 9.4 Hz, 1H), 8.12-7.96 (m, 3H), 7.46 (d, J = 9.4 Hz, 1H), 7.13 (d, J = 1.5 Hz, 1H), 3.16-2.85 (m, 5H), 2.71 (d, J = 15.0 Hz, 1H), 2.50-2.39 (m, 1H), 2.38 (s, 3H), 2.14 (m, 1H). | ESI-MS m/z = 477 (M + H)$^+$; LCMS purity: 98%. |

Example 26

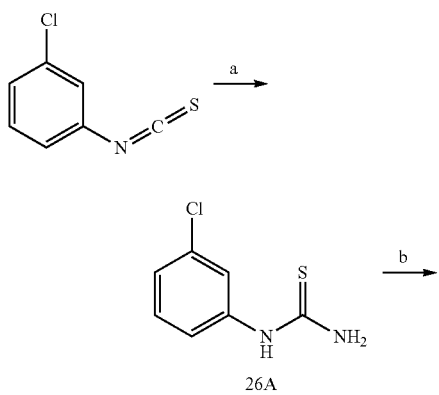

26A

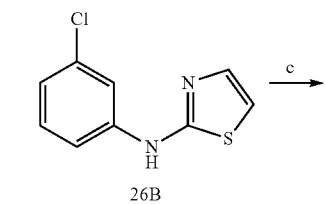

26B

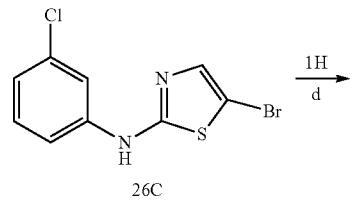

26C

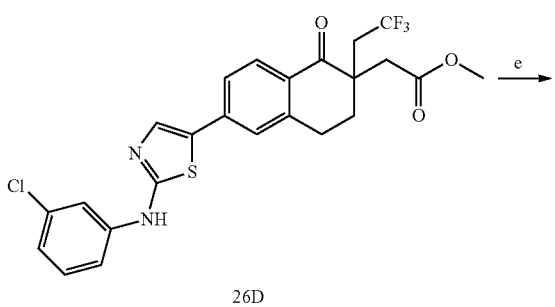

26D

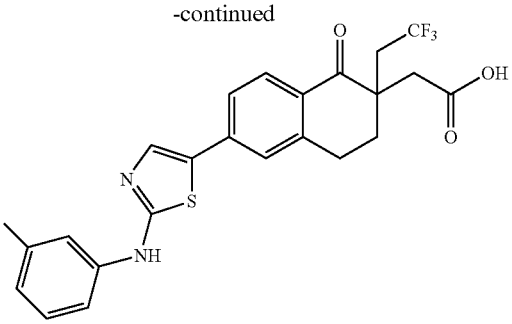

26

Reagents and conditions: a) 0.5 M NH$_3$, Dioxane, RT. 0.16 h; b) ClCH$_2$CHO, EtOH—H$_2$O, 60° C., 16 h; c) NBS, CH$_2$Cl$_2$, RT, 0.16 h; d) PdCl$_2$(dppf)-CH$_2$Cl$_2$, Cs$_2$CO$_3$, Dioxane-H$_2$O, 80° C., 3 h; then chiral separation; e) LiOH, EtOH—H$_2$O, RT, 1 h.

Procedures 2-(6-(2-(3-Chlorophenylamino)thiazol-5-yl)-1-oxo-2-(2,2,2-trifluoroethyl)-1,2,3,4-tetrahydronaphthalen-2-yl)acetic acid (enantiomer-2)

1-(3-Chlorophenyl)thiourea (26A)

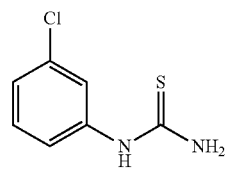

26A

1-Chloro-3-isothiocyanatobenzene (15 g, 88 mmol) was added to a solution of 0.5 M ammonia in 1,4-dioxane (80 mL), and the mixture was stirred at room temperature for 0.16 h. The reaction mixture was concentrated in vacuo, and partitioned between ethyl acetate and water. The separated organic layer was washed with saturated NaCl solution, dried over sodium sulfate and filtered, and the filtrate was concentrated in vacuo to afford the title compound (15.5 g, 89%) as a solid. $^1$H NMR (400 MHz, DMSO-$d_6$) δ 9.80 (s, 1H), 7.70 (s, 1H), 7.52 (bs, 2H), 7.38-7.27 (m, 2H), 7.15 (dt, J$_1$=7.0 Hz, J$_2$=2.1 Hz, 1H). ESI-MS m/z: 187 (M+H)$^+$.

N-(3-chlorophenyl)thiazol-2-amine (26B)

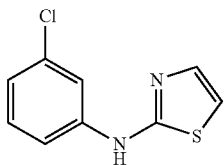

Aqueous chloro acetaldehyde solution (15 mL) was added to a solution of 26A (15.5 g, 80 mmol) in ethanol (150 mL) and stirred at 60° C. for 16 h. The reaction mixture was concentrated in vacuo, and partitioned between ethyl acetate and water. The separated organic layer was washed with saturated NaCl, dried over sodium sulfate and filtered, and the filtrate was concentrated in vacuo. The crude product was purified by flash chromatography using 10% ethyl acetate in hexane to afford the title compound (15 g, 81%) as a white solid. $^1$H NMR (400 MHz, DMSO-$d_6$): δ 10.39 (s, 1H), 7.96 (t, J=2.1 Hz, 1H), 7.45-7.38 (dd, =2.0 Hz, $J_2$=8.4 Hz, 1H), 7.37-7.26 (m, 2H), 7.02-6.95 (m, 2H). ESI-MS m/z: 211 (M+H)$^+$.

5-bromo-N-(3-chlorophenyl)thiazol-2-amine (26C)

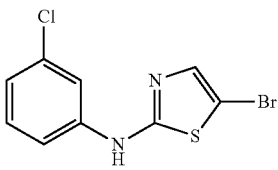

N-Bromosuccinimide (7.60 g, 42.7 mmol) was added to a solution of 26B (10 g, 47.5 mmol) in dichloromethane (150 mL), and the mixture was stirred at room temperature for 0.16 h. The reaction mixture was diluted with dichloromethane and water, separated organic layer was dried over sodium sulfate and filtered, and the filtrate was concentrated under reduced pressure. The crude product was purified by flash chromatography using 15% ethyl acetate in hexane to afford the title compound (2.54 g, 18%) as pale yellow solid. $^1$H NMR (400 MHz, DMSO-$d_6$): δ 10.54 (s, 1H), 7.87 (t, J=2.0 Hz, 1H), 7.41-7.26 (m, 3H), 7.01 (dt, $J_1$=7.3 Hz, $J_2$=1.8 Hz, 1H). ESI-MS m/z: 291 (M+H)$^+$.

Methyl 2-(6-(2-(3-chlorophenylamino)thiazol-5-yl)-1-oxo-2-(2,2,2-trifluoroethyl)-1,2,3,4-tetrahydronaphthalen-2-yl)acetate (enantiomer-2) (26D2)

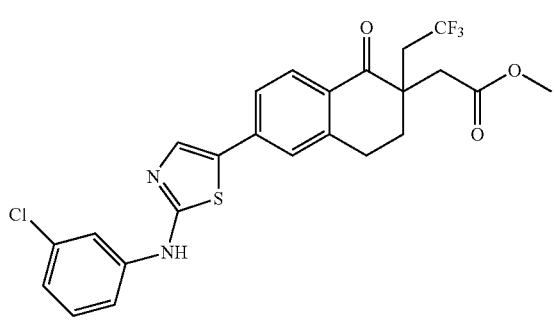

PdCl$_2$(dppf)-CH$_2$Cl$_2$ (0.192 g, 0.235 mmol) was added to a solution of 26C (2 g, 4.69 mmol) in 34 mL of 1,4 dioxane-H$_2$O (3:1) mixture under argon atmosphere, followed by 1H (1.22 g, 4.22 mmol) and cesium carbonate (2.29 g, 7.04 mmol). The reaction mixture was degassed for 15 min. The reaction mixture was refluxed for 3 h, and solvent was removed under reduced pressure. The residue was partitioned between ethyl acetate and water, separated organic layer was dried over sodium sulfate and filtered, and the filtrate was concentrated under reduced pressure. The crude product was purified by flash chromatography using 25% ethyl acetate in hexane to afford racemic compound 26D (0.35 g, 14%) as a yellow solid.

Compound 26D (0.35 g) was separated by chiral HPLC to obtain 26D1 (Rt 6.1 min) and 26D2 (Rt 7.38 min) using following conditions.

Column: CHIRALCEL OX 4.6×250 mm, 5μ

Mobile Phase: A=n-HEXANE (0.1% TFA), B=IPA; ISOCRATIC: 70:30; Flow rate: 1.0 mL/min.

$^1$H NMR for compound 26D2 (400 MHz, Chloroform-d) δ 8.02 (d, J=8.3 Hz, 1H), 7.81 (s, 1H), 7.62 (s, 1H), 7.47 (t, J=2.0 Hz, 1H), 7.42 (dd, $J_1$=1.6 Hz, $J_2$=8.4 Hz, 1H), 7.31-7.22 (m, 3H), 7.07 (d, J=7.6 Hz, 1H), 3.66 (s, 3H), 3.04 (t, J=6.4 Hz, 2H), 2.93-2.76 (m, 2H), 2.68-2.37 (m, 3H), 2.31 (m, 1H). ESI-MS m/z: 509 (M+H)$^+$.

2-(6-(2-(3-Chlorophenylamino)thiazol-5-yl)-1-oxo-2-(2,2,2-trifluoroethyl)-1,2,3,4-tetrahydronaphthalen-2-yl)acetic acid (enantiomer-2) (26)

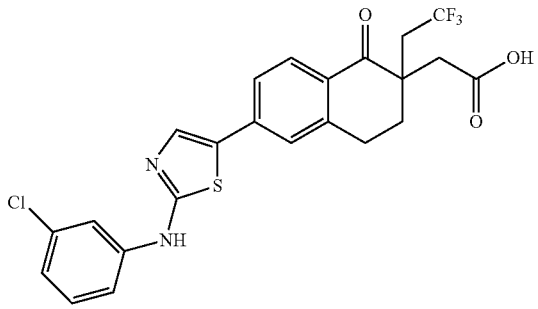

Lithium hydroxide (0.05 g, 1.18 mmol) was added to a solution of 26D2 (0.12 g, 0.236 mmol) in 8 mL of ethanol-water (3:1) mixture, and the reaction mixture was stirred at room temperature for 1 h. After the solvent was removed in vacuo, the residue was dissolved in water. The aqueous layer was acidified by addition of saturated citric acid solution until pH 2 was attained. The resulting solution was cooled to 0° C. and solids obtained were filtered off and dried under vacuum to afford the title compound (0.07 g, 59%) as a yellow solid. $^1$H NMR (300 MHz, DMSO-$d_6$) δ 10.9 (s, 1H), 7.95 (m, 2H), 7.88 (d, J=8.4 Hz, 1H), 7.56 (d, J=8.1 Hz, 1H), 7.5 (m, 2H), 7.35 (t, J=8.1 Hz, 1H), 7.02 (d, J=8.0 Hz, 1H), 3.14-2.80 (m, 4H), 2.69 (d, J=18.4 Hz, 1H), 2.46-2.31 (m, 2H), 2.12 (m, 1H). ESI-MS m/z: 495 (M+H)$^+$; HPLC purity: 99%

Examples 27-28 were prepared using procedures analogous to those described in Example 26 with appropriate starting materials.

| Ex | Structure | Analytical Data | Mass/Purity |
|---|---|---|---|
| 27 | 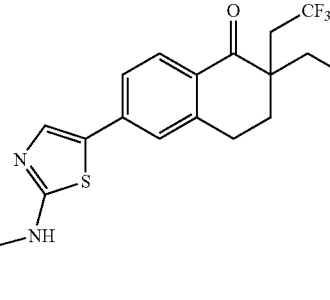<br>(enantiomer-1) | ¹H NMR (400 MHz, DMSO-$d_6$) δ 11.4 (bs, 1H), 8.88 (s, 1H), 8.51 (d, J = 8.8 Hz, 1H), 8.0 (s, 1H), 7.88 (t, J = 8.8 Hz, 1H), 7.61 (d, J = 8.4 Hz, 1H), 7.52 (s, 1H), 3.14-2.95 (m, 3H), 2.90-2.65 (m, 2H), 2.46-2.30 (m, 2H), 2.12 (m, 1H). | ESI-MS m/z = 530 (M + H)⁺. HPLC purity: 92%. |
| 28 | 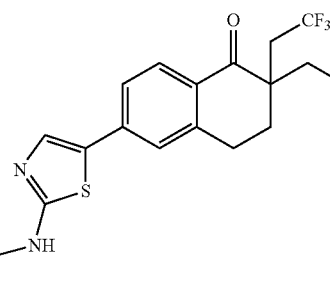<br>(enantiomer-2) | ¹H NMR (400 MHz, DMSO-$d_6$) δ 11.4 (bs, 1H), 8.88 (s, 1H), 8.51 (d, J = 8.4 Hz, 1H), 8.0 (s, 1H), 7.88 (t, J = 8.4 Hz, 1H), 7.61 (d, J = 8.0 Hz, 1H), 7.52 (s, 1H), 3.18-2.80 (m, 4H), 2.75-2.65 (m, 1H), 2.46-2.35 (m, 2H), 2.12 (m, 1H). | ESI-MS m/z = 530 (M + H)⁺. HPLC purity: 98.7%. |

Biological Assay

Inhibition of human DGAT1 activity in vitro

Human DGAT1 was expressed in Sf9 insect cells using a baculovirus expression system. Microsomes were prepared and used as enzyme for in vitro inhibition testing in either of two formats measuring production of coenzyme A or tridecanoylglycerol product, respectively. All steps were performed at 21-23° C. All data for DGAT1 inhibition by test compounds were collected under conditions where product formation was linear with reaction time.

CPM Assay:

For inhibition of CoA product formation, test compounds were prepared in 100% DMSO, diluted 100-fold into assay buffer, and 10 uL added to 96-well half-area plates (Greiner 675076). An equal volume (10 uL) of 3× enzyme in buffer was added and the components incubated for 30 minutes pre-reaction incubation to allow enzyme and test compounds to attain binding equilibrium. The 3× enzyme mixture contained 30 uM {4-[4-(4-amino-7,7-dimethyl-7H-pyrimido[4,5-b][1,4]oxazin-6-yl)phenyl]cyclohexyl}acetic acid for fully inhibited control wells. Some assays were performed with inclusion of didecanoylglycerol in the pre-reaction incubation of test compound and enzyme. DGAT reactions (30 uL) were initiated upon addition of 10 uL of 3× substrate solution. Final reaction conditions consisted of 20 mM HEPES pH 7.5, 2 mM $MgCl_2$, 1 mM CHAPS, 50 uM didecanoylglycerol, 3 uM decanoyl-CoA, 1 ug/mL microsomal protein, and 1% DMSO. Following a 60 minute reaction incubation, reactions were stopped and CoA product derivatized with 30 uL of buffer containing 10 uM {4-[4-(4-amino-7,7-dimethyl-7H-pyrimido[4,5-b][1,4]oxazin-6-yl)phenyl]cyclohexyl}acetic acid and 50 uM 7-diethylamino-3-(4'-maleimidylphenyl)-4-methylcoumarin (CPM). Fluorescence was read using Envision reader at Ex 405 nm/Em 480 nm about 30 minutes after addition of final solution. Inhibition was normalized to controls containing DMSO or 10 uM {4-[4-(4-amino-7,7-dimethyl-7H-pyrimido[4,5-b][1,4]oxazin-6-yl)phenyl]cyclohexyl}acetic acid. $IC_{50}$s were fitted using GraphPad Prism to a sigmoidal dose response.

LE Assay:

For inhibition of triacylglycerol product formation, 11 uL reactions were run in white Polyplate-384 (PerkinElmer6007300) starting with a 30 minute pre-reaction incubation of 5 uL of 2.2× enzyme and 1 uL of 100% DMSO containing test compound or control compound, {4-[4-(4-amino-7,7-dimethyl-7H-pyrimido[4,5-b][1,4]oxazin-6-yl)phenyl]cyclohexyl}acetic acid. Some assays were performed with inclusion of didecanoylglycerol in the pre-reaction incubation of test compounds and enzyme. Reactions were initiated after 30 minute pre-reaction incubation via addition of 5 uL of 2.2× substrate. Final reaction conditions consisted of 50 mM HEPES pH 7.5, 2 mM $MgCl_2$, 1 mM CHAPS, 25 uM didecanoylglycerol, 0.5 uM decanoyl-CoA, 0.3 nCi/uL [$^{14}C$]-decanoyl-CoA or 0.5 nCi/uL [$^{3}H$]-decanoyl-CoA, 0.05-4 ug/mL microsomal protein, and 1% DMSO. Following 60 minute reaction incubation, reactions were stopped with 40 uL of 45% isopropanol and 50 mM sodium carbonate in water and mixed. Extraction of tridecanoylglycerol product was accomplished via addition of 30 uL Microscint-E (Perkin Elmer) and 2 hours of incubation (sealed). Plates were read on a Microbeta Microplate reader. Inhibition was normalized to controls containing DMSO or 10 uM {4-[4-(4-amino-7,7-dimethyl-7H-pyrimido[4,5-b][1,4]oxazin-6-yl)phenyl]cyclohexyl}acetic acid. $IC_{50}$s were fitted using GraphPad Prism to a sigmoidal dose response.

Biological Data

Exemplified compounds of the present invention were tested in one or more DGAT assays described above and were found to be inhibitors of DGAT1 with IC$_{50}$<10 μM. Data for specific examples tested in the human DGAT1 lipid extraction (LE) assays are listed below in Table 1 as follows: +=10 μM>IC$_{50}$>500 nM; ++=500 nM≥IC$_{50}$>100 nM; +++=IC$_{50}$≤100 nM.

TABLE 1

| Example # | hDGAT LE IC$_{50}$ |
|---|---|
| 1 | +++ |
| 2 | +++ |
| 3 | + |
| 4 | +++ |
| 5 | ++ |
| 6 | +++ |
| 7 | +++ |
| 8 | +++ |
| 9 | ++ |
| 10 | +++ |
| 11 | ++ |
| 12 | +++ |
| 13 | ++ |
| 14 | +++ |
| 15 | + |
| 16 | ++ |
| 17 | ++ |
| 18 | ++ |
| 19 | ++ |
| 20 | + |
| 21 | +++ |
| 22 | +++ |
| 23 | +++ |
| 24 | + |
| 25 | + |
| 26 | ++ |
| 27 | ++ |
| 28 | +++ |

The invention claimed is:

1. A compound of Formula (I):

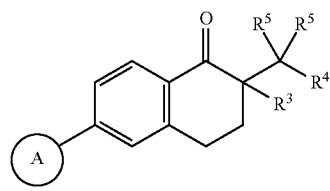

wherein:

A represents

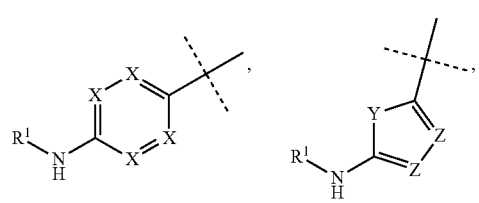

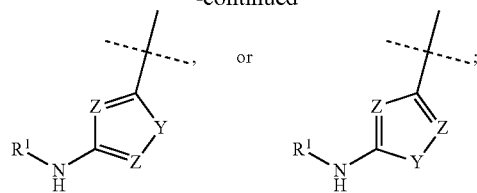

each X is independently CH, CR$^2$, or N, provided that at least one X is CH and at most two X's are N;
Y is O, S, or NR$^6$;
each Z is independently CH, CR$^2$, or N;
R$^1$ is phenyl or 5- or 6-membered heteroaryl, which is optionally substituted by —O(C$_1$-C$_2$)alkylO— or optionally substituted with one to three substituents independently selected from halogen, cyano, (C$_1$-C$_6$) alkyl, halo(C$_1$-C$_6$)alkyl, hydroxy(C$_1$-C$_4$)alkyl, cyano (C$_1$-C$_4$)alkyl, —C(O)OR$^6$, —C(O)R$^6$, and —OR$^6$;
each R$^2$ is independently selected from the group consisting of halogen, cyano, (C$_1$-C$_4$)alkyl, halo(C$_1$-C$_4$)alkyl, and —OR$^6$;
R$^3$ is (C$_1$-C$_4$)alkyl, halo(C$_1$-C$_4$)alkyl, hydroxyl, or (C$_1$-C$_4$)alkoxy;
R$^4$ is —C(O)OR$^6$;
each R$^5$ is hydrogen; and
each R$^6$ is independently hydrogen, (C$_1$-C$_4$)alkyl, halo (C$_1$-C$_4$)alkyl, phenyl, or 5- or 6-membered heteroaryl;
or a pharmaceutically acceptable salt thereof.

2. The compound or pharmaceutically acceptable salt according to claim 1, which is represented by Formula (II):

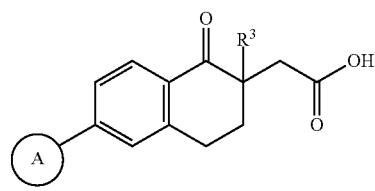

wherein:

A represents

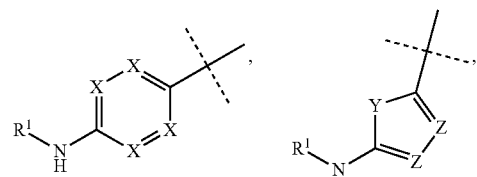

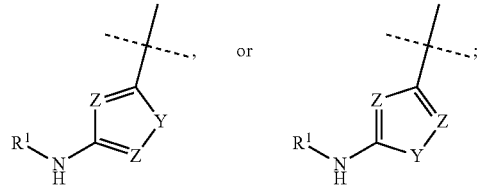

each X is independently CH, CR$^2$, or N, provided that at least one X is CH and at most two X's are N;
Y is O, S, or NR$^6$;
each Z is independently CH, CR$^2$, or N;

$R^1$ is phenyl or 5- or 6-membered heteroaryl, which is optionally substituted by —O($C_1$-$C_2$)alkylO— or optionally substituted with one to three substituents independently selected from halogen, cyano, ($C_1$-$C_6$) alkyl, halo($C_1$-$C_6$)alkyl, hydroxy($C_1$-$C_4$)alkyl, cyano ($C_1$-$C_4$)alkyl, —C(O)O$R^6$, —C(O)$R^6$, and —O$R^6$;

each $R^2$ is independently selected from the group consisting of halogen, cyano, ($C_1$-$C_4$)alkyl, halo($C_1$-$C_4$)alkyl, and —O$R^6$;

$R^3$ is ($C_1$-$C_4$)alkyl, halo($C_1$-$C_4$)alkyl, hydroxyl, or ($C_1$-$C_4$)alkoxy; and each $R^6$ is independently hydrogen, ($C_1$-$C_4$)alkyl, halo($C_1$-$C_4$)alkyl, phenyl, or 5- or 6-membered heteroaryl.

3. The compound or pharmaceutically acceptable salt according to claim 2, which is represented by Formula (III):

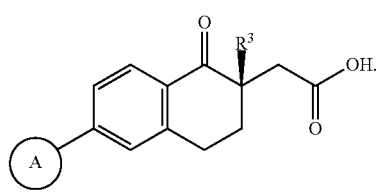

(III)

4. The compound or pharmaceutically acceptable salt according to claim 2, which is represented by Formula (IV):

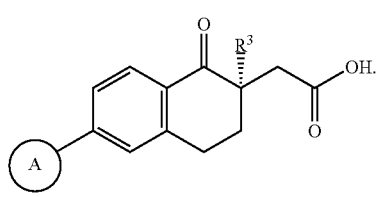

(IV)

5. The compound or pharmaceutically acceptable salt according to claim 2 wherein A represents

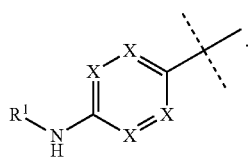

6. The compound or pharmaceutically acceptable salt according to claim 5 wherein each X is independently CH or N, provided that at most two X's are N.

7. The compound or pharmaceutically acceptable salt according to claim 2 wherein A represents

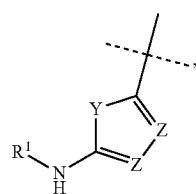

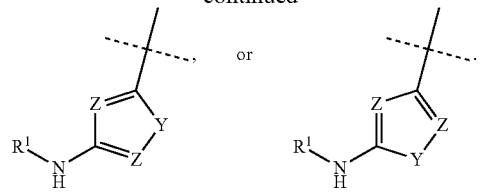

8. The compound or pharmaceutically acceptable salt according to claim 7 wherein Y is O, S, or NH; and each Z is independently CH or N.

9. The compound or pharmaceutically acceptable salt according to claim 2 wherein $R^3$ is ($C_1$-$C_4$)alkyl or halo($C_1$-$C_4$)alkyl.

10. The compound or pharmaceutically acceptable salt according to claim 2 wherein $R^3$ is halo($C_1$-$C_4$)alkyl.

11. The compound or pharmaceutically acceptable salt according to claim 2, wherein $R^1$ is phenyl which is optionally substituted by —O($C_1$-$C_2$)alkylO— or with one or two substituents independently selected from halogen, ($C_1$-$C_4$) alkyl, halo($C_1$-$C_4$)alkyl, hydroxyl, and ($C_1$-$C_4$)alkoxy.

12. The compound or pharmaceutically acceptable salt according to claim 2, wherein $R^1$ is furanyl, thienyl, pyrrolyl, imidazolyl, pyrazolyl, triazolyl, tetrazolyl, oxazolyl, thiazolyl, isoxazolyl, isothiazolyl, oxadiazolyl, thiadiazolyl, pyridinyl, pyridazinyl, pyrazinyl, pyrimidinyl, or triazinyl, each of which is optionally substituted with one or two substituents independently selected from halogen, ($C_1$-$C_4$) alkyl, halo($C_1$-$C_4$)alkyl, hydroxyl, and ($C_1$-$C_4$)alkoxy.

13. The compound or pharmaceutically acceptable salt according to claim 6, wherein:
   $R^1$ is phenyl or 5- or 6-membered heteroaryl, which is optionally substituted by —O($C_1$-$C_2$)alkylO— or optionally substituted with one or two substituents independently selected from halogen, ($C_1$-$C_4$)alkyl, and halo($C_1$-$C_4$)alkyl; and
   $R^3$ is ($C_1$-$C_4$)alkyl or halo($C_1$-$C_4$)alkyl.

14. The compound or pharmaceutically acceptable salt according to claim 13, wherein $R^1$ is phenyl which is optionally substituted by —O($C_1$-$C_2$)alkylO— or optionally substituted with one or two substituents independently selected from halogen, ($C_1$-$C_4$)alkyl, and halo($C_1$-$C_4$)alkyl.

15. The compound or pharmaceutically acceptable salt according to claim 13, wherein $R^1$ is pyridinyl which is optionally substituted with one or two substituents independently selected from halogen, ($C_1$-$C_4$)alkyl, and halo($C_1$-$C_4$)alkyl.

16. The compound or pharmaceutically acceptable salt according to claim 2, wherein $R^3$ is —$CH_2CF_3$.

17. The compound according to claim 1 which is:
   2-(1-oxo-2-(2,2,2-trifluoroethyl)-6-(5-(6-(trifluoromethyl)pyridin-3-ylamino)pyridin-2-yl)-1,2,3,4-tetrahydronaphthalen-2-yl)acetic acid;
   2-(6-(5-(4-chlorophenylamino)pyridin-2-yl)-1-oxo-2-(2,2,2-trifluoroethyl)-1,2,3,4-tetrahydronaphthalen-2-yl)acetic acid;
   2-(2-methyl-1-oxo-6-(5-(6-(trifluoromethyl)pyridin-3-ylamino)pyridin-2-yl)-1,2,3,4-tetrahydronaphthalen-2-yl)acetic acid;
   2-(2-ethyl-1-oxo-6-(5-(6-(trifluoromethyl)pyridin-3-ylamino)pyridin-2-yl)-1,2,3,4-tetrahydronaphthalen-2-yl)acetic acid;
   2-(6-(5-(5-chloropyridin-2-ylamino)pyridin-2-yl)-1-oxo-2-(2,2,2-trifluoroethyl)-1,2,3,4-tetrahydronaphthalen-2-yl)acetic acid;

2-(1-oxo-6-(5-(p-tolylamino)pyridin-2-yl)-2-(2,2,2-trifluoroethyl)-1,2,3,4-tetrahydronaphthalen-2-yl)acetic acid;

2-(6-(5-(3,4-difluorophenylamino)pyridin-2-yl)-1-oxo-2-(2,2,2-trifluoroethyl)-1,2,3,4-tetrahydronaphthalen-2-yl)acetic acid;

2-(6-(5-(3-chlorophenylamino)pyridin-2-yl)-1-oxo-2-(2,2,2-trifluoroethyl)-1,2,3,4-tetrahydronaphthalen-2-yl)acetic acid;

2-(6-(5-(5-methylpyridin-2-ylamino)pyridin-2-yl)-1-oxo-2-(2,2,2-trifluoroethyl)-1,2,3,4-tetrahydronaphthalen-2-yl)acetic acid;

2-(1-oxo-2-(2,2,2-trifluoroethyl)-6-(5-(6-(trifluoromethyl)pyridin-3-ylamino)pyrazin-2-yl)-1,2,3,4-tetrahydronaphthalen-2-yl)acetic acid;

2-(6-(5-(5-methylpyridin-2-ylamino)pyrazin-2-yl)-1-oxo-2-(2,2,2-trifluoroethyl)-1,2,3,4-tetrahydronaphthalen-2-yl)acetic acid;

2-(6-(5-(5-chloropyridin-2-ylamino)pyrazin-2-yl)-1-oxo-2-(2,2,2-trifluoroethyl)-1,2,3,4-tetrahydronaphthalen-2-yl)acetic acid;

2-(6-(5-(benzo[d][1,3]dioxol-5-ylamino)pyrazin-2-yl)-1-oxo-2-(2,2,2-trifluoroethyl)-1,2,3,4-tetrahydronaphthalen-2-yl)acetic acid;

2-(6-(6-(3-chlorophenylamino)pyridazin-3-yl)-1-oxo-2-(2,2,2-trifluoroethyl)-1,2,3,4-tetrahydronaphthalen-2-yl)acetic acid;

2-(6-(6-(6-methylpyridin-3-ylamino)pyridazin-3-yl)-1-oxo-2-(2,2,2-trifluoroethyl)-1,2,3,4-tetrahydronaphthalen-2-yl)acetic acid;

2-(1-oxo-2-(2,2,2-trifluoroethyl)-6-(6-(6-(trifluoromethyl)pyridin-3-ylamino)pyridazin-3-yl)-1,2,3,4-tetrahydronaphthalen-2-yl)acetic acid;

2-(6-(6-(5-methylthiazol-2-ylamino)pyridazin-3-yl)-1-oxo-2-(2,2,2-trifluoroethyl)-1,2,3,4-tetrahydronaphthalen-2-yl)acetic acid;

2-(6-(2-(3-chlorophenylamino)thiazol-5-yl)-1-oxo-2-(2,2,2-trifluoroethyl)-1,2,3,4-tetrahydronaphthalen-2-yl)acetic acid; or 2-(1-oxo-2-(2,2,2-trifluoroethyl)-6-(2-(6-(trifluoromethyl)pyridin-3-ylamino)thiazol-5-yl)-1,2,3,4-tetrahydronaphthalen-2-yl)acetic acid;

or a pharmaceutically acceptable salt thereof.

18. A pharmaceutical composition comprising the compound or pharmaceutically acceptable salt according to claim 2 and a pharmaceutically acceptable excipient.

19. A method of treating obesity comprising administering to a human in need thereof an effective amount of the compound or pharmaceutically acceptable salt according to claim 2.

20. A method of treating acne comprising administering to a human in need thereof an effective amount of the compound or pharmaceutically acceptable salt according to claim 2.

* * * * *